US011261170B2

(12) United States Patent
Zhu et al.

(10) Patent No.: US 11,261,170 B2
(45) Date of Patent: *Mar. 1, 2022

(54) AROMATIC COMPOUND, PHARMACEUTICAL COMPOSITION AND USE THEREOF

(71) Applicant: Sichuan Kelun-Biotech Biopharmaceutical Co., Ltd., Chengdu (CN)

(72) Inventors: Jiawang Zhu, Chengdu (CN); Zhiquan Song, Chengdu (CN); Dong Long, Chengdu (CN); Lichun Wang, Chengdu (CN); Jingyi Wang, Chengdu (CN)

(73) Assignee: Sichuan Kelun-Biotech Biopharmaceutical Co., Ltd., Chengdu (CN)

( * ) Notice: Subject to any disclaimer, the term of this patent is extended or adjusted under 35 U.S.C. 154(b) by 44 days.

This patent is subject to a terminal disclaimer.

(21) Appl. No.: 16/879,204

(22) Filed: May 20, 2020

(65) Prior Publication Data

US 2020/0277277 A1 Sep. 3, 2020

Related U.S. Application Data

(63) Continuation-in-part of application No. 16/652,274, filed as application No. PCT/CN2018/115615 on Nov. 15, 2018.

(30) Foreign Application Priority Data

Nov. 30, 2017 (CN) .......................... 201711234731.2

(51) Int. Cl.
| | |
|---|---|
| *C07D 401/04* | (2006.01) |
| *A61P 1/16* | (2006.01) |
| *C07D 215/14* | (2006.01) |
| *C07D 215/227* | (2006.01) |
| *C07D 215/36* | (2006.01) |
| *C07D 215/38* | (2006.01) |
| *C07D 333/56* | (2006.01) |
| *C07D 413/04* | (2006.01) |

(52) U.S. Cl.
CPC .............. *C07D 401/04* (2013.01); *A61P 1/16* (2018.01); *C07D 215/14* (2013.01); *C07D 215/227* (2013.01); *C07D 215/36* (2013.01); *C07D 215/38* (2013.01); *C07D 333/56* (2013.01); *C07D 413/04* (2013.01)

(58) Field of Classification Search
None
See application file for complete search history.

(56) References Cited

U.S. PATENT DOCUMENTS

| 3,558,612 A | 1/1971 | Kuhn et al. |
| 2005/0171149 A1 | 8/2005 | Najib et al. |
| 2007/0032543 A1 | 2/2007 | Delhomel et al. |
| 2012/0252725 A1 | 10/2012 | Darteil et al. |

FOREIGN PATENT DOCUMENTS

| CN | 108658908 A | 10/2018 |
| EP | 3653613 A1 | 5/2020 |
| WO | WO 2007-118964 A1 | 10/2007 |
| WO | WO 2015-095780 A1 | 6/2015 |

OTHER PUBLICATIONS

Stoll, R. et al. "Chalcone Derivatives Antagonize Interactions between the Human Oncoprotein MDM2 and p53." Biochemistry, 40(2):336-344. (2000).
Babu, V.H. et al. "Synthesis and Biological Evaluation of some Novel Pyrazolines." Indian Journal of Pharmaceutical Sciences, 69(3):470-473. (2007).
Suthakaran, R. et al. "Synthesis. Antiinflammatory. Antioxidant and Antibacterial Activities of 7-Methoxy Benzofuran Pyrazoline Derivatives." Asian Journal of Chemistry, 19(5):3353-3362. (2007).
Kamal, A. et al. "Synthesis and Anticancer Activity of 4β-alkylamidocalcone and 4β-cinnamido Linked Podophyllotoxins as Apoptotic Inducing Agents." European Journal of Medicinal Chemistry, 47:530-545. (2011).
International Search Report (ISR) for PCT/CN2018/115615; I.A. fd Nov. 11, 2018, dated Jan. 18, 2019 from the State Intellectual Property Office of the P.R. China, Beijing, China.
International Preliminary Report on Patentability (IPRP), Chapter I of the Patent Cooperation Treaty, including the Written Opinion for PCT/CN2018/115615; I.A. fd Nov. 11, 2018, Jun. 2, 2020, by the International Bureau of WIPO, Geneva, Switzerland.
Office action and search report for Chinese Patent Application No. 201880063551.9, dated Mar. 26, 2021, The State Intellectual Property Office of People's Republic of China, Beijing City, China.
The extended European search report, including the supplementary European search report and the European search opinion, for European Patent Application No. 18884390.8, dated Jul. 1, 2021, European Patent Office, Munich, Germany (10 pages).

*Primary Examiner* — Samantha L Shterengarts
(74) *Attorney, Agent, or Firm* — Sterne, Kessler, Goldstein & Fox P.L.L.C.

(57) ABSTRACT

The invention relates to an aromatic compound, pharmaceutical composition comprising the same, and a method for preparing the compound and an intermediate thereof. The invention also relates to use of the compound for the manufacture of a medicament for the prevention or treatment of a PPAR-related disease.

32 Claims, No Drawings

AROMATIC COMPOUND, PHARMACEUTICAL COMPOSITION AND USE THEREOF

FIELD OF THE INVENTION

The present invention relates to an aromatic compound, and a method for preparing the compound and intermediate thereof. The present invention also relates to use of the compound for the manufacture of a medicament for the prevention or treatment of a PPAR (peroxisome proliferator activated receptor)-related disease or condition.

BACKGROUND OF THE INVENTION

Non-alcoholic fatty liver disease (NAFLD) is a clinical pathological syndrome, which has the same liver histological changes as alcoholic liver disease but without the history of excessive drinking, and includes simple fatty liver (SFL), non-alcoholic steatohepatitis (NASH) and SFL- or NASH-related cirrhosis, wherein NASH is an important intermediate stage of NAFLD progression. The prevalence rate of NAFLD/NASH gradually increases with the high incidence of insulin resistance and related multiple metabolic syndrome. Today, NAFLD has become one of the most common liver diseases in developed countries and regions. For the general adults in the United States, the prevalence rate of NAFLD is 10-40% (with an average of 20%) and that of NASH is 2-5% (with an average of 3%) respectively. This is especially true for special populations with obesity, diabetes and chronic elevation of serum alanine aminotransferase (ALT), and NAFLD appears at a low-aging trend.

Non-alcoholic fatty liver disease can not only directly cause decompensated cirrhosis, hepatocellular carcinoma and recurrence of hepatocellular carcinoma after liver transplantation, but also affect the progress of other chronic liver diseases. In addition, it relates to the pathogenesis of type 2 diabetes and atherosclerosis. Metabolic syndrome-related malignant tumors, atherosclerotic cardiovascular and cerebrovascular diseases and liver cirrhosis are important factors affecting the living quality and life expectancy of patients with non-alcoholic fatty liver disease. At present, NASH has become one of the important prophase lesions of cirrhosis second only to chronic viral hepatitis and alcoholic liver disease, and it is also a common cause of serum transaminase abnormalities in healthy population in physical examination. Effective prevention and treatment of NASH is expected to prevent the progression of chronic liver disease and to reduce the occurrence of liver cirrhosis and liver disease-related disability and death. Non-alcoholic fatty liver disease is a new challenge in the field of contemporary medicine.

It is of important clinical significance to develop drugs for the treatment of non-alcoholic fatty liver-related diseases.

As a member of the intranuclear receptor transcription factor superfamily, PPAR plays a key role in regulating metabolic homeostasis, inflammation, cell growth and differentiation. For type II diabetes, PPAR agonists are used as hypolipidemic drugs and oral hypoglycemic drugs. In recent years, researches show that these agonists have liver protection function. PPAR α is highly expressed in hepatocytes and mainly plays a role in regulating fatty acid transport and β-oxidation. In addition, PPAR α can regulate the gluconeogenesis and inflammatory response. Likewise, PPAR δ can regulate glucose utilization and lipoprotein metabolism in liver, and has significant anti-inflammatory activity. Based on the study of PPAR α and PPAR δ functions, it is possible for PPAR α&δ dual agonists to solve various biological problems involved in the pathogenesis of NASH, or more extensive metabolic and cardiovascular problems.

Content of the Invention

The invention provides a compound having a 2-phenoxy-acetic acid structure and acting as a PPAR α&δ dual agonist, which has excellent dual agonist activity to PPAR α&δ, improved physicochemical properties (e.g., solubility, physical and/or chemical stability), improved pharmacokinetic properties (e.g., improved bioavailability, appropriate half-life and duration of action), improved safety (lower toxicity and/or fewer side effects, wider therapeutic window), and the like.

One aspect of the invention provides a compound or a pharmaceutically acceptable salt, ester, stereoisomer, tautomer, polymorph, solvate, N-oxide, isotope-labeled compound, metabolite or prodrug thereof, wherein the compound has the structure of Formula (I):

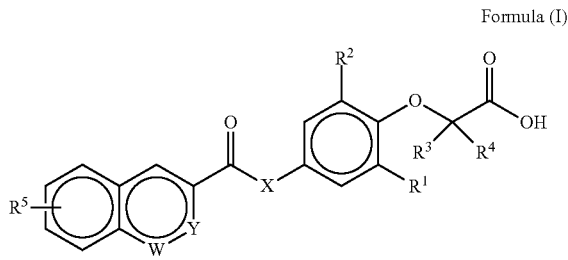

Formula (I)

wherein:

$R^1$, $R^2$, $R^3$ and $R^4$ are each independently selected from the group consisting of H, halogen, —OH, —SH, cyano, $C_{1-6}$ alkyl, $C_{3-6}$ cycloalkyl, halogenated $C_{1-6}$ alkyl, $C_{2-5}$ alkenyl, —O—[($C_{1-6}$ alkylene)-O]$_n$—($C_{1-6}$ alkyl), —S—($C_{1-6}$ alkyl), —NH$_2$, —NH—($C_{1-6}$ alkyl), —N ($C_{1-6}$ alkyl)$_2$ and 3-10 membered heterocyclyl; or, $R^3$ and $R^4$ are connected to form $C_{3-6}$ cycloalkyl or 3-10 membered heterocyclyl; X is selected from ethylene, vinylene and $C_{3-6}$ cycloalkylene; optionally, the ethylene, vinylene and $C_{3-6}$ cycloalkylene are each independently substituted by one or more substituents selected from the group consisting of halogen, $C_{1-6}$ alkyl, halogenated $C_{1-6}$ alkyl, $C_{3-6}$ cycloalkyl, —O—($C_{1-6}$ alkyl), 3-10 membered heterocyclyl, $C_{6-14}$ aryl and 5-14 membered heteroaryl;

Y is selected from a bond, N or C—$R^6$;

W is selected from N, S and C;

$R^5$ and $R^6$ are each independently selected from the group consisting of H, halogen, —OH, —SH, cyano, nitro, $C_{1-6}$ alkyl, $C_{3-6}$ cycloalkyl, $C_{2-5}$ alkenyl, —S(O)$_m$—($C_{1-6}$ alkyl), —O—[($C_{1-6}$ alkylene)-O]$_n$—($C_{1-6}$ alkyl), —O—($C_{3-6}$ cycloalkyl), —O-(3-6 membered heterocyclyl), —S(O)$_m$—($C_{3-6}$ cycloalkyl), —S(O)$_m$-(3-10 membered heterocyclyl), —NH$_2$, —NH—($C_{1-6}$ alkyl), —N($C_{1-6}$ alkyl)$_2$, 3-10 membered heterocyclyl, $C_{6-14}$ aryl and 5-14 membered heteroaryl; optionally, the $C_{1-6}$ alkyl, cycloalkyl, heterocyclyl, $C_{6-14}$ aryl, and 5-14 membered heteroaryl are each independently substituted by one or more substituents selected from the group consisting of halogen, —OH, —OC$_{1-6}$ alkyl, halogenated $C_{1-6}$ alkyl, —O-halogenated $C_{1-6}$ alkyl, —SH, —SC$_{1-6}$ alkyl, —NH$_2$, —NH—($C_{1-6}$ alkyl), and —N($C_{1-6}$ alkyl)$_2$;

m is any integer from 0 to 2, and n is any integer from 0 to 10.

Another aspect of the invention provides a pharmaceutical composition, comprising a prophylactically or therapeutically effective amount of the compound of the invention or a pharmaceutically acceptable salt, ester, stereoisomer, tautomer, polymorph, solvate, N-oxide, isotope-labeled compound, metabolite or prodrug thereof, and one or more pharmaceutically acceptable carriers. The pharmaceutical composition is preferably a solid preparation, a semi-solid preparation, a liquid preparation or a gaseous preparation.

Another aspect of the application provides use of the compound or the pharmaceutically acceptable salt, ester, stereoisomer, tautomer, polymorph, solvate, N-oxide, isotope-labeled compound, metabolite, prodrug or mixture thereof, the pharmaceutical composition, or the kit product thereof for the manufacture of a medicament for the prevention or treatment of a PPAR-related disease or condition.

Another aspect of the application provides the compound or the pharmaceutically acceptable salt, ester, stereoisomer, tautomer, polymorph, solvate, N-oxide, isotope-labeled compound, metabolite, prodrug or mixture thereof, pharmaceutical composition, or kit product thereof, for use in the prevention or treatment of a PPAR-related disease or condition.

Another aspect of the application provides a method for preventing or treating a PPAR-related disease or condition, comprising administering to a subject in need thereof an effective amount of the compound or the pharmaceutically acceptable salt, ester, stereoisomer, tautomer, polymorph, solvate, N-oxide, isotope-labeled compound, metabolite, prodrug or mixture thereof, the pharmaceutical composition, or the kit product.

Another aspect of the invention provides use of the compound of the invention or the pharmaceutically acceptable salt, ester, stereoisomer, tautomer, polymorph, solvate, N-oxide, isotope-labeled compound, metabolite or prodrug thereof or the pharmaceutical composition of the invention in the manufacture of a reagent for the activation of PPAR in cells.

Another aspect of the invention provides the compound of the invention or the pharmaceutically acceptable salt, ester, stereoisomer, tautomer, polymorph, solvate, N-oxide, isotope-labeled compound, metabolite or prodrug thereof or the pharmaceutical composition of the invention, for use in the activation of PPAR in cells.

Another aspect of the invention provides a method for activating PPAR in a cell, comprising a step of contacting the cell with an effective amount of the compound of the invention or the pharmaceutically acceptable salt, ester, stereoisomer, tautomer, polymorph, solvate, N-oxide, isotope-labeled compound, metabolite or prodrug thereof or the pharmaceutical composition of the invention.

Definition

Unless otherwise defined below, all technical and scientific terms used herein are intended to have the same meanings as commonly understood by those skilled in the art.

The technologies used herein are intended to refer to these commonly understood in the art, including variations apparent to those skilled in the art and their equivalent alternatives. The following terms, which are believed to be well understood by those skilled in the art, are still set forth as follows to better explain the invention.

As used herein, the term "alkylene" refers to a saturated bivalent hydrocarbon radical, preferably a saturated bivalent hydrocarbon radical having 1, 2, 3, 4, 5 or 6 carbon atoms, such as methylene, ethylene, propylene or butylene.

As used herein, the term "alkyl" is defined as a linear or branched saturated aliphatic hydrocarbon radical. In some embodiments, the alkyl has 1 to 12 carbon atoms, for example 1 to 6 carbon atoms. For example, as used herein, the term "$C_{1-6}$ alkyl" refers to a linear or branched aliphatic hydrocarbon radical having 1 to 6 carbon atoms (e.g., methyl, ethyl, n-propyl, isopropyl, n-butyl, isobutyl, sec-butyl, tert-butyl, n-pentyl, iso-pentyl, neopentyl, or n-hexyl), which is optionally substituted with one or more (e.g., 1 to 3) suitable substituents (e.g., halogen) (the group is referred to as "haloalkyl" herein) (e.g., $CH_2F$, $CHF_2$, $CF_3$, $CCl_3$, $C_2F_5$, $C_2Cl_5$, $CH_2CF_3$, $CH_2Cl$, or —$CH_2CH_2CF_3$). The term "$C_{1-4}$ alkyl" refers to a linear or branched aliphatic hydrocarbon radical having 1 to 4 carbon atoms (i.e., methyl, ethyl, n-propyl, isopropyl, n-butyl, isobutyl, sec-butyl or tert-butyl).

As used herein, the term "alkenyl" refers to a linear or branched monovalent hydrocarbon radical having one double bond and, for example, 2-5 carbon atoms ("$C_{2-5}$ alkenyl"). The alkenyl is, for example, vinyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

As used herein, the term "alkenylene" refers to a linear or branched divalent carbon chain having one or more carbon-carbon double bonds (—CR═CR'—, where R and R' are each independently hydrogen or other substituents). Examples of alkenylene include vinylene, propylene, and the like. When the compound of the invention has an alkenylene, the compound may exist in the form of pure E (entgegen), pure Z (zusammen) form, or any mixture thereof.

As used herein, the term "cycloalkyl" or "cyclic alkyl" refers to saturated monocyclic or polycyclic (e.g bicyclic) hydrocarbon ring radical (e.g., monocyclic, including cyclopropyl, cyclobutyl, cyclopentyl, cyclohexyl, cycloheptyl, cyclooctyl, and cyclononyl, or bicyclic, including spiro, fused, or bridged systems (e.g. bicyclic [1.1.1] pentyl, bicyclic [2.2.1] heptyl, bicyclic [3.2.1] octyl, or bicyclic [5.2.0] nonyl, decalinyl), which are optionally substituted with one or more (e.g 1 to 3) suitable substituents. The cycloalkyl has 3 to 15 carbon atoms. For example, the term "$C_{3-6}$ cycloalkyl" refers to a saturated monocyclic or polycyclic (e.g. bicyclic) hydrocarbon ring radical (e.g., cyclopropyl, cyclobutyl, cyclopentyl, or cyclohexyl) having 3 to 6 ring-forming carbon atoms, which is optionally substituted with one or more (e.g. 1 to 3) suitable substituents, such as methyl substituted cyclopropyl.

As used herein, the terms "heterocyclyl" and "heterocyclic hydrocarbon radical" refer to a saturated (i.e., heterocycloalkyl) or partially unsaturated (i.e., having one or more double bonds and/or triple bonds within a ring) cyclic group having, for example, 3-10 (suitably 3-8, more suitably 3-6) ring atoms, wherein at least one ring atom is a heteroatom selected from N, O, and S and the remaining ring atoms are C. For example, "3-10 membered heterocyclyl" is a saturated or partially unsaturated heterocyclyl having 2-9 (e.g., 2, 3, 4, 5, 6, 7, 8, or 9) ring carbon atoms and one or more (e.g., 1, 2, 3, or 4) heteroatoms independently selected from N, O, and S. Examples of heterocyclyl include, but are not limited to, oxiranyl, aziridinyl, azetidinyl, oxetanyl, tetrahydrofuryl, dioxolinyl, pyrrolidinyl, pyrrolidonyl, imidazolidinyl, pyrazolidyl, pyrrolinyl, tetrahydropyranyl, piperidinyl, morpholinyl, dithianyl, thiomorpholinyl, piperazinyl, and trithianyl. The heterocyclyl may be optionally substituted with one or more (e.g., 1, 2, 3 or 4) suitable substituents.

As use herein, the term "heterocyclylene" refers to a saturated (i.e., heterocycloalkylene) or partially unsaturate (i.e., having one or more double bonds and/or triple bonds within a ring) divalent cyclic group having, for example, 3-10 (suitably 3-8, more suitably 3-6) ring atoms, wherein at least one ring atom is heteroatom selected from N, O, and S and the remaining ring atoms are C. For example, "3-10 membered heterocyclylene" is a saturated or partially unsaturated heterocyclylene having 2-9 (e.g., 2, 3, 4, 5, 6, 7, 8, or 9) ring carbon atoms and one or more (e.g., 1, 2, 3, or 4) heteroatoms independently selected from N, O, and S. Examples of the heterocyclylene include, but are not limited to, oxiranylene, aziridinylene, azetidinylene, oxetanylene, tetrahydrofurylene, dioxolinylene, pyrrolidinylene, pyrrolidonylene, imidazolidinylene, pyrazolidinylene, pyrrolinylene, tetrahydropyranylene, piperidinylene, morpholinylene, dithianylene, thiomorpholinylene, piperazinylene, or trithianylene. The heterocyclylene may be optionally substituted with one or more (e.g., 1, 2, 3 or 4) suitable substituents.

As used herein, the term "aryl(ene)" refers to an all-carbon monocyclic or fused ring polycyclic aromatic group having a conjugated π electron system. For example, as used herein, the term "$C_{6-14}$ aryl(ene)" refers to an aromatic group containing 6 to 14 carbon atoms, such as phenyl(ene) or naphthyl(ene). The aryl(ene) is optionally substituted with one or more (e.g., 1 to 3) suitable substituents (e.g., halogen, —OH, —CN, —$NO_2$ and $C_{1-6}$ alkyl).

As used herein, the term "heteroaryl(ene)" refers to a monocyclic or polycyclic aromatic ring having, for example, 5, 6, 8, 9, 10, 11, 12, 13 or 14 ring atoms, in particular 1, 2, 3, 4, 5, 6, 9 or 10 carbon atoms, and containing at least one heteroatom (the heteroatom is, for example, oxygen, nitrogen or sulfur) that can be same or different, and may additionally be benzofused in each case. In particular, heteroaryl(ene) is selected from thienyl(ene), furyl(ene), pyrrolyl(ene), oxazolyl(ene), thiazolyl(ene), imidazolyl(ene), pyrazolyl(ene), isoxazolyl(ene), isothiazolyl(ene), oxadiazolyl(ene), triazolyl(ene), thiadiazolyl(ene), and benzo derivatives thereof; or pyridyl(ene), pyridazinyl(ene), pyrimidinyl(ene), pyrazinyl(ene), triazinyl(ene), and benzo derivatives thereof.

As used herein, the term "halogen" includes F, Cl, Br or I.

The term "substitution" refers to the selective substitution of one or more (e.g., 1, 2, 3, or 4) hydrogens on the designated atom with the designated group, provided that the normal valence of the designated atom in the current case is not exceeded and the substitution will result in a stable compound. The combination of substituents and/or variables is allowed only when such a combination can form a stable compound.

If the substituent is described as "optionally substituted by . . . ", the substituent may (1) be unsubstituted or (2) be substituted. If the carbon of the substituent is described as being optionally substituted by one or more the substituents in the list thereof, one or more hydrogens (to the extent of any hydrogen present) on the carbon may be individually and/or collectively replaced with independently selected optional substituents. If the nitrogen of the substituent is described as being optionally substituted by one or more substituents in the list thereof, one or more hydrogens (to the extent of any hydrogen present) on the nitrogen may each be replaced with an independently selected optional substituent.

If the substituent is described as being "independently selected from" a set of groups, each substituent is selected independently of the other. Therefore, each substituent may be the same as or different from another (other) substituent.

As used herein, the term "one or more" refers to one or more than one (e.g. 2, 3, 4, 5 or 10) under reasonable conditions.

Unless otherwise specified, the bonding site of the substituent may be any suitable position of the substituent as used herein.

When the bond of a substituent is depicted as passing through a bond connecting two atoms in a ring, such a substituent may be bonded to any ring-forming atom in the substitutable ring.

The invention further includes all pharmaceutically acceptable isotope-labeled compounds, which are the same as the compounds of the invention, except that one or more atoms are replaced by atoms having the same atomic number but different atomic mass or mass number from that prevailing in nature. Examples of isotopes suitably encompassed in the compounds of the invention include, but are not limited to, isotopes of hydrogen (e.g., deuterium ($^2H$) and tritium ($^3H$)); isotopes of carbon (e.g. $^{11}C$, $^{13}C$ and $^{14}C$) isotopes of chlorine (e.g. $^{36}Cl$); isotopes of fluorine (e.g. $^{18}F$); isotopes of iodine (e.g. $^{123}I$ and $^{125}I$); isotopes of nitrogen (e.g. $^{13}N$ and $^{15}N$); isotopes of oxygen (e.g. $^{15}O$, $^{17}O$ and $^{18}O$); isotopes of phosphorus (e.g. $^{32}P$); and isotopes of sulfur (e.g. $^{35}S$).

The term "stereoisomer" refers to an isomer formed by at least one asymmetric center. For a compound having one or more (e.g., one, two, three, or four) asymmetric centers, a racemate, a single enantiomer, diastereomers and a single diastereomer may be created. Particular molecule may exist as geometric isomers (cis/trans). Similarly, the compound of the invention may exist as mixtures (often referred to as tautomers) in the form of two or more different structures in rapid equilibrium. Representative examples of tautomers include ketone-enol tautomers, phenol-ketone tautomers, nitroso-oxime tautomers, imine-enamine tautomers, and the like. It should be understood that the scope of the application covers all such isomers in any ratio (e.g., 60%, 65%, 70%, 75%, 80%, 85%, 90%, 95%, 96%, 97%, 98% and 99%) or mixtures thereof.

In the context, the carbon-carbon bond of the compound of the invention can be depicted by solid lines ( ——— ), wedges ( ▬▬▬ ), or dashed bond ( ⸽⸽⸽⸽ ). For the bond bonding to an asymmetric carbon atom, when it is depicted as a solid line, it is for the purpose of encompassing any possible stereoisomers (e.g., a specific enantiomer, or a racemic mixture) at that carbon atom; when it is depicted as a wedge or a dashed bond, it is for the purpose of indicating the stereoisomer as shown. For a racemic mixture, the wedge and dashed bond are used to define relative stereochemistry rather than absolute stereochemistry. Unless otherwise specified, the compound of the invention is intended to be present as a form of stereoisomer (including a cis- or trans-isomers, an optical isomer (e.g., R or S enantiomer), a diastereomer, a geometric isomer, a rotamer, a conformer, an atropisomer, or a mixture thereof). The compound of the invention may exhibit more than one type of isomerism and is composed of the mixtures thereof (e.g., a racemic mixture or a pair of diastereoisomers).

The invention covers all possible crystalline forms or polymorphs of the compound of the invention, which may be a single polymorph or a mixture of more than one polymorphs at any ratios.

It should also be understood that certain compounds of the invention may exist in free state for the treatment purpose or, where appropriate, as a pharmaceutically acceptable derivative thereof. In the invention, the pharmaceutically acceptable derivative includes, but is not limited to, a pharmaceutically acceptable salt, ester, solvate, N-oxide, metabolite or prodrug, which, after being administered to a patient in need thereof, can directly or indirectly provide the compound of the invention or a metabolite or residue thereof. Therefore, "the compound of the invention" mentioned herein is also intended to cover various derivative forms of the compound.

The pharmaceutically acceptable salt of the compound of the invention comprises acid addition salt and base addition salt thereof.

Suitable acid addition salt is formed by acids that form the pharmaceutically acceptable salt. Examples include hydrochloride, acetate, aspartate, benzoate, bicarbonate/carbonate, glucoheptonate, gluconate, nitrate, orotate, palmitate, and other similar salts.

Suitable base addition salt is formed by bases that form the pharmaceutically acceptable salt. Examples include aluminum salts, arginine salts, choline salts, magnesium salts, and other similar salts.

For a summary of suitable salts, see Stahl and Wermuth's "Handbook of Pharmaceutical Salts: Properties, Selection, and Use" (Wiley-VCH, 2002). The method for preparing a pharmaceutically acceptable salt of the compound of the invention is known to those skilled in the art.

As used herein, the term "ester" refers to an ester derived from various compounds of the general formula of the instant application, including a physiologically hydrolyzable ester (the compound of the invention that can be hydrolyzed under physiological conditions to release free acid, or in alcohol forms). The compound of the invention itself may also be an ester.

The compound of the invention may exist as a solvate (preferably hydrate), wherein the compound of the invention comprises a polar solvent as a structural element of the crystal lattice of the compound, in particular, for example, water, methanol or ethanol.

The amount of polar solvent, especially water, may exist in stoichiometric or non-stoichiometric ratios.

Those skilled in the art will appreciate that not all nitrogen-containing heterocycles can form N-oxides because nitrogen requires available lone-pair electron to be oxidized to N-oxides; those skilled in the art will select the nitrogen-containing heterocycles capable of forming N-oxides. Those skilled in the art will also recognize that tertiary amines can form N-oxides. The synthetic methods for N-oxides for preparing heterocycles and tertiary amines are well known to those skilled in the art, and include the oxidation of heterocycles and tertiary amines by peroxyacids (e.g. peracetic acid and m-chloroperoxybenzoic acid (MCPBA)), hydrogen peroxide and alkyl hydroperoxides (e.g. tert-butyl hydroperoxide), sodium perborate and dioxirane (e.g. dimethyl dioxane). These methods for preparing N-oxides have been extensively described and summarized in the literature, see e.g. T. L. Gilchrist, Comprehensive Organic Synthesis, vol. 7, pp 748-750; A. R. Katritzky and A. J. Boulton, Eds., Academic Press; G. W. H. Cheeseman and E. S. G. Werstiuk, Advances in Heterocyclic Chemistry, vol. 22, pp 390-392, A. R. Katritzky and A. J. Boulton, Eds., Academic Press.

The metabolite of the compound of the invention, i.e., a substance formed in vivo when the compound of the invention are administered, is also included within the scope of the invention. Such a product may be produced, for example, by oxidation, reduction, hydrolysis, amidation, deamidation, esterification and enzymolysis of the administered compound. Therefore, the invention includes a metabolite of the compound of the invention, including a compound prepared by contacting the compound of the invention with a mammal for a sufficient amount of time to produce the metabolite thereof.

The invention further includes, within its scope, a prodrug of the compound of the invention, which is certain derivative of the compound of the invention that itself may have little or no pharmacological activity, and may be converted into the compound of the invention having the desired activity by, for example, hydrolytic cleavage when administered into or on the body. Usually such a prodrug will be a functional derivative of the compound that is readily converted into a desired therapeutically active compound in vivo. To obtain additional information on the use of prodrug, see "Pro-drugs as Novel Delivery Systems", vol. 14, ACS Symposium Series (T. Higuchi and V. Stella). The prodrug of the invention can be prepared, for example, by replacing the appropriate functional groups in the compound of the invention with certain moieties known to those skilled in the art as "pro-moiety" (e.g., "Design of Prodrugs", H. Bundgaard (Elsevier, 1985)).

The invention further covers the compound of the invention containing protecting groups. In any process of preparing the compound of the invention, it may be necessary and/or desirable to protect a sensitive group or a reactive group on any relevant molecule, thereby forming a chemically protected compound of the invention. This can be achieved by conventional protecting groups such as those described in T. W. Greene & P. G. M. Wuts, Protective Groups in Organic Synthesis, John Wiley & Sons, 1991, which are incorporated herein by reference. Based on the methods known in the art, the protecting group can be removed at an appropriate subsequent stage.

The term "about" refers to the stated value within the range of ±10%, preferably within the range of ±5%, more preferably within the range of ±2%.

Specific Mode for Carrying Out the Invention

Compound

In some embodiments, the invention provides a compound or a pharmaceutically acceptable salt, ester, stereoisomer, tautomer, polymorph, solvate, N-oxide, isotope-labeled compound, metabolite or prodrug thereof, wherein the compound has the structure of Formula (I):

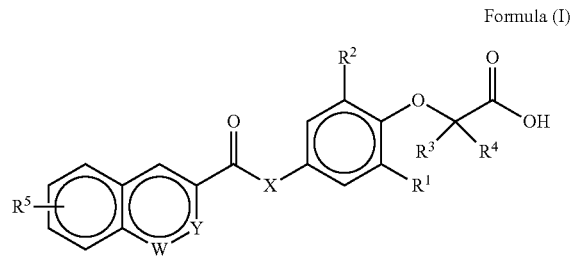

Formula (I)

$R^1$, $R^2$, $R^3$ and $R^4$ are each independently selected from the group consisting of H, halogen, —OH, —SH, cyano, $C_{1-6}$ alkyl, $C_{3-6}$ cycloalkyl, halogenated $C_{1-6}$ alkyl, $C_{2-5}$ alkenyl, —O—[(C$_{1-6}$ alkylene)-O]$_n$—(C$_{1-6}$ alkyl), —S—(C$_{1-6}$ alkyl), —NH$_2$, —NH—(C$_{1-6}$ alkyl), —N (C$_{1-6}$ alkyl)$_2$ and 3-10 membered heterocyclyl; or, R$^3$ and R$^4$ are connected to form C$_{3-6}$ cycloalkyl or 3-10 membered heterocyclyl;

X is selected from ethylene, vinylene and C$_{3-6}$ cycloalkylene; optionally, the ethylene, vinylene and C$_{3-6}$ cycloalkylene are each independently substituted by one or more substituents selected from the group consisting of halogen, C$_{1-6}$ alkyl, halogenated C$_{1-6}$ alkyl, C$_{3-6}$ cycloalkyl, —O—(C$_{1-6}$ alkyl), 3-10 membered heterocyclyl, C$_{6-14}$ aryl and 5-14 membered heteroaryl;

Y is selected from a bond, N or C—R$^6$;

W is selected from N, S and C;

R$^5$ and R$^6$ are each independently selected from the group consisting of H, halogen, —OH, —SH, cyano, nitro, C$_{1-6}$ alkyl, C$_{3-6}$ cycloalkyl, C$_{2-5}$ alkenyl, —S(O)$_m$—(C$_{1-6}$ alkyl), —O—[(C$_{1-6}$ alkylene)-O]$_n$—(C$_{1-6}$ alkyl), —O—(C$_{3-6}$ cycloalkyl), —O-(3-6 membered heterocyclyl), —S(O)$_m$—(C$_{3-6}$ cycloalkyl), —S(O)$_m$-(3-10 membered heterocyclyl), —NH$_2$, —NH—(C$_{1-6}$ alkyl), —N(C$_{1-6}$ alkyl)$_2$, 3-10 membered heterocyclyl, C$_{6-14}$ aryl and 5-14 membered heteroaryl; optionally, the C$_{1-6}$ alkyl, cycloalkyl, heterocyclyl, C$_{6-14}$ aryl, and 5-14 membered heteroaryl are each independently substituted by one or more substituents selected from the group consisting of halogen, —OH, —OC$_{1-6}$ alkyl, halogenated C$_{1-6}$ alkyl, —O-halogenated C$_{1-6}$ alkyl, —SH, —SC$_{1-6}$ alkyl, —NH$_2$, —NH—(C$_{1-6}$ alkyl), and —N(C$_{1-6}$ alkyl)$_2$;

m is any integer from 0 to 2, and n is any integer from 0 to 10.

In a preferred embodiment, R$^1$, R$^2$, R$^3$ and R$^4$ are each independently selected from the group consisting of H, halogen, C$_{1-6}$ alkyl, halogenated C$_{1-6}$ alkyl, and —O—[(C$_{1-6}$ alkylene)-O]$_n$—(C$_{1-6}$ alkyl), wherein n is any integer from 0 to 10, preferably any integer from 0 to 5, more preferably 0, 1, 2 or 3; preferably, R$^1$ and R$^2$ are methyl. In a more preferred embodiment, R$^1$, R$^2$, R$^3$ and R$^4$ are methyl.

In a preferred embodiment, X is selected from ethylene, vinylene and cyclopropylene, each of which are independently and optionally substituted with one or two substituents selected from halogen and C$_{1-6}$ alkyl. In a preferred embodiment, X is vinylene.

In a preferred embodiment, Y is selected from a bond and C—R$^6$.

In a preferred embodiment, W is selected from N and S.

In a preferred embodiment, R$^5$ and R$^6$ are each independently selected from the group consisting of H, halogen, —OH, C$_{1-6}$ alkyl, C$_{3-6}$ cycloalkyl, —S(O)$_m$—(C$_{1-6}$ alkyl), —O—[(C$_{1-6}$ alkylene)-O]$_n$—(C$_{1-6}$ alkyl), —O—(C$_{3-6}$ cycloalkyl), —O-(3-6 membered heterocyclyl), —NH$_2$, —NH—(C$_{1-6}$ alkyl), —N(C$_{1-6}$ alkyl) 2 and 3-6 membered heterocyclyl, wherein the C$_{1-6}$ alkyl, C$_{3-6}$ cycloalkyl and 3-6 membered heterocyclyl are optionally substituted by one or more substituents selected from the group consisting of halogen, —OH, —OC$_{1-3}$ alkyl, —SH, —SC$_{1-3}$ alkyl, —NH$_2$, —NH—(C$_{1-3}$ alkyl) and —N(C$_{1-3}$ alkyl)$_2$; m is 0, 1 or 2, and n is 0, 1, 2, 3, 4 or 5. In a more preferred embodiment, R$^5$ and R$^6$ are each independently selected from H, F, Cl, —OH, C$_{1-3}$ alkyl, cyclopropyl, —S(O)$_m$—(C$_{1-3}$ alkyl), —O—[(C$_{1-2}$ alkylene)-O]$_n$—(C$_{1-3}$ alkyl), —O—(C$_{5-6}$ cycloalkyl), —O-(5-6 membered heterocyclyl), —NH$_2$, —NH—(C$_{1-6}$ alkyl), —N (C$_{1-3}$ alkyl)$_2$ and 5-6 membered heterocyclyl, wherein the C$_{1-3}$ alkyl, C$_{1-6}$ alkyl, cyclopropyl, C$_{5-6}$ cycloalkyl and 5-6 membered heterocyclyl are optionally substituted by 1 to 3 substituents selected from F, Cl, —OH and —OCH$_3$; m is 0, 1 or 2, and n is 0 or 1.

In a preferred embodiment, R$^5$ is selected from H and —O—[(C$_{1-2}$ alkylene)-O]$_n$—(C$_{1-3}$ alkyl), and n is 0, 1 or 2; preferably, n is 0.

In a preferred embodiment, R$^6$ is selected from H, F, Cl, —OH, C$_{1-3}$ alkyl, —SCH$_3$, —O—[(C$_{1-2}$ alkylene)-O]$_n$—(C$_{1-3}$ alkyl), —N(C$_{1-3}$ alkyl)$_2$ and 5-6 membered heterocyclyl, wherein the C$_{1-3}$ alkyl and 5-6 membered heterocyclyl are optionally substituted by 1 to 3 substituents selected from F, Cl, —OH and —OCH$_3$; n is 0, 1 or 2; preferably, n is 0 or 1.

In some embodiments, the compound of the invention has a structure of Formula (I)-1, Formula (I)-2 or Formula (I)-3:

Formula (I)-1

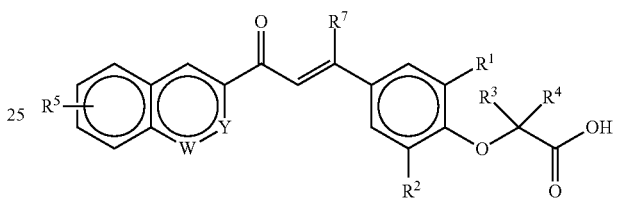

Formula (I)-2

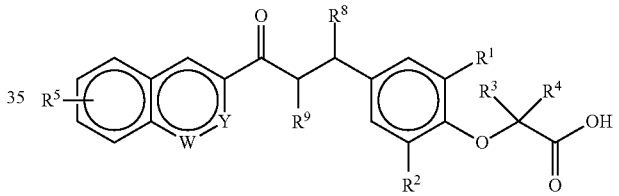

Formula (I)-3

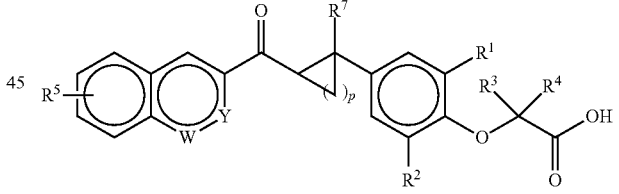

wherein W, Y, R$^1$, R$^2$, R$^3$, R$^4$, R$^5$ and R$^6$ are as defined in Formula (I);

R$^7$ is selected from the group consisting of H, halogen, C$_{1-6}$ alkyl, halogenated C$_{1-6}$ alkyl, C$_{3-6}$ cycloalkyl, —O—(C$_{1-6}$ alkyl), 3-10 membered heterocyclyl, C$_{6-14}$ aryl and 5-14 membered heteroaryl; preferably, R$^7$ is selected from H, halogen and C$_{1-6}$ alkyl; more preferably, R$^7$ is H or methyl;

R$^8$ and R$^9$ are each independently selected from the group consisting of H, halogen, C$_{1-6}$ alkyl, halogenated C$_{1-6}$ alkyl, C$_{3-6}$ cycloalkyl, —O—(C$_{1-6}$ alkyl), 3-10 membered heterocyclyl, C$_{6-14}$ aryl and 5-14 membered heteroaryl; preferably, R$^8$ and R$^9$ are each independently selected from H, halogen and C$_{1-6}$ alkyl; more preferably, R$^8$ and R$^9$ are H;

p=1 or 2; more preferably, p=1.

In some embodiments, the compound of the invention has a structure of Formula (II) or Formula (III):

Formula (II)

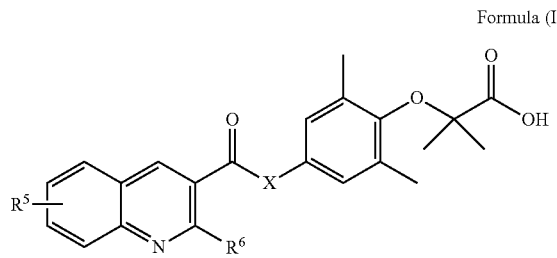

Formula (III)

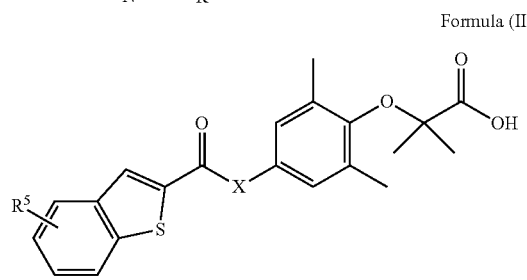

wherein, X, R⁵ and R⁶ are as defined in Formula (I).

In a preferred embodiment,

X is selected from vinylene and $C_{3-6}$ cycloalkylene;

$R^5$ is selected from H and —O—($C_{1-3}$ alkyl);

$R^6$ is selected from H, F, Cl, —OH, $C_{1-3}$ alkyl, —SCH₃, —O—[($C_{1-2}$ alkylene)-O]$_n$—($C_{1-3}$ alkyl), —N($C_{1-3}$ alkyl)₂ and 5-6 membered heterocycloalkyl, wherein the $C_{1-3}$ alkyl and 5-6 membered heterocycloalkyl are optionally substituted with 1-3 substituents selected from F, Cl, —OH and —OCH₃; n is 0, 1 or 2; preferably, n is 0 or 1.

In some embodiments, the compound of the invention has a structure of Formula (II-1) or Formula (III-1):

Formula (II-1)

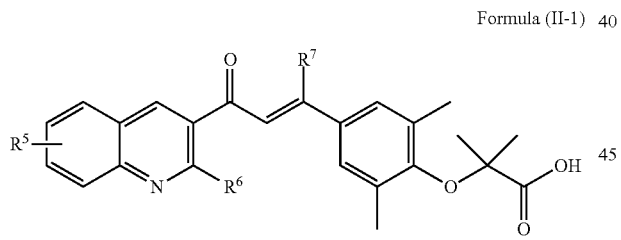

Formula (III-1)

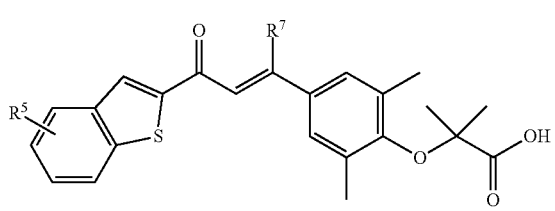

$R^7$ is selected from H, halogen, $C_{1-6}$ alkyl, halogenated $C_{1-6}$ alkyl, $C_{3-6}$ cycloalkyl, —O—($C_{1-6}$ alkyl), 3-10 membered heterocyclyl, $C_{6-14}$ aryl and 5-14 membered heteroaryl; preferably, $R^7$ is selected from H, halogen and $C_{1-6}$ alkyl; more preferably, $R^7$ is H or methyl.

In a preferred embodiment, $R^5$ is selected from H and —O—($C_{1-3}$ alkyl);

$R^6$ is selected from H, F, Cl, —OH, $C_{1-3}$ alkyl, —SCH₃, —O—[($C_{1-2}$ alkylene)-O]$_n$—($C_{1-3}$ alkyl), —N($C_{1-3}$ alkyl)₂ and 5-6 membered heterocycloalkyl, wherein the $C_{1-3}$ alkyl and 5-6 membered heterocycloalkyl are optionally substituted with 1-3 substituents selected from F, Cl, —OH and —OCH₃; n is 0, 1 or 2; preferably, n is 0 or 1;

$R^7$ is H or methyl.

In some embodiments, the compound of the invention has a structure of Formula (II-2) or Formula (III-2):

Formula (II-2)

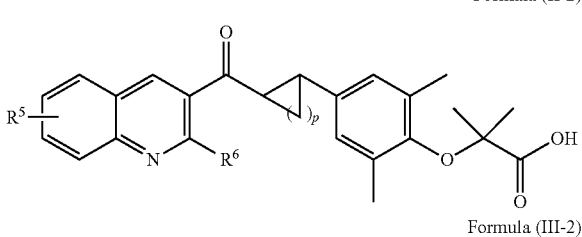

Formula (III-2)

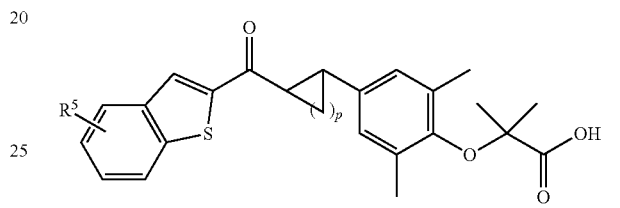

$R^5$ and $R^6$ are as defined in Formula (I); wherein, p is an integer from 1 to 4, preferably 1 or 2, more preferably 1.

In a preferred embodiment, $R^5$ is selected from H and —O—($C_{1-3}$ alkyl); $R^6$ is selected from the group consisting of H, F, Cl, —OH, $C_{1-3}$ alkyl, —SCH₃, —O—[($C_{1-2}$ alkylene)-O]$_n$—($C_{1-3}$ alkyl), —N ($C_{1-3}$ alkyl)₂ and 5-6 membered heterocycloalkyl, wherein the $C_{1-3}$ alkyl and 5-6 membered heterocycloalkyl are optionally substituted with 1-3 substituents selected from F, Cl, —OH and —OCH₃; n is 0, 1 or 2; preferably, n is 0 or 1;

p=1.

In some embodiments, the compound of the invention has a structure of Formula (II-3) or Formula (III-3):

Formula (II-3)

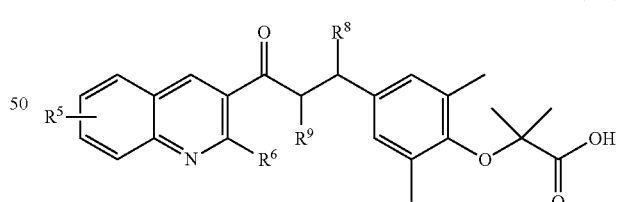

Formula (III-3)

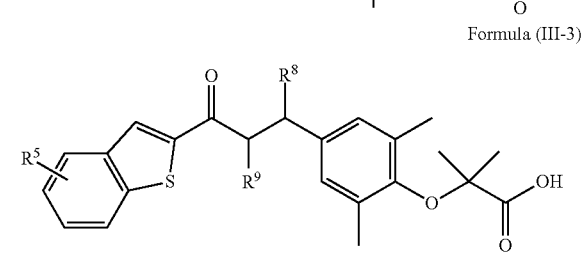

wherein, $R^8$ and $R^9$ are each independently selected from the group consisting of H, halogen, $C_{1-6}$ alkyl, halogenated $C_{1-6}$ alkyl, $C_{3-6}$ cycloalkyl, —O—($C_{1-6}$ alkyl), 3-10 membered heterocyclyl, $C_{6-14}$ aryl and 5-14 membered heteroaryl; preferably, $R^8$ and $R^9$ are each independently selected from H, halogen and $C_{1-6}$ alkyl; more preferably, $R^8$ and $R^9$ are H.

The invention covers the compounds obtained by any combination of various embodiments.

In a preferred embodiment, the invention provides a compound or a pharmaceutically acceptable salt, ester, stereoisomer, tautomer, polymorph, solvate, N-oxide, isotope-labeled compound, metabolite or prodrug thereof, wherein the compound is selected from:

TM1

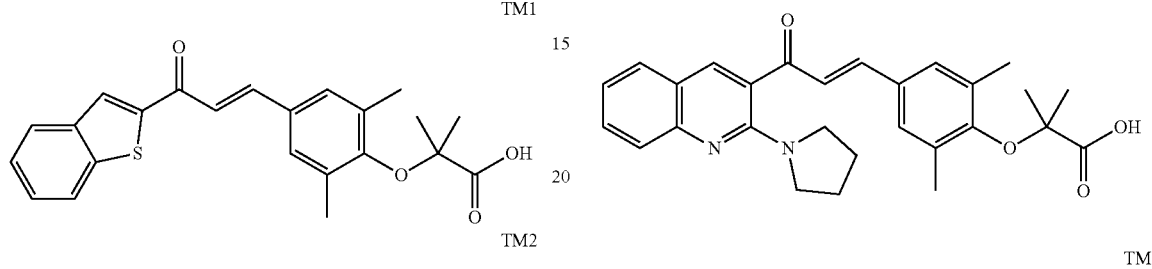

TM2

TM3

TM4

TM5

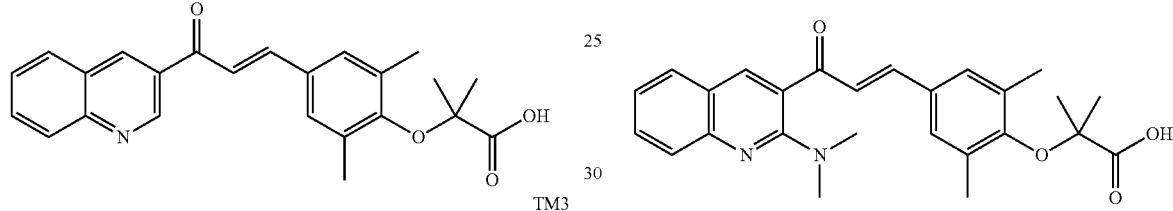

TM6

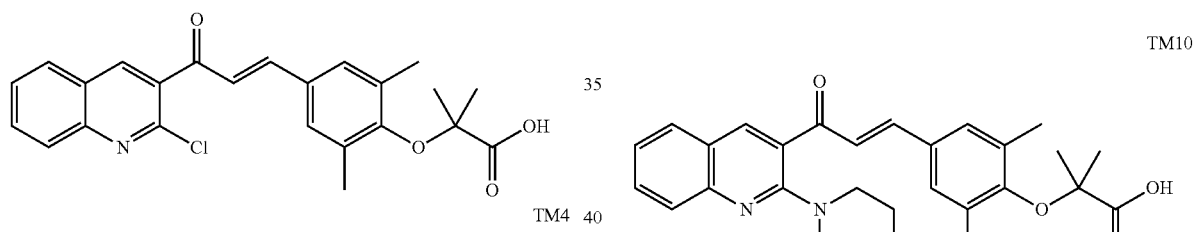

TM7

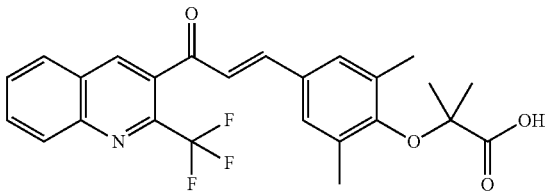

TM8

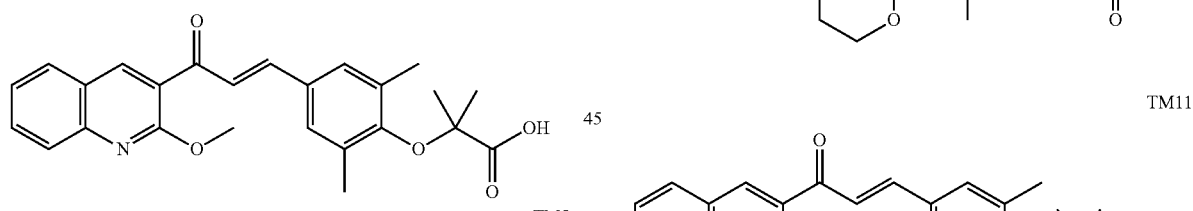

TM9

TM10

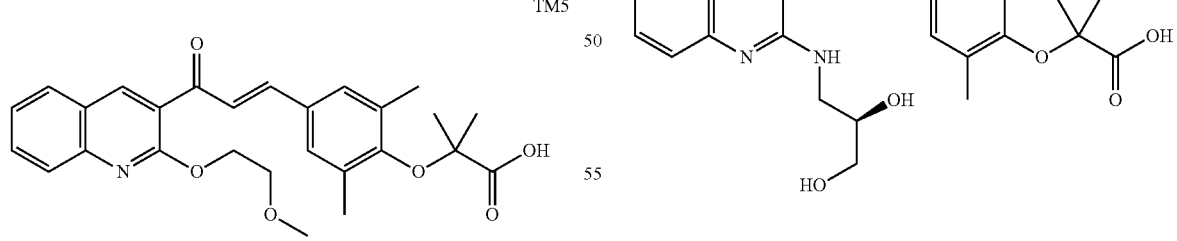

TM11

TM12

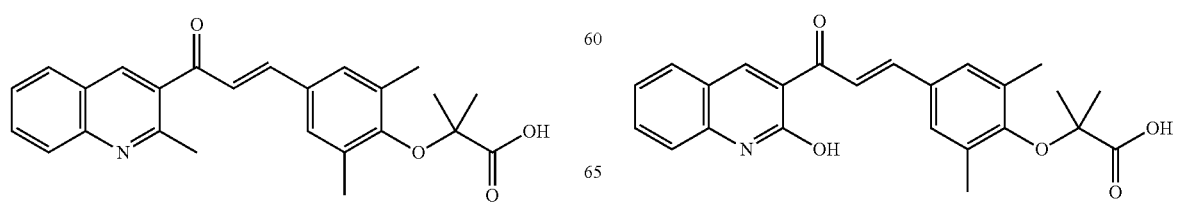

TM13
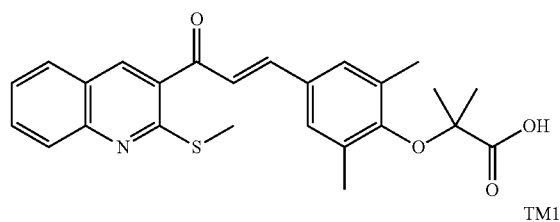
TM14
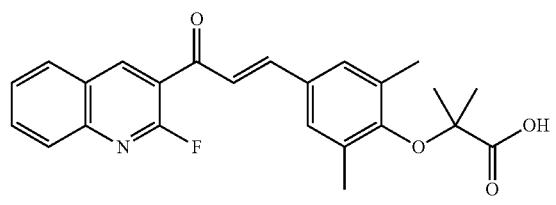
TM15
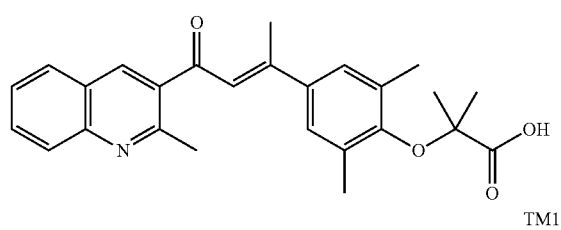
TM16
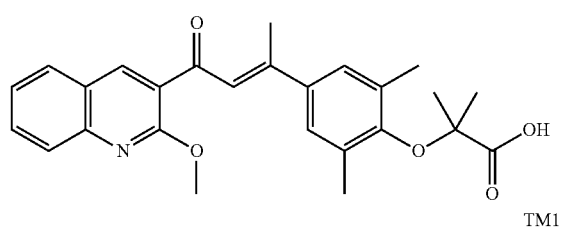
TM17
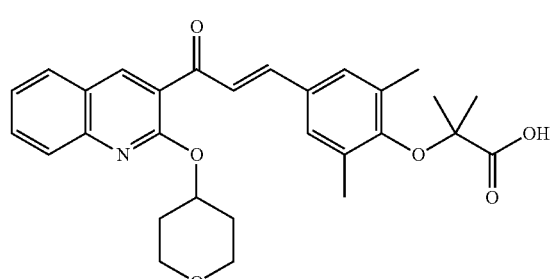
TM18
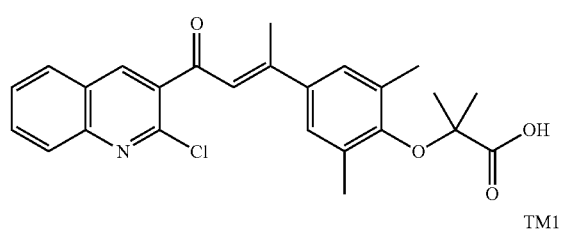
TM19
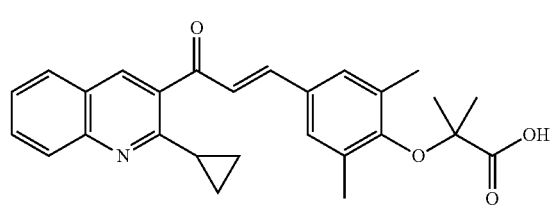
TM20
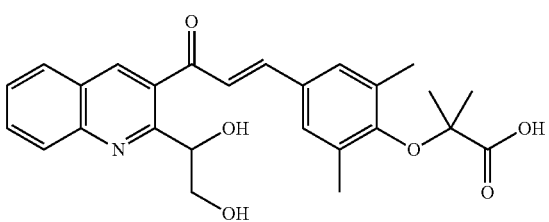
TM21
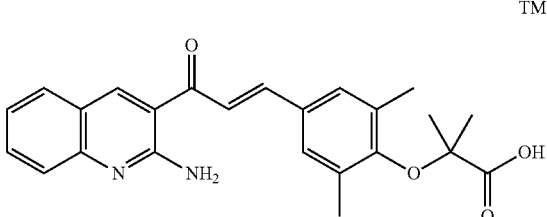
TM22
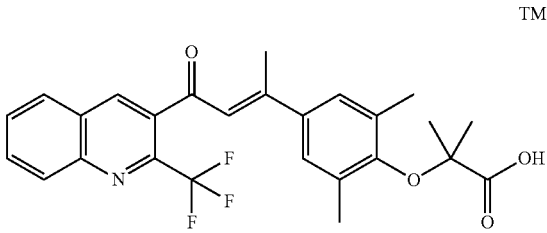
TM23
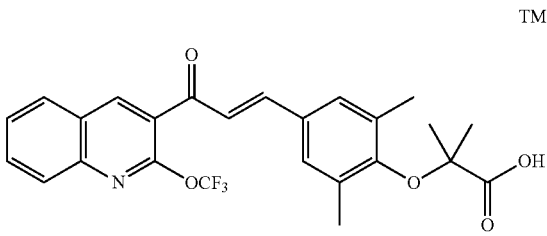
TM24
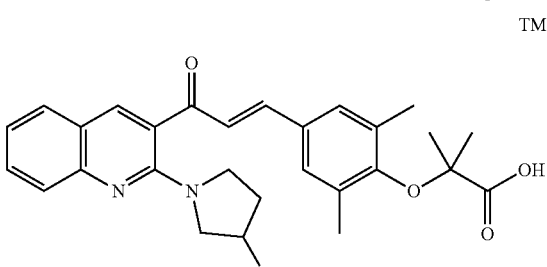
TM25
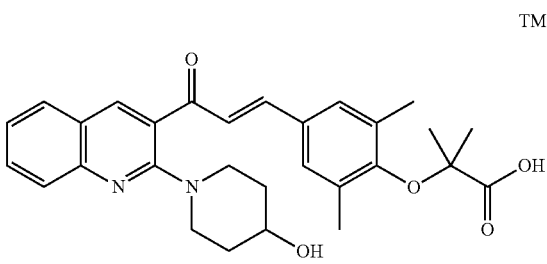
TM26
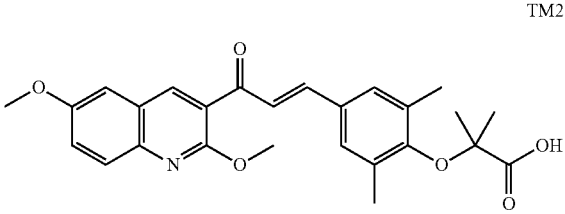

TM27
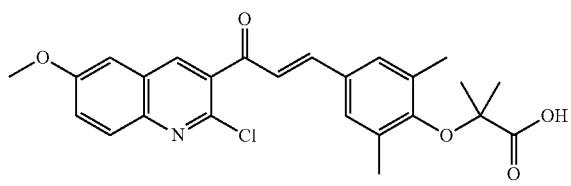
TM28
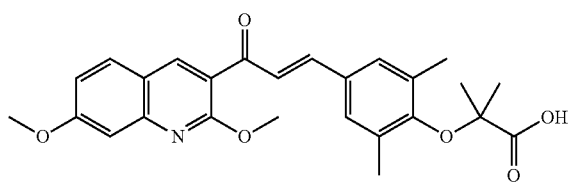
TM29
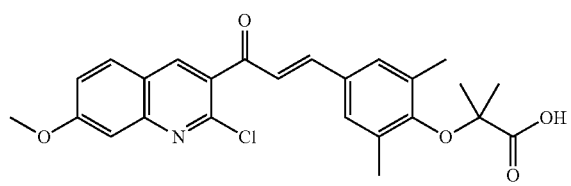
TM30
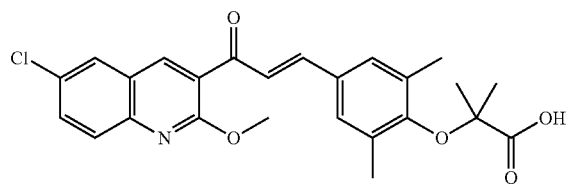
TM31
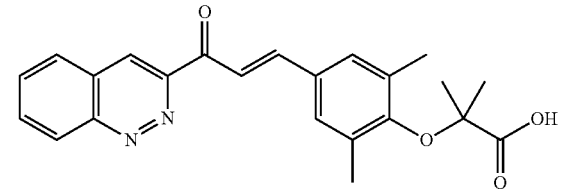
TM32
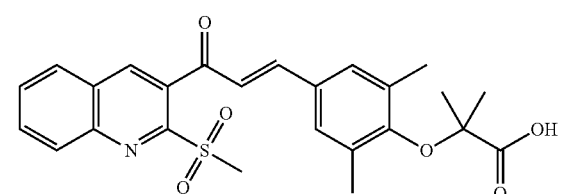
TM33
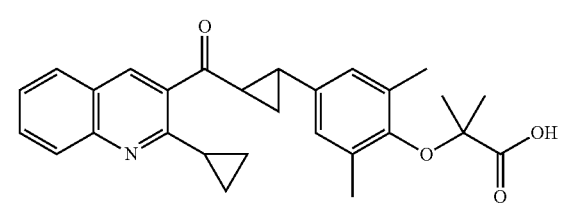
TM34
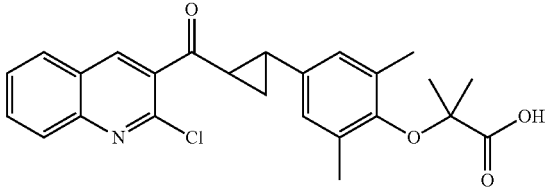
TM35
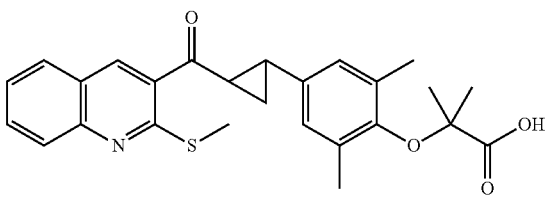
TM36
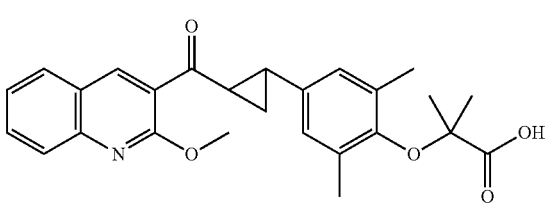
TM37
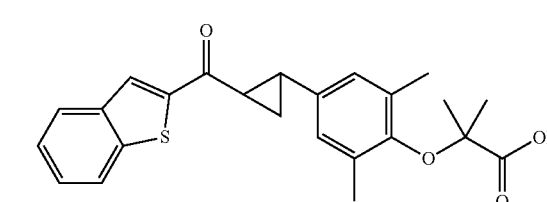
TM38
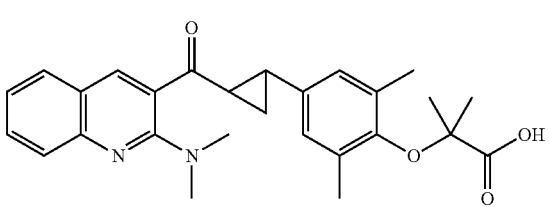
TM39
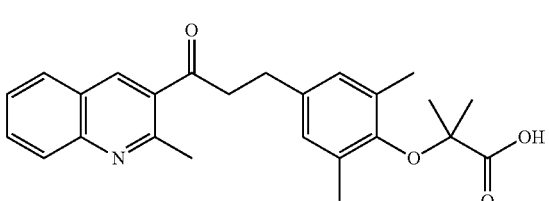
TM40
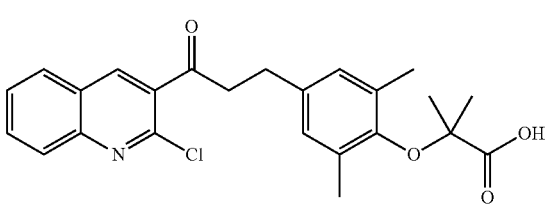

TM41
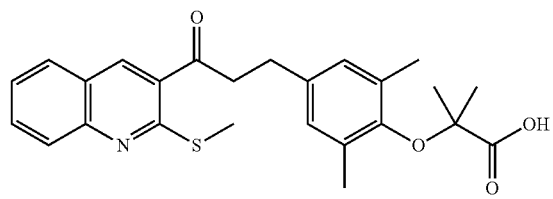
TM42
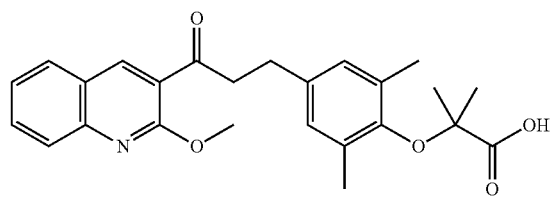
TM43
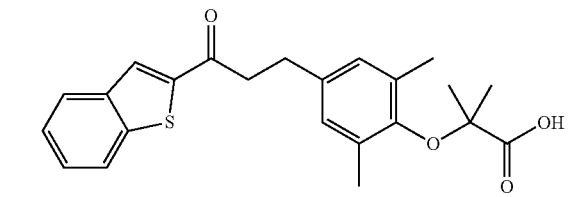
TM44
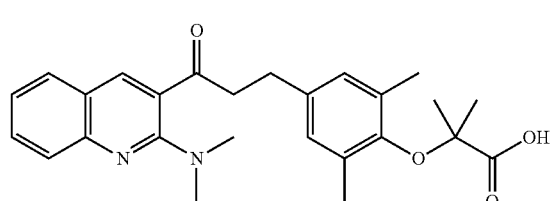
TM45
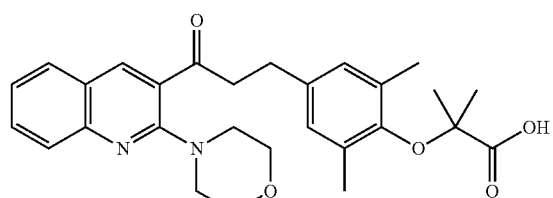
TM46
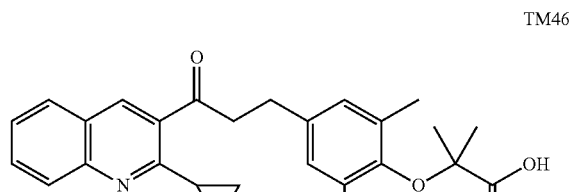
TM47
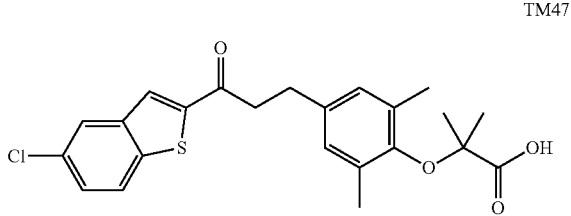
TM48
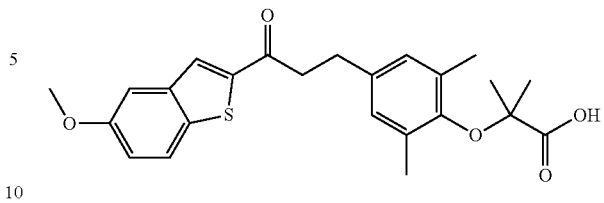
TM49
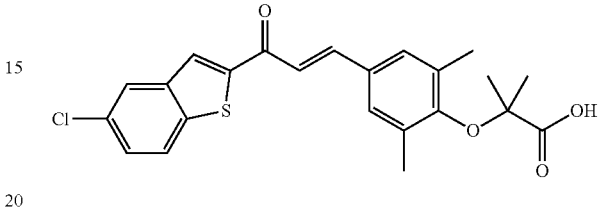
TM50
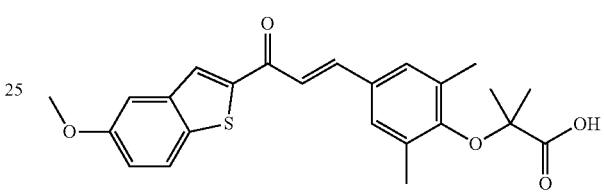
TM51
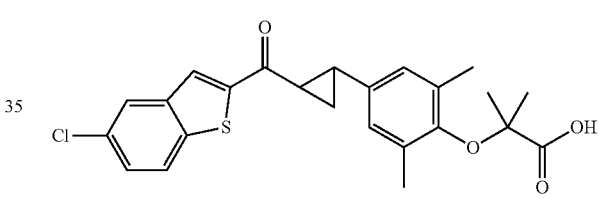
TM52
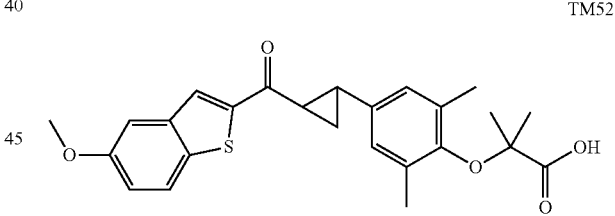
Preparation Method
Another object of the invention is to provide a method for preparing the above described compound, comprising the steps of:
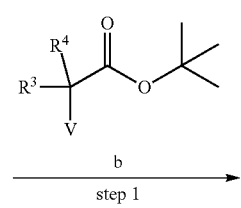

-continued

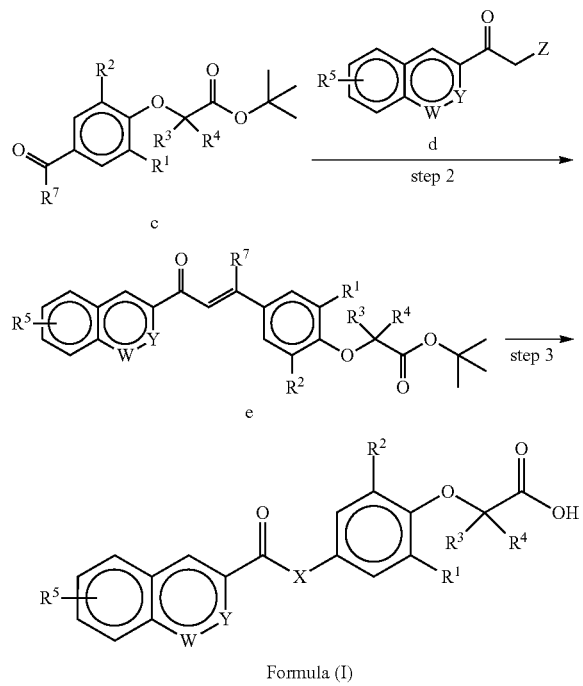

Formula (I)

wherein, V represents halogen or $C_{1-3}$ alkyl sulfonate group optionally substituted by halogen (e.g., trifluoromethanesulfonate group); Z is selected from the group consisting of H, Cl, Br, I and —P(O)(OEt)$_2$. $R^7$ is selected from the group consisting of H, halogen, $C_{1-6}$ alkyl, halogenated $C_{1-6}$ alkyl, $C_{3-6}$ cycloalkyl, —O—($C_{1-6}$ alkyl), 3-10 membered heterocyclyl, $C_{6-14}$ aryl and 5-14 membered heteroaryl; preferably, $R^7$ is selected from H, halogen and $C_{1-6}$ alkyl.

In some embodiments, the preparation method of the compound of the invention comprises the steps of:

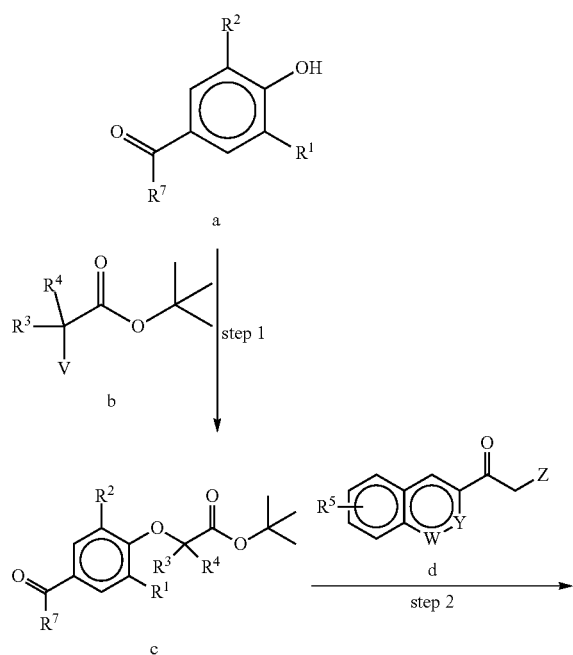

-continued

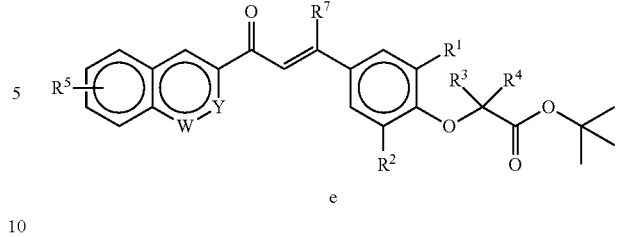

wherein, V represents halogen or $C_{1-3}$ alkyl sulfonate group optionally substituted by halogen (e.g., trifluoromethanesulfonate group), Z is selected from the group consisting of H, Cl, Br, I and —P(O)(OEt)$_2$, and $R^7$ is selected from the group consisting of H, halogen, $C_{1-6}$ alkyl, halogenated $C_{1-6}$ alkyl, $C_{3-6}$ cycloalkyl, —O—($C_{1-6}$ alkyl), 3-10 membered heterocyclyl, $C_{6-14}$ aryl and 5-14 membered heteroaryl; preferably, $R^7$ is selected from H, halogen and $C_{1-6}$ alkyl.

Step 1: subjecting Phenol a and Compound b to a substitution reaction to give Ether Intermediate c.

Step 2: subjecting Intermediate c and Compound d to a condensation reaction to give Alkene Intermediate e (e.g. referring to the method disclosed in Synthesis 1626 (2003), a similar method to Wittig reaction reported by Bizet et al. (Journal of Fluorine Chemistry, 2013, 56-61), a similar method to Wittig-Horner reaction reported by Johnson et al. (Heterocycles, 2006, 2165-2170), or an Aldol condensation reaction method reported by Wang et al. (Chemical Communications, 2016, 2811-2814)).

In an embodiment of the invention, the first step is carried out in the presence of a base selected from organic bases or inorganic bases, including, but not limited to, cesium carbonate, potassium carbonate and potassium tert-butoxide.

In an embodiment of the invention, the second step is carried out in the presence of an organic base, inorganic base or condensing reagent, and the organic base includes, but is not limited to, sodium tert-butoxide, triethylamine, DIPEA, pyridine or DMAP. The inorganic base includes, but is not limited to, NaH, NaOH, Na$_2$CO$_3$ or K$_2$CO$_3$. The condensing reagent includes, but is not limited to, DCC, DIC, EDC, BOP, PyAOP and PyBOP.

In some embodiments, the method for the preparation of the compound of the invention comprises the steps of:

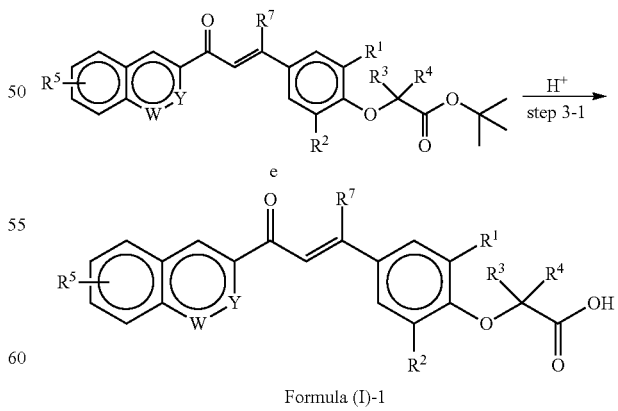

Formula (I)-1

Step 3-1: deprotecting Compound e to give Compound (I)-1.

In some embodiments, the method for the preparation of the compound of the invention comprises the steps of:

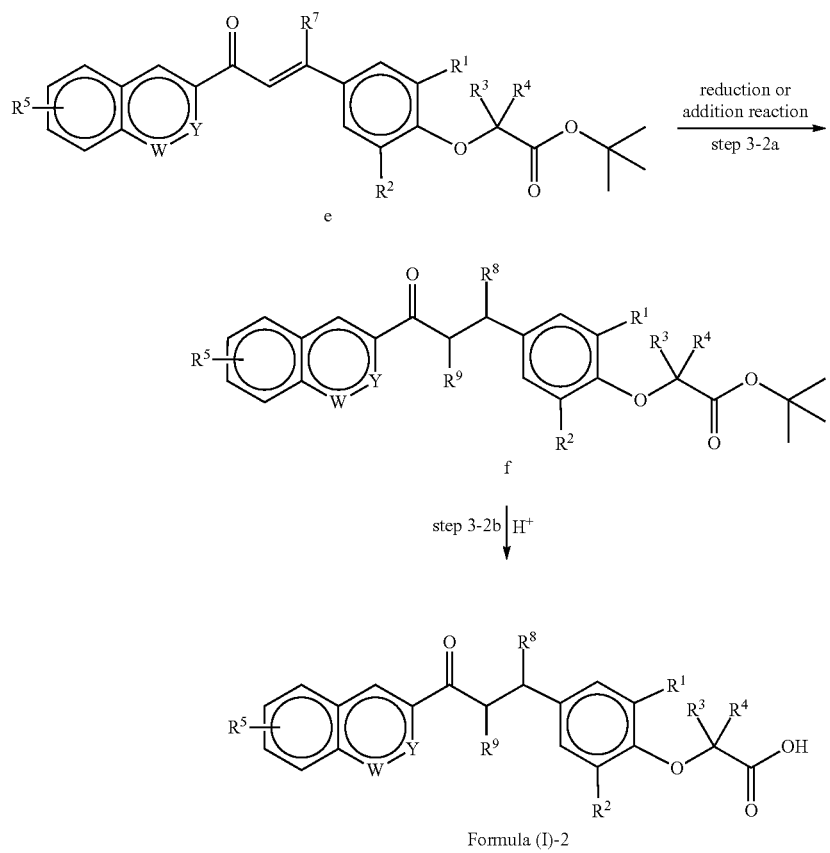
Step 3-2a: subjecting Compound e to a reduction reaction to give Compound f, and preferably the reaction is catalyzed by Pd/C.
Step 3-2b: deprotecting Compound f to give Compound (I)-2.
In some embodiments, the method for the preparation of the compound of the invention comprises the steps of:
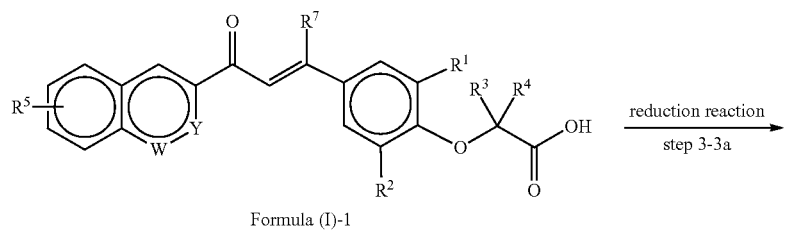

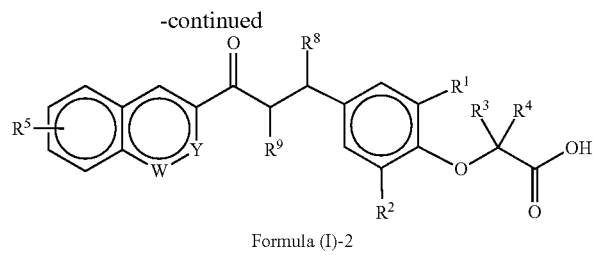

Formula (I)-2

Step 3-3a: subjecting Compound (I)-1 to a reduction reaction to give Compound g, and preferably the reaction is catalyzed by Pd/C or Pd(OH)$_2$/C.

Step 3-3b: subjecting Compound g to an oxidation reaction to give Compound (I)-2, and preferably the reaction is catalyzed by DMP, IBX, PCC, PDC or MnO$_2$.

In some embodiments, the method for the preparation of the compound of the invention comprises the steps of:

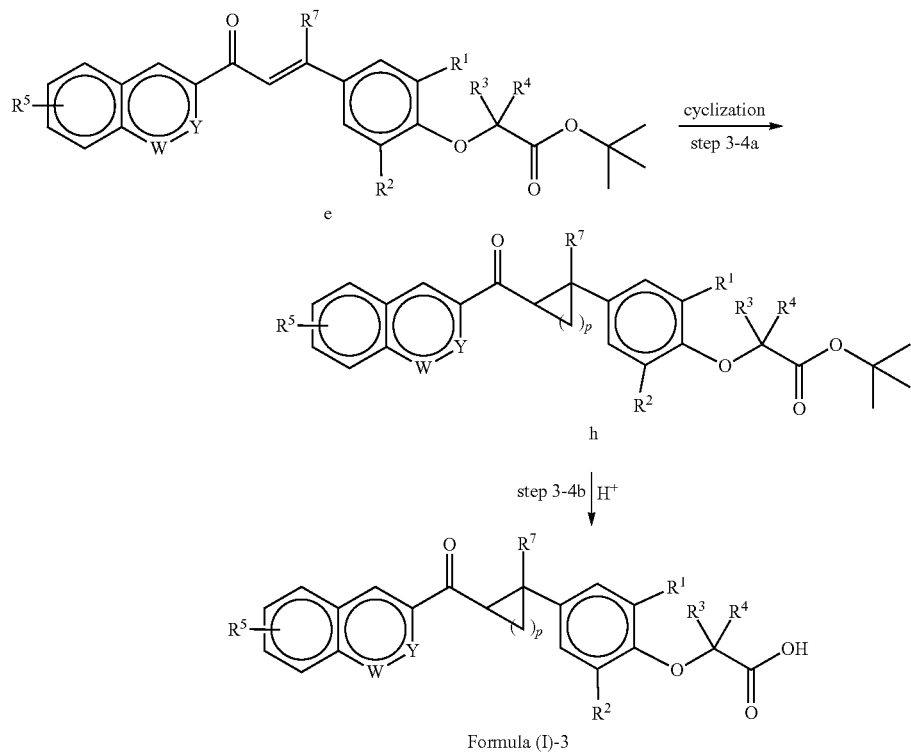

Formula (I)-3 wherein, p is selected from any integer from 1 to 4.

Step 3-4a: subjecting Compound e to a cyclization reaction to give Compound h.

Step 3-4b: deprotecting Compound h to give Compound (I)-3.

According to an embodiment of the invention, step 3-1, step 3-2b, or step 3-4b are carried out in the presence of an acid selected from organic acid or inorganic acid, including but not limited to hydrochloric acid or trifluoroacetic acid.

Those skilled in the art shall understand that the sequence of each step can be adjusted as needed, for example, the hydrogenation or cyclization reaction can be carried out after deprotection of tert-butyl. Those skilled in the art shall understand that tert-butyl of the ester group can be replaced by other similar protecting groups, such as benzyl, p-methoxybenzyl, benzyloxy acyl and substituted silicon groups, which will be removed in subsequent steps to obtain final acid products.

All the above steps can be carried out in an organic solvent. The organic solvent may be a reaction solvent commonly used in the art, such as, but not limited to, N,N-dimethylformamide, dim ethyl sulfoxide, N-methylpyrrolidone, saturated hydrocarbons (e.g. cyclohexane and hexane), halogenated hydrocarbons (e.g. methylene chloride, chloroform and 1,2-dichloroethane), ethers (e.g. tetrahydrofuran, diethyl ether, dioxane and 1,2-dimethoxyethane), nitriles (e.g. acetonitrile) and their mixed solvents.

In addition, the compound of the invention can be prepared by various methods known to those skilled in the art of organic synthesis. The compound of the invention can be synthesized by the method described below, synthetic method known in the field of synthetic organic chemistry or variations thereof known to those skilled in the art. The preferred methods include but are not limited to those described above. The reaction may be carried out in a solvent or mixed solvent, which is suitable for the reagent and material used and for the conversion of the reaction. It should be understood by those skilled in the art of organic synthesis that the functional groups present on the molecules should be consistent with the proposed conversion. Sometimes it is necessary to make a judgment of modifying the sequence of synthesis steps or selecting another specific process route with respect to one process route to obtain the desired compound of the invention.

Further, it should be recognized that, in designing any synthetic route in the art, another major consideration is the correct selection of protecting groups for protecting reactive functional groups present in the compound described in the invention. For the authoritative explanation describing many alternatives to trained people concerned, see Greene et al. (Protective Groups in Organic Synthesis, 4th Edition, Wiley-Inter Science (2006)).

Unless otherwise specified, the substituents of the compound in the above routes are as defined in the invention. Those skilled in the art will appreciate that one or more steps in the above route may be omitted depending on the structure of desired product. Those skilled in the art can appropriately adjust the sequence of reaction steps as required.

Pharmaceutical Composition and Kit Product

The invention further provides a pharmaceutical composition, comprising the compound of the first aspect of the invention, or an isomer, pharmaceutically acceptable salt or ester, hydrate, solvate, any crystal form or racemate, or metabolite, or mixture thereof, and one or more pharmaceutically acceptable carriers.

The pharmaceutical adjuvant mentioned herein refer to the excipient and the additive used in the production of drugs and in the formulation of prescriptions, and refer to a substance that has been reasonably evaluated in terms of safety and are contained in pharmaceutical preparations except for the active ingredients. It is an important component that may affect the quality, safety and effectiveness of drugs, and can be used as an excipients or a carrier for the stability improvement purpose, and has important functions such as hydrotrope-solubilization and sustained release. Depending on the source of the adjuvant, it can be divided into natural product, semi-synthetic product and full-synthetic product. According to its function and use, it also can be divided into solvents, propellants, solubilizers, cosolvents, emulsifiers, colorants, adhesives, disintegrants, fillers, lubricants, wetting agents, osmotic pressure regulators, stabilizers, glidants, flavoring agents, preservatives, suspending agents, coating materials, fragrances, anti-adhesion agents, antioxidants, chelating agents, penetration enhancers, pH regulators, buffers, plasticizers, surfactants, foaming agents, defoamers, thickeners, clathrates, humectants, absorbents, diluents, flocculants and deflocculants, filter aids and release blockers. According to the route of administration, it can be divided into oral administration, injection, mucosal administration, transdermal or local administration, nasal or oral inhalation administration, and ocular administration. Specific pharmaceutical adjuvants include water, lactose, glucose, fructose, sucrose, sorbitol, mannitol, polyethylene glycol, propylene glycol, starch, rubber, gel, alginate, calcium silicate, calcium phosphate, cellulose, aqueous syrup, methylcellulose, polyvinylpyrrolidone, alkyl p-hydroxybenzoate sorbate, talc, magnesium stearate, stearic acid, glycerol, sesame oil, olive oil and soybean oil.

The pharmaceutical composition can be applied in any form as long as it realizes the purpose of prevention, alleviation or cure of symptoms of human or animal sufferers. For example, various suitable dosage forms can be prepared according to the route of administration.

For oral administration, the pharmaceutical composition can be made into any orally acceptable preparation form, including but not limited to tablets, capsules, granules, pills, syrups, oral solutions, oral suspensions, oral emulsions, and the like. The oral suspensions are usually prepared by mixing the active ingredients with suitable emulsifiers and suspending agents. Optionally, sweeteners, fragrances or colorants may be added to the above oral preparation form.

For percutaneous or topical administration, the pharmaceutical composition can be made into an appropriate ointment, lotion or liniment, wherein the active ingredient is suspended or dissolved in one or more carriers. Carriers that can be used in ointment preparations include, but are not limited to, mineral oil, liquid vaseline, white vaseline, propylene glycol, polyethylene oxide, polypropylene oxide, emulsified wax and water; carriers that can be used in lotions or liniments include, but are not limited to, mineral oil, dehydrated sorbitan monostearate, tween 60, hexadecyl ester wax, cetearyl alcohol, 2-octyldodecanol, benzyl alcohol and water.

The pharmaceutical composition can be used in the form of injection, including injection, sterile powder for injection and concentrated solution for injection. Wherein, carriers and solvents that can be used include water, Ringer's solution and isotonic sodium chloride solution. In addition, sterilized non-volatile oil can also be used as solvent or suspending medium, such as monoglyceride or diglyceride.

The application further provides a kit product comprising the compound or a pharmaceutically acceptable salt, ester, stereoisomer, tautomer, polymorph, solvate, N-oxide, isotope-labeled compound, metabolite, prodrug or mixture thereof, or a pharmaceutical composition, and optional package insert.

Treatment Methods and Uses

Another Object of the Invention is to Provide Use of the Compound of the Invention or the pharmaceutically acceptable salt, ester, stereoisomer, tautomer, polymorph, solvate, metabolite or prodrug thereof, or a mixture thereof or the pharmaceutical composition of the invention for the manufacture of a medicament for the prevention or treatment of a PPAR-related disease.

Another object of the invention is to provide the compound of the invention or the pharmaceutically acceptable salt, ester, stereoisomer, tautomer, polymorph, solvate, metabolite or prodrug thereof, or a mixture thereof or the pharmaceutical composition of the invention for preventing or treating a PPAR-related disease.

Another object of the invention is to provide a method for preventing or treating a PPAR-related disease, which comprises administering to an individual in need thereof an effective amount of the compound of the invention or the pharmaceutically acceptable salt, ester, stereoisomer, tautomer, polymorph, solvate, metabolite or prodrug thereof, or a mixture thereof, or a pharmaceutical composition of the invention.

Another aspect of the invention provides use of the compound of the invention or the pharmaceutically acceptable salt, ester, stereoisomer, tautomer, polymorph, solvate, N-oxide, isotope-labeled compound, metabolite or prodrug thereof or the pharmaceutical composition of the invention in a reagent for the activation of PPAR in cells. In some preferred embodiments, the reagent is used in an in vivo method. In some preferred embodiments, the reagent is used in an in vitro method.

Another aspect of the invention provides the compound of the invention or the pharmaceutically acceptable salt, ester, stereoisomer, tautomer, polymorph, solvate, N-oxide, isotope-labeled compound, metabolite or prodrug thereof or the pharmaceutical composition of the invention, for use in the activation of PPAR in cells. In some preferred embodiments, the compound or the pharmaceutically acceptable salt, ester, stereoisomer, tautomer, polymorph, solvate, N-oxide, isotope-labeled compound, metabolite or prodrug thereof or a pharmaceutical composition of the invention are used in the in vivo method. In some preferred embodiments, the compound or the pharmaceutically acceptable salt, ester, stereoisomer, tautomer, polymorph, solvate, N-oxide, isotope-labeled compound, metabolite or prodrug thereof or pharmaceutical composition of the invention are used in the in vitro method.

Another aspect of the invention provides a method for activating PPAR in a cell, which comprises the step of contacting the cell with an effective amount of the compound of the invention or the pharmaceutically acceptable salt, ester, stereoisomer, tautomer, polymorph, solvate, N-oxide, isotope-labeled compound, metabolite or prodrug thereof or the pharmaceutical composition of the invention. In some preferred embodiments, the method is carried out in vivo. In some preferred embodiments, the method is carried out in vitro.

In some preferred embodiments, the PPAR is PPAR α and/or PPAR δ.

In one embodiment of the invention, the PPAR-related disease is a liver disease, for example, selected from liver fibrosis or fatty liver disease. In some preferred embodiments, the disease or condition is non-alcoholic fatty liver disease (NAFLD), such as simple fatty liver (SFL) or non-alcoholic steatohepatitis (NASH).

In some preferred embodiments, the "cell" is a cell line or a cell from a subject. The term "effective amount" as used herein refers to an amount of a compound that, to a certain extent, alleviates one or more symptoms of the condition being treated after administration.

The dosage regimen can be adjusted to provide the optimal desired response. For example, administration in single infusion, split-dose administration over time, or proportional reduction or increase of dose as indicated by the treatment condition are allowed. Attention shall be paid to the fact that the amount of the dose may vary depending on the type and severity of the condition to be alleviated, and may include single or multiple doses. It should be further understood that for any particular individuals, the specific dosage regimen should be adjusted over time according to individual needs and the professional judgment of the person responsible for dispensing the composition or supervising the administration of the composition. The dosage and dosage regimen of the pharmaceutical composition can be easily determined by those of ordinary skill in the clinical art. The composition or compound of the invention is generally administered twice a day to once 3 days, preferably once a day, and the total amount of administration is 0.01 to 1000 mg/time. Generally, the therapeutic dose varies depending on the considerations, such as the age, gender and general health status of the patient to be treated; frequency of treatment and nature of desired effect; degree of tissue damage; duration of symptoms; other variables that can be adjusted by individual physicians. The desired dose may be administered in one or more times to obtain the desired result. The pharmaceutical composition of the invention may also be provided according to the unit dose.

Unless otherwise specified, the term "treatment" as used herein refers to reversing, alleviating, inhibiting the progression of a disease or condition to which such term applies, or one or more symptoms of such a disease or condition, or preventing such a disease or condition or one or more symptoms of such a disease or condition.

As used herein, the "individual" or "subject" includes human or non-human animals. Exemplary human individuals include human individuals (referred to as patients) or normal individuals suffering from diseases (e.g., diseases described herein). "Non-human animal" in the invention includes all vertebrates, such as non-mammals (e.g., birds, amphibians and reptiles) and mammals, such as non-human primates, domestic animals and/or domesticated animals (e.g., sheep, dogs, cats, cows and pigs).

EXAMPLES

The invention is further illustrated in detail by the following examples and test examples, which are not intended to limit the scope of the invention, and may be modified without departing from the scope of the invention.

Agilent (ESI) mass spectrometer (manufacturer: Agilent, model: Agilent 6120B) is used for MS determination.

Shimadzu LC-8A liquid chromatograph (YMC, ODS, 250×20 mm column) is used for conducting preparative high-performance liquid chromatograph method.

GF 254 (0.4-0.5 nm) silica gel plate manufactured in Yantai is used for thin layer chromatography purification.

The reaction is monitored by thin layer chromatography (TLC) or LC-MS, and the developing system includes but is not limited to dichloromethane and methanol system, n-hexane and ethyl acetate system, petroleum ether and ethyl acetate system. The volume ratio of the solvent is adjusted according to the polarity of the compound, or by adding triethylamine.

For the column chromatography, Qingdao Haiyang 200~300 mesh silica gel is generally used as stationary phase. The eluent system includes, but is not limited to, dichloromethane and methanol system, and n-hexane and ethyl acetate system. The volume ratio of the solvent is adjusted according to the polarity of the compound, or by adding a small amount of triethylamine or the like.

Unless otherwise specified in the examples, the reaction temperature is room temperature (20° C. to 30° C.).

The reagents used in the examples are purchased from Acros Organics, Aldrich Chemical Company or Topbiochem LTD. etc.

Abbreviations as used herein have the following meanings:

| Abbreviations | Meaning |
|---|---|
| AcCl | Acetyl chloride |
| Ac$_2$O | Acetic anhydride |
| AlCl$_3$ | Aluminium trichloride |
| aq. | Aqueous solution |
| Boc | Tert-butoxycarbonyl |
| CF$_3$SO$_3$H | Trifluoromethanesulfonic acid |
| DCM | Dichloromethane |
| DIPEA | Diisopropylethylamine |
| BBr$_3$ | Boron tribromide |
| DMF | N,N-dimethylformamide |
| DMP | Dess-Martin periodinane |
| DMSO | Dimethyl sulfoxide |
| EA | Ethyl acetate |
| Et$_3$N | Triethylamine |
| EtOAc | Ethyl acetate |
| EtOH | Ethanol |
| K$_2$CO$_3$ | Potassium carbonate |
| TFA | Trifluoroacetic acid |
| H$_2$ | Hydrogen |
| HBr | Hydrogen bromide |
| HCl | Hydrogen chloride |
| H$_2$O | Water |

| Abbreviations | Meaning |
|---|---|
| LAH | Lithium aluminum hydride |
| CH₃MgBr | Methyl magnesium bromide |
| LC-MS | Liquid chromatography-mass spectrometry |
| LDA | Lithium diisopropylamide |
| MeCN | Acetonitrile |
| MeOH | Methanol |
| MeONa | Sodium methoxide |
| NaBH₄ | Sodium borohydride |
| NMP | N-methyl pyrrolidone |
| Cs₂CO₃ | Cesium carbonate |
| Na₂CO₃ | Sodium carbonate |
| NaOH | Sodium hydroxide |
| KOH | Potassium hydroxide |
| Na₂SO₄ | Sodium sulfate |
| m-CPBA | meta-chloroperoxybenzoic acid |
| Pd/C | Palladium carbon |
| NaSMe | Sodium methyl mercaptide |
| Py | Pyridine |
| SOCl₂ | Thionyl chloride |
| rt | Room temperature |
| THF | Tetrahydrofuran |
| TLC | Thin layer chromatography |

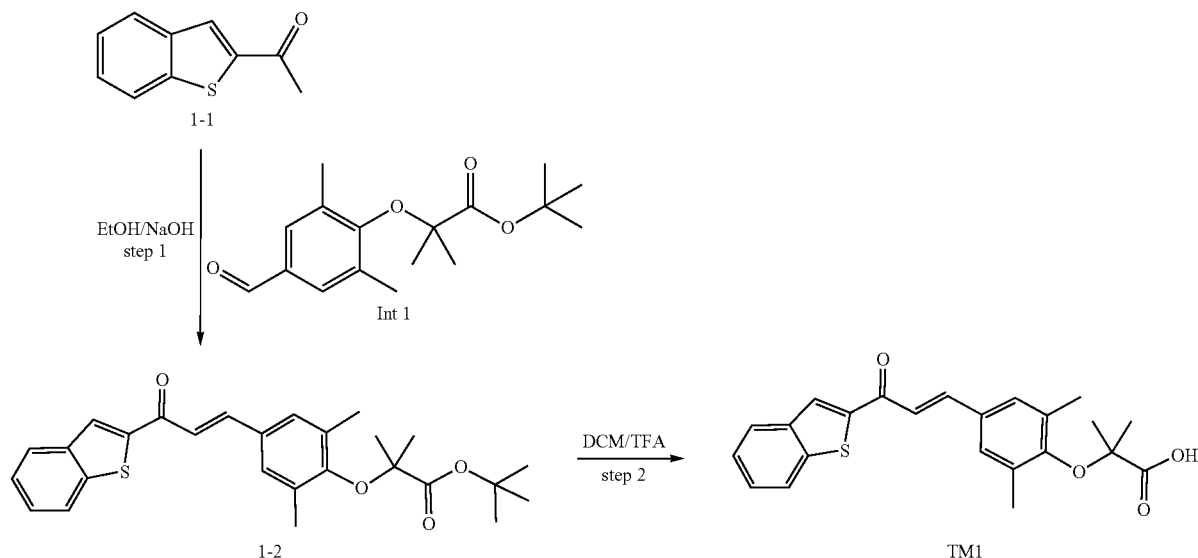

Example 1: Preparation of tert-butyl 2-(4-formyl-2,6-dimethylphenoxy)-2-methylpropionate (Int1)

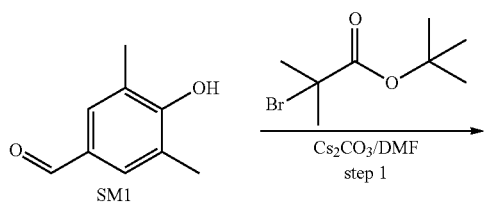

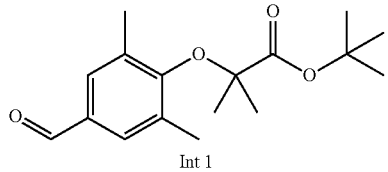

Int 1

To SM1 3,5-dimethyl-4-hydroxybenzaldehyde (100 g, 0.67 mol) dissolved in DMF (800 ml) was added cesium carbonate (543 g, 1.67 mmol). The system was heated to 100° C. and reacted for 30 min, followed by dropwise addition of tert-butyl 2-bromoisobutyrate (297 g, 1.33 mmol), then reacted at 120° C. for 8 h. No progression of the reaction was monitored by LC-MS. The reaction solution was poured into ice water for separation. The aqueous phase was extracted with ethyl acetate. The organic phases were combined, dried with anhydrous sodium sulfate, and filtered. The filtrate was concentrated to obtain a crude product, which was purified by silica gel column chromatography to obtain compound Int 1 (31 g), with a yield of 16%.

Example 2: Preparation of (E)-2-(4-(3-(benzo [b] thien-2-yl)-3-oxo-1-propen-1-yl)-2,6-dimethylphenoxy)-2-methylpropionic acid (TM1)

Step 1: Preparation of tert-butyl (E)-2-(4-(3-(benzo [b] thien-2-yl)-3-oxo-1-propen-1-yl)-2,6-dimethylphenoxy)-2-methylpropionate (1-2)

Compound 1-1 (150 mg, 0.74 mmol) and Int 1 (216 mg, 0.74 mmol) were dissolved in ethanol (20 mL). The mixture was cooled in an ice-water bath for 10 min, followed by dropwise addition of 10% NaOH (0.35 mL), and reacted overnight. No progression of the reaction was monitored by LC-MS. Water and ethyl acetate were added to the mixture for extraction. The organic phases were combined, washed once with saturated saline solution, dried with sodium sulfate, filtered, concentrated, and purified by column chromatography to obtain the target product 2-2 (160 mg) with a yield of 45%.

Step 2: Preparation of (E)-2-(4-(3-(benzo [b] thien-2-yl)-3-oxo-1-propen-1-yl)-2,6-dimethylphenoxy)-2-methylpropionic acid (TM1)

Compound 1-2 (140 mg, 0.29 mmol) was dissolved in DCM (4.5 mL), cooled in an ice-water bath for 10 min. To the mixture was added TFA (1.5 mL) dropwise, and then reaction was conducted for 1 h. LC-MS was applied to monitor the completion of the reaction. The reaction solution was concentrated and purified by column chromatography to obtain the target product TM1 (67 mg) with a yield of 54%.

MS m/z (ESI): 395 [M+H]$^+$

1HNMR (400 MHz, DMSO-d6) δ: 12.97 (s, 1H), 8.75 (s, 1H), 8.12-8.02 (m, 2H), 7.93 (d, J=16.0 Hz, 1H), 7.68 (d, J=16.0 Hz, 1H), 7.62 (s, 2H), 7.59-7.47 (m, 2H), 2.25 (s, 6H), 1.41 (s, 6H).

Example 3: Preparation of (E)-2-(4-(3-(quinolin-3-yl)-3-oxo-1-propen-1-yl)-2,6-dimethylphenoxy)-2-methylpropionic acid (TM2)

Example 4: Preparation of (E)-2-(4-(3-(2-chloroquinolin-3-yl)-3-oxo-1-propen-1-yl)-2,6-dimethylphenoxy)-2-methyl propionic acid (TM3)

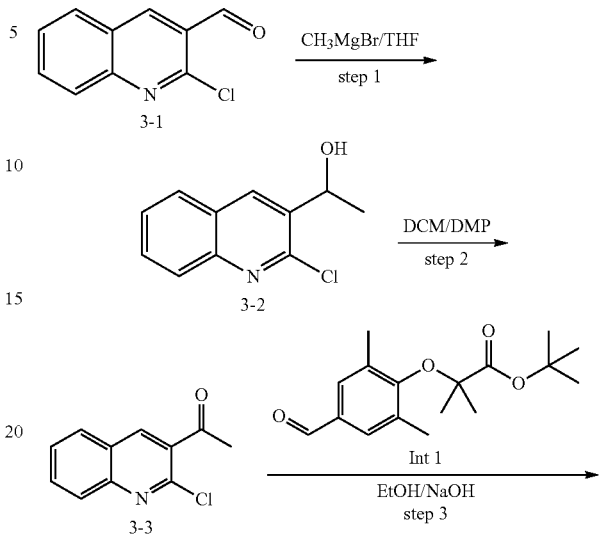

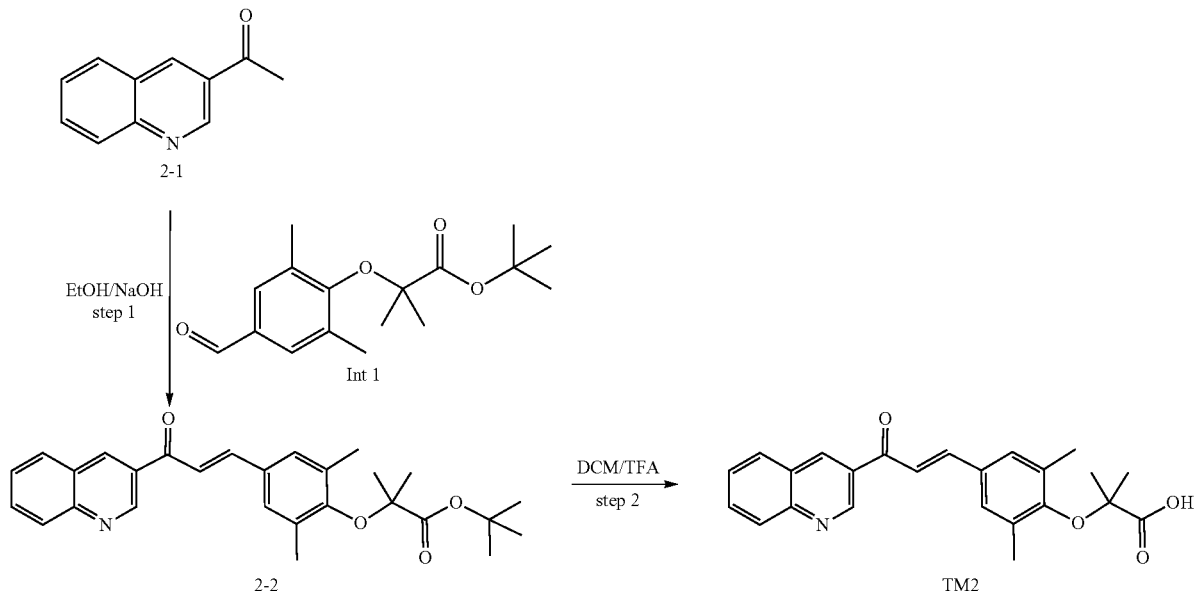

TM2 was synthesized via a method similar to that described in step 1 to step 2 of Example 2 with a yield of 38%, except that 2-1 was used in step 1 of Example 3 instead of 1-1 in step 1 of Example 2.

MS m/z (ESI): 390 [M+H]$^+$

1 HNMR (400 MHz, DMSO-d6) δ: 12.95 (s, 1H), 9.48 (d, J=2.0 Hz, 1H), 9.28 (d, J=2.0 Hz, 1H), 8.22 (d, J=4.0 Hz, 1H), 8.14 (d, J=4.0 Hz, 1H), 8.00 (d, J=16.0 Hz, 1H), 7.98-7.92 (m, 1H), 7.81-7.71 (m, 2H), 7.64 (s, 2H), 2.25 (s, 6H), 1.41 (s, 6H).

-continued

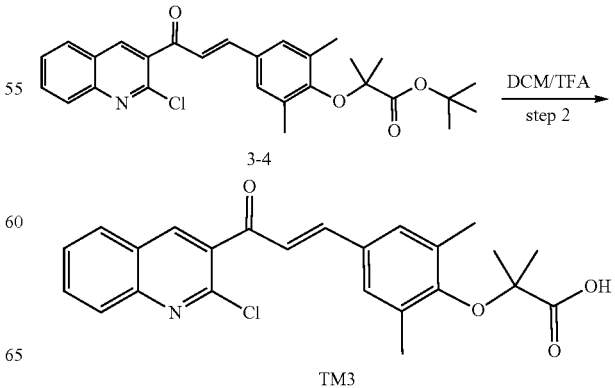

Step 1: Preparation of 1-(2-chloroquinolin-3-yl) ethanol (3-2)

CH₃MgBr (1M) (196 mL, 196 mmol) was dissolved in THF (125 mL), and cooled in ice water bath for 10 min. Then, to the mixture was added dropwise a solution of 2-chloro-3-formylquinoline (25 g, 130 mmol) in THF (550 mL). The reaction mixture was reacted for 4 h with stirring. No progression of the reaction was monitored by LC-MS. The reaction solution was poured into saturated aqueous solution of ammonium chloride, extracted with ethyl acetate. The organic phases were combined, washed once with saturated saline solution, dried with sodium sulfate, filtered and concentrated to obtain the target product 3-2 (28 g), which was directly used in the next reaction without purification.

Step 2: Preparation of 2-chloro-3-acetylquinoline (3-3)

Compound 3-2 (28 g, 130 mmol) was dissolved in DCM (560 mL), cooled in an ice-water bath for 15 min, then added with DMP (83 g, 196 mmol) in batches. The mixture was reacted for 2 h. LC-MS was applied to monitor the completion of the reaction. The reaction solution was poured into aqueous solution of sodium sulfite, filtered with diatomite. The filtrate was extracted with DCM. The organic phases were combined, washed once with saturated saline solution, dried with sodium sulfate, filtered, concentrated, and purified by column chromatography to obtain the target product 3-3 (18.5 g) with a yield of 69%.

Steps 3 and 4: Two-step synthesis of (E)-2-(4-(3-(2-chloroquinolin-3-yl)-3-oxo-1-propen-1-yl)-2,6-dimethylphenoxy)-2-methyl propionic acid (TM3)

TM3 was synthesized via a method similar to that described in step 1 to step 2 of Example 2 with a total yield of 26%, except that 3-3 is used in step 3 of Example 4 instead of 1-1 in step 1 of Example 2.
MS m/z (ESI): 424 [M+H]⁺
1HNMR (400 MHz, DMSO-d6) δ: 12.96 (s, 1H), 8.71 (s, 1H), 8.15 (d, J=4.0 Hz, 1H), 8.06 (d, J=4.0 Hz, 1H), 7.98-7.92 (m, 1H), 7.80-7.72 (m, 1H), 7.50 (s, 2H), 7.45 (d, J=16.0 Hz, 1H), 7.27 (d, J=16.0 Hz, 1H), 2.18 (s, 6H), 1.37 (s, 6H).

Example 5: Preparation of (E)-2-(4-(3-(2-methoxy-quinolin-3-yl)-3-oxo-1-propen-1-yl)-2,6-dimethylphenoxy)-2-methylpropionic acid (TM4)

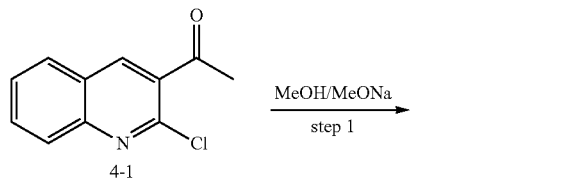

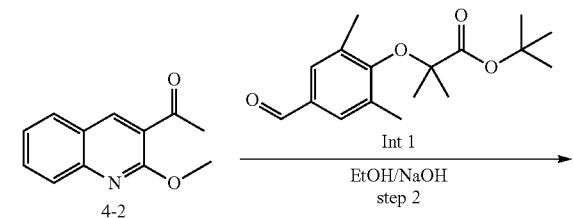

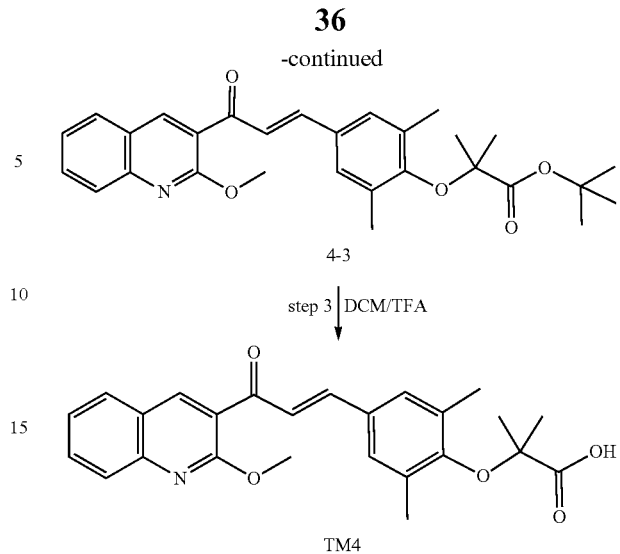

Step 1: Preparation of 2-methoxy-3-acetylquinoline (4-2)

To compound 4-1 (300 mg, 1.46 mmol) dissolved in methanol (5 mL) was added sodium methoxide (5M) (1.46 mL, 7.30 mmol). When the completion of the reaction was monitored by LC-MS, the reaction solution was poured into ice water. The mixture was adjusted with 3N HCl aqueous solution to pH 2, then extracted with ethyl acetate. The organic phases were combined, washed once with saturated saline solution, dried with sodium sulfate, filtered, concentrated, and purified by column chromatography to obtain the target product 4-2 (270 mg) with a yield of 92%.

Steps 2 and 3: Two-step synthesis of (E)-2-(4-(3-(2-methoxyquinoline-3-yl)-3-oxo-1-propen-1-yl)-2,6-dimethylphenoxy)-2-methylpropionic acid (TM4)

TM4 was synthesized via a method similar to that described in step 1 to step 2 of Example 2 with a total yield of 25%, except that 4-2 is used in step 2 of Example 5 instead of 1-1 in step 1 of Example 2.
MS m/z (ESI): 420 [M+H]⁺
1HNMR (400 MHz, DMSO-d6) δ: 12.96 (s, 1H), 8.72 (s, 1H), 8.02 (d, J=4.0 Hz, 1H), 7.85 (d, J=4.0 Hz, 1H), 7.81-7.74 (m, 1H), 7.55-7.48 (m, 1H), 7.47 (d, J=16.0 Hz, 1H), 7.46 (s, 2H), 7.34 (d, J=16.0 Hz, 1H), 4.05 (s, 3H), 2.19 (s, 6H), 1.38 (s, 6H).

Example 6: Preparation of (E)-2-(4-(3-(2-(2-methoxyethoxy) quinolin-3-yl)-3-oxo-1-propen-1-yl)-2,6-dimethylphenoxy)-2-methylpropionic acid (TM5)

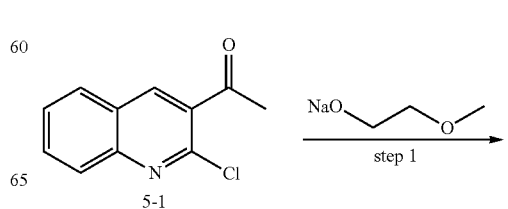

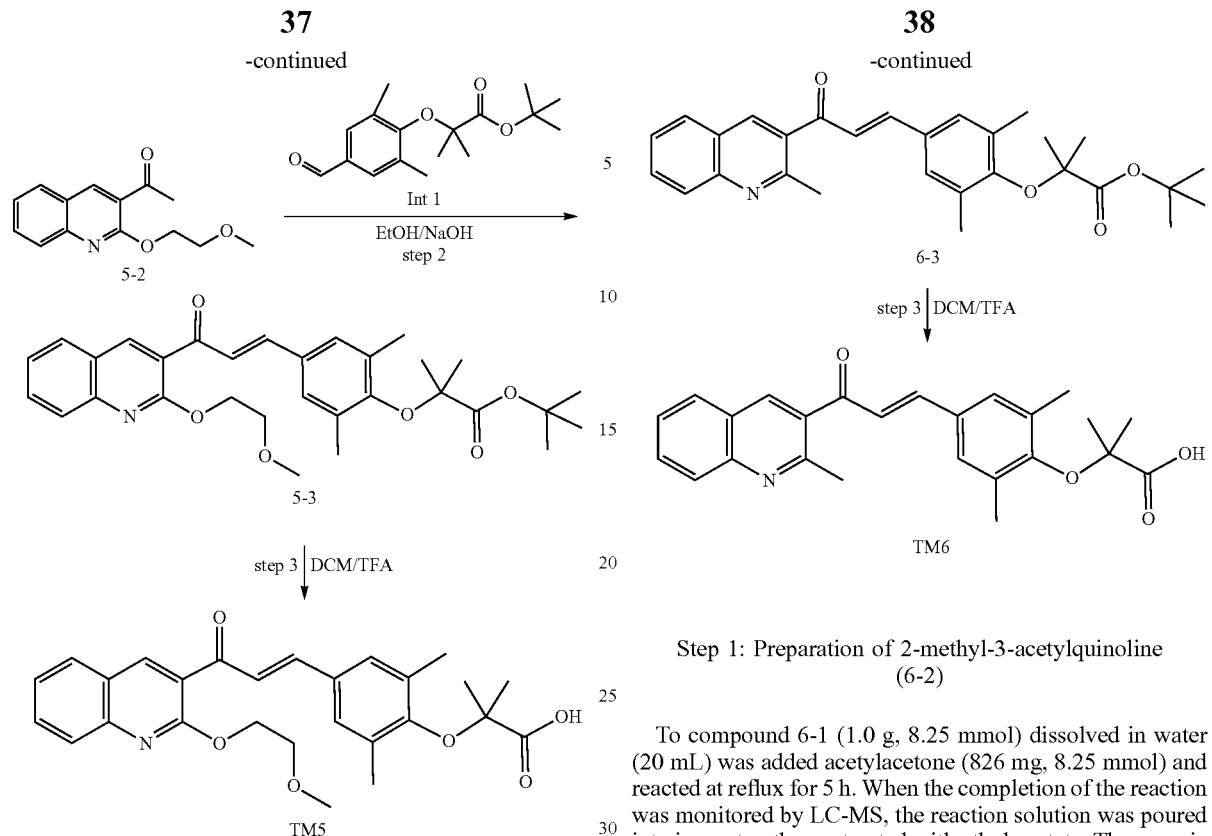

TM5 was synthesized via a method similar to that described in step 1 to step 3 of Example 5 with a yield of 20%, except that sodium 2-methoxyethanolate is used in step 1 of Example 6 instead of sodium methoxide compound in step 1 of Example 5.

MS m/z (ESI): 464 [M+H]+

1HNMR (400 MHz, DMSO-d6) δ: 12.99 (s, 1H), 8.59 (s, 1H), 8.05 (d, J=4.0 Hz, 1H), 7.83 (d, J=4.0 Hz, 1H), 7.80-7.75 (m, 1H), 7.55-7.48 (m, 3H), 7.45 (s, 2H), 4.68-4.62 (m, 2H), 3.77-3.71 (m, 2H), 3.25 (s, 3H), 2.17 (s, 6H), 1.36 (s, 6H).

Example 7: Preparation of (E)-2-(4-(3-(2-methylquinolin-3-yl)-3-oxo-1-propen-1-yl)-2,6-dimethylphenoxy)-2-methylpropionic acid (TM6)

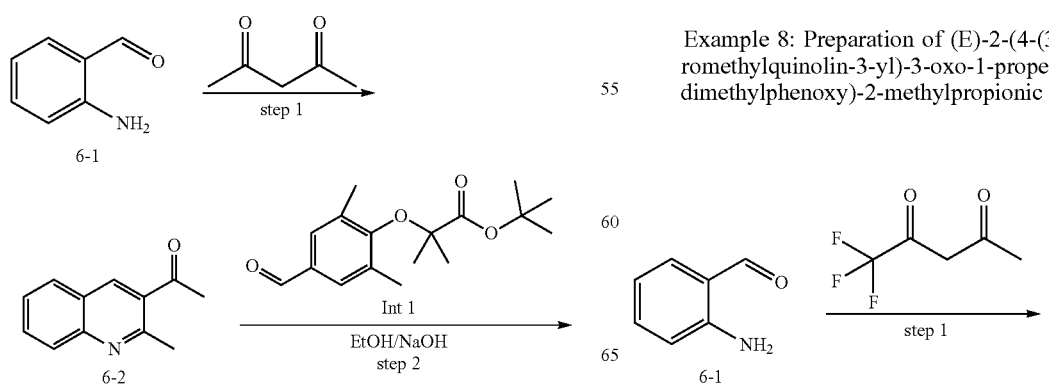

Step 1: Preparation of 2-methyl-3-acetylquinoline (6-2)

To compound 6-1 (1.0 g, 8.25 mmol) dissolved in water (20 mL) was added acetylacetone (826 mg, 8.25 mmol) and reacted at reflux for 5 h. When the completion of the reaction was monitored by LC-MS, the reaction solution was poured into ice water, then extracted with ethyl acetate. The organic phases were combined, washed once with saturated aqueous salt solution, dried with sodium sulfate, filtered and concentrated, and purified by column chromatography to obtain the target product 6-2 (780 mg) with a yield of 51%.

Steps 2 and 3: Two-step synthesis of (E)-2-(4-(3-(2-methyl quinolin-3-yl)-3-oxo-1-propen-1-yl)-2,6-dimethylphenoxy)-2-methylpropionic acid (TM6)

TM6 was synthesized via a method similar to that described in step 1 to step 2 of Example 2 with a yield of 18%, except that 6-2 is used in step 2 of Example 7 instead of 1-1 in step 1 of Example 2.

MS m/z (ESI): 404 [M+H]+

1HNMR (400 MHz, DMSO-d6) δ: 12.97 (s, 1H), 8.69 (s, 1H), 8.08 (d, J=4.0 Hz, 1H), 8.00 (d, J=4.0 Hz, 1H), 7.88-7.80 (m, 1H), 7.68-7.60 (m, 1H), 7.51 (s, 2H), 7.49 (d, J=16.0 Hz, 1H), 7.43 (d, J=16.0 Hz, 1H), 2.72 (s, 3H), 2.20 (s, 6H), 1.38 (s, 6H).

Example 8: Preparation of (E)-2-(4-(3-(2-trifluoromethylquinolin-3-yl)-3-oxo-1-propen-1-yl)-2,6-dimethylphenoxy)-2-methylpropionic acid (TM7)

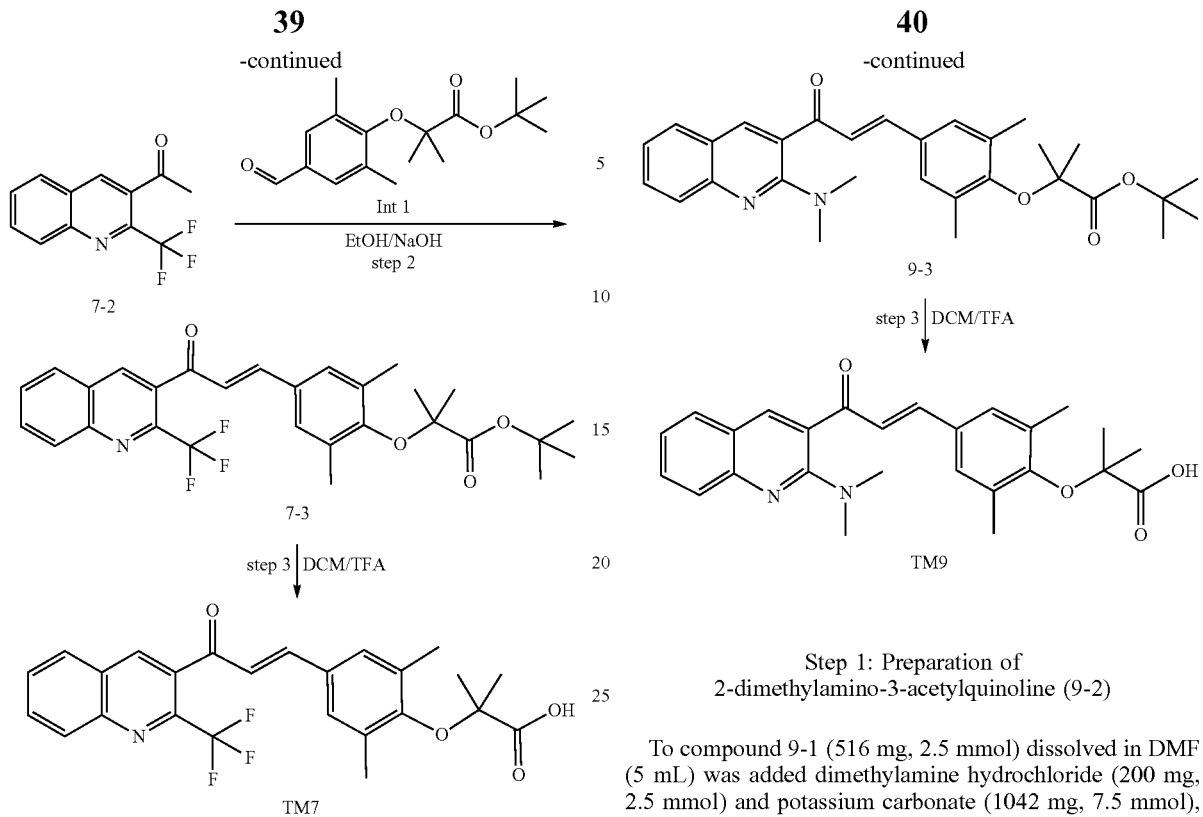

TM7 was synthesized via a method similar to that described in step 1 to step 3 of Example 7 with a yield of 21%, except that trifluoroacetylacetone is used in step 1 of Example 8 instead of acetylacetone compound in step 1 of Example 7.

MS m/z (ESI): 458 [M+H]$^+$ 1HNMR (400 MHz, DMSO-d6) δ: 12.97 (s, 1H), 8.86 (s, 1H), 8.28-8.20 (m, 2H), 8.10-8.00 (m, 1H), 7.95-7.85 (m, 1H), 7.48 (s, 2H), 7.44 (d, J=16.0 Hz, 1H), 7.28 (d, J=16.0 Hz, 1H), 2.17 (s, 6H), 1.37 (s, 6H).

Example 9: Preparation of (E)-2-(4-(3-(2-dimethylaminoquinolin-3-yl)-3-oxo-1-propen-1-yl)-2,6-dimethylphenoxy)-2-methylpropionic acid (TM9)

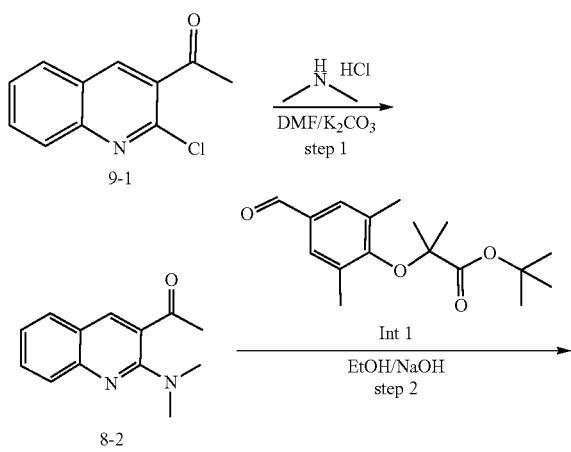

Step 1: Preparation of 2-dimethylamino-3-acetylquinoline (9-2)

To compound 9-1 (516 mg, 2.5 mmol) dissolved in DMF (5 mL) was added dimethylamine hydrochloride (200 mg, 2.5 mmol) and potassium carbonate (1042 mg, 7.5 mmol), then heated at 60° C. for 4 h. The mixture was added with water and ethyl acetate for extraction. The organic phase was washed twice with saturated brine, dried and concentrated, and separated by column chromatography to obtain the desired product 9-2 (452 mg) with a yield of 84%.

Step 2: Preparation of (E)-2-(4-(3-(2-dimethylaminoquinolin-3-yl)-3-oxo-1-propen-1-yl)-2,6-dimethylphenoxy)-2-methylpropionic acid tert-butyl ester (9-3)

Compound 9-2 (100 mg, 0.47 mmol) and Int1 (136 mg, 0.47 mmol) were dissolved in 10 mL of anhydrous ethanol, to the mixture was added 10% sodium hydroxide solution (0.13 mL, 0.35 mmol) dropwise in an ice bath and reacted for 4 h. After TLC showed the completion of the reaction, the reaction solution was concentrated. Dichloromethane was added to the residue for dissolution. The solution was filtered. the mother liquor was concentrated, and separated by preparation plate to obtain the target product 9-3 (154 mg) with a yield of 53%.

Step 3: Preparation of (E)-2-(4-(3-(2-dimethylaminoquinolin-3-yl)-3-oxo-1-propen-1-yl)-2,6-dimethylphenoxy)-2-methylpropionic acid (TM9)

To 9-3 (154 mg, 0.31 mmol) dissolved in 5 mL of dichloromethane was added trifluoroacetic acid (1 mL) and stirred at room temperature for 2 h. The reaction mixture was concentrated, and lyophilized with water to obtain the desired product TM9 (109 mg) with a yield of 80%.

MS m/z (ESI): 433 [M+H]$^+$

1 HNMR (400 MHz, DMSO-d6) δ: 8.58 (s, 1H), 7.96-7.94 (m, 1H), 7.87 (s, 1H), 7.79-7.76 (s, 1H), 7.69 (d, J=16.0 Hz, 1H), 7.51 (s, 2H), 7.45-7.42 (s, 1H), 7.33 (d, J=16.0 Hz, 1H), 3.12 (s, 6H), 2.20 (s, 6H), 1.38 (s, 6H).

Example 10: Preparation of (E)-2-(4-(3-(2-(1-pyrrolidinyl) quinolin-3-yl)-3-oxo-1-propen-1-yl)-2,6-dimethylphenoxy)-2-methylpropionic acid (TM8)

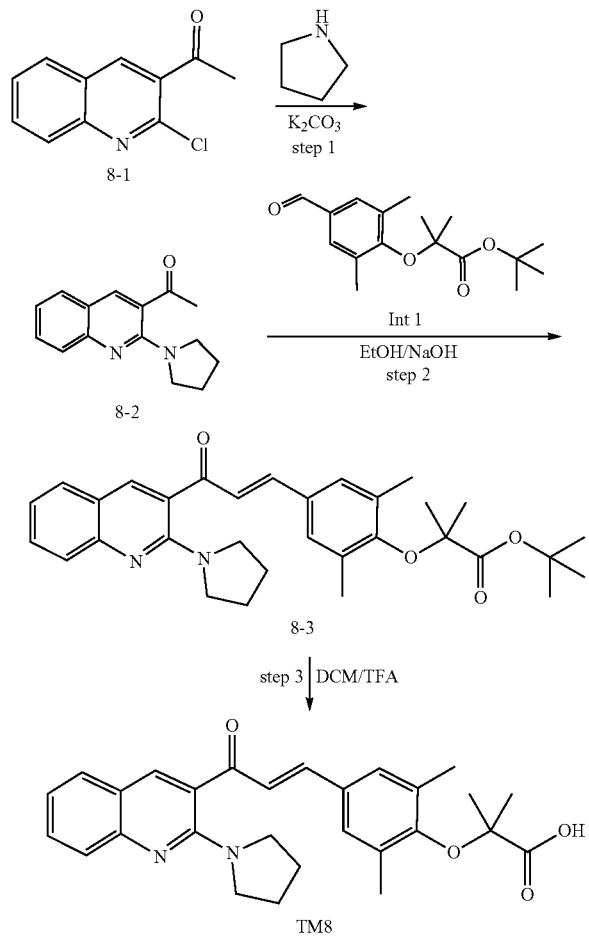

Compound TM8 was synthesized via a method similar to that described in step 1 to step 3 of Example 5 with a yield of 44%, except that pyrrolidine is used in step 1 of Example 10 instead of sodium methoxide in step 1 of Example 5.

MS m/z (ESI): 459 [M+H]$^+$

1HNMR (400 MHz, DMSO-d6) δ: 8.71 (s, 1H), 8.07-8.05 (m, 1H), 8.01 (d, J=8.0 Hz, 1H), 7.88-7.84 (m, 1H), 7.71 (d, J=16.0 Hz, 1H), 7.52 (s, 3H), 7.33 (d, J=16.0 Hz, 1H), 3.54 (s, 4H), 2.20 (s, 6H), 1.99 (s, 4H), 1.39 (s, 6H).

Example 11: Preparation of (E)-2-(4-(3-(2-(morpholin-4-yl) quinolin-3-yl)-3-oxo-1-propen-1-yl)-2,6-dimethylphenoxy)-2-methylpropionic acid (TM10)

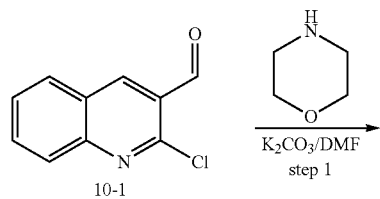

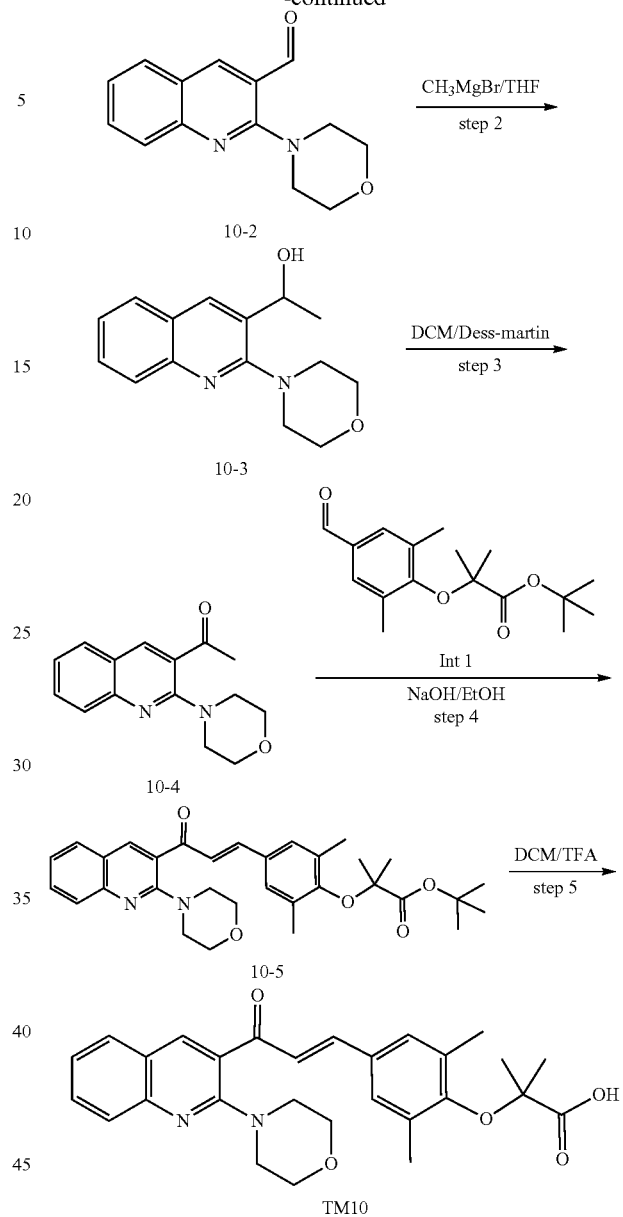

Step 1: Preparation of 2-(morpholin-4-yl)-3-formylquinoline (10-2)

To the compound 10-1 (1.0 g, 5.2 mmol) dissolved in DMF (15 mL) was added subsequently morpholine (1.4 g, 15.7 mmol) and potassium carbonate (3.6 g, 26.1 mmol). After 4 h at 90° C., the mixture was added with water and ethyl acetate for extraction. The organic phase was washed twice with saturated saline solution, dried and concentrated, and separated by column chromatography to obtain the target product 10-2 (750 mg) with a yield of 59.5%.

Step 2: Preparation of 1-(2-(morpholin-4-yl) quinolin-3-yl)-ethanol (10-3)

CH$_3$MgBr (1M) (4.7 mL, 4.7 mmol) was dissolved in THF (5 mL), and cooled in an ice-water bath for 10 min. To the above mixture was added dropwise 10-2 (750 mg, 3.1 mmol) dissolved in THF (10 mL). The reaction mixture was stirred for 2 h. No progression of the reaction was monitored by LC-MS, then the reaction mixture was poured into saturated aqueous solution of ammonium chloride, extracted with ethyl acetate. The organic phases were combined, washed once with saturated saline solution, dried with sodium sulfate, filtered and concentrated to obtain the target product 10-2 (800 mg crude), which was directly used in the next reaction without purification.

Steps 3, 4 and 5: Three-step synthesis of (E)-2-(4-(3-(2-(morpholin-4-yl) quinolin-3-yl)-3-oxo-1-propen-1-yl)-2,6-dimethylphenoxy)-2-methylpropionic acid (TM10)

Compound TM10 was synthesized via a method similar to that described in step 2 to step 4 of Example 4 with a yield of 25%, except that 10-3 is used in step 3 of Example 11 instead of 3-2 in step 2 of Example 4.

MS m/z (ESI): 475 [M+H]$^+$

1HNMR (400 MHz, DMSO-d6) δ: 12.97 (s, 1H), 8.40 (s, 1H), 7.93 (d, J=8.0 Hz, 1H), 7.80-7.68 (m, 2H), 7.62 (d, J=16.0 Hz, 1H), 7.50 (s, 2H), 7.45-7.35 (m, 2H), 3.70-3.50 (m, 4H), 3.40-3.30 (m, 4H), 2.20 (s, 6H), 1.38 (s, 6H).

Example 12: Preparation of (E)-2-(4-(3-(2-(S)-(3-hydroxypyrrolidin-1-yl) quinolin-3-yl)-3-oxo-1-propen-1-yl)-2,6-dimethylphenoxy)-2-methylpropionic acid (TM53)

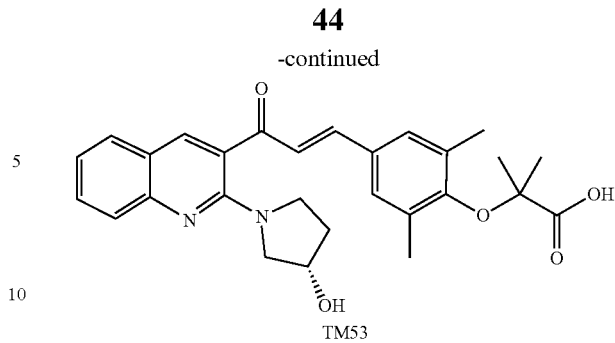

TM53

Compound TM53 was synthesized via a method similar to that described in step 1 to step 3 of Example 5 with a yield of 39%, except that (S)-3-hydroxypyrrolidine is used in step 1 of Example 12 instead of sodium methoxide compound in step 1 of Example 5.

MS m/z (ESI): 475 [M+H]$^+$

1 HNMR (400 MHz, DMSO-d6) δ: 8.40 (s, 1H), 7.86 (d, J=8.0 Hz, 2H), 7.67-7.65 (m, 2H), 7.60 (d, J=16.0 Hz, 1H), 7.52 (s, 2H), 7.34-7.30 (m, 2H), 4.33 (s, 1H), 3.62 (s, 2H), 3.47 (s, 2H), 3.12 (s, 1H), 2.20 (s, 6H), 1.98-1.86 (m, 2H), 1.38 (s, 6H).

Example 13: Preparation of (E)-2-(4-(3-(2-(R)-(3-hydroxypyrrolidin-1-yl)quinolin-3-yl)-3-oxo-1-propen-1-yl)-2,6-dimethylphenoxy)-2-methylpropionic acid (TM54)

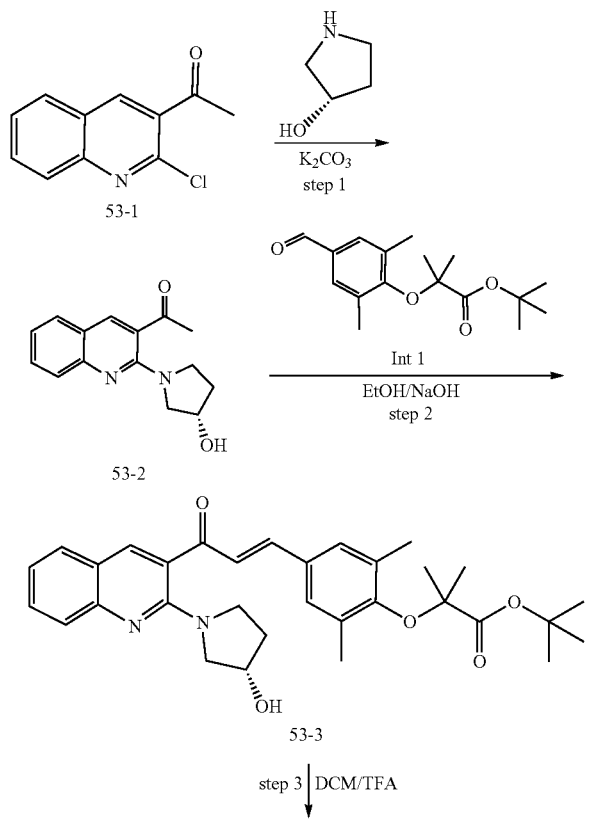

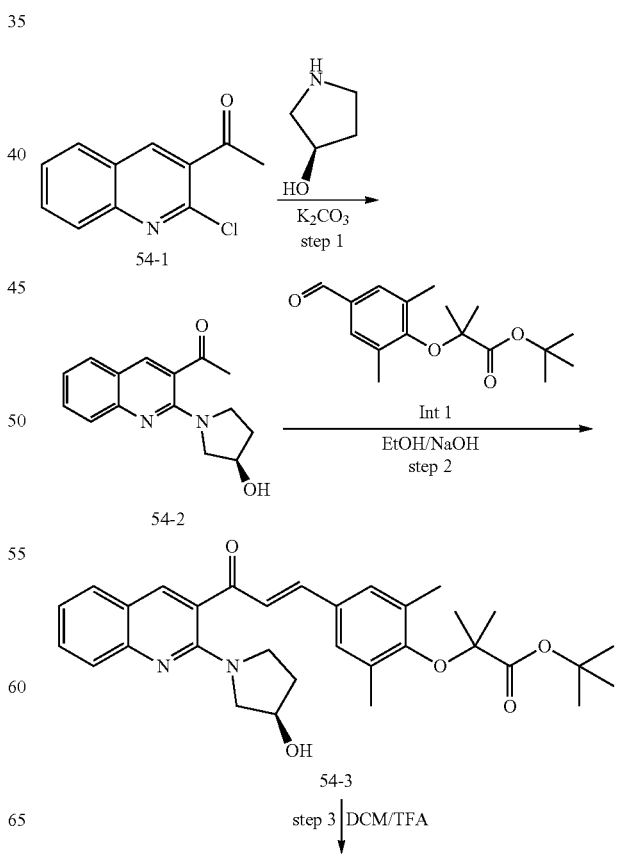

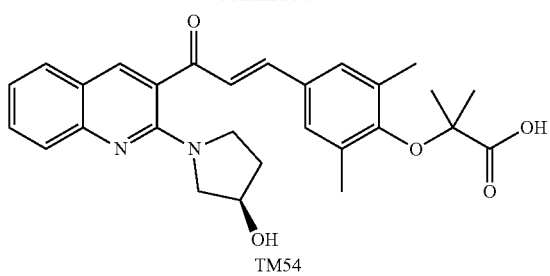

TM54

Compound TM54 was synthesized via a method similar to that described in step 1 to step 3 of Example 5 with a yield of 46%, except that (R)-3-hydroxypyrrolidine is used in step 1 of Example 13 instead of sodium methoxide compound in step 1 of Example 5.

MS m/z (ESI): 475 [M+H]$^+$

1 HNMR (400 MHz, DMSO-d6) δ: 8.44 (s, 1H), 7.87 (d, J=8.0 Hz, 1H), 7.72-7.67 (m, 2H), 7.62 (d, J=16.0 Hz, 1H), 7.52 (s, 2H), 7.34-7.30 (m, 2H), 4.34 (s, 1H), 3.64 (s, 2H), 3.50 (s, 2H), 3.14 (s, 1H), 2.20 (s, 6H), 1.98-1.87 (m, 2H), 1.38 (s, 6H).

Example 14: Preparation of (E)-2-(4-(3-(2-(4-hydroxypiperidin-1-yl) quinolin-3-yl)-3-oxo-1-propen-1-yl)-2,6-dimethylphenoxy)-2-methylpropionic acid (TM25)

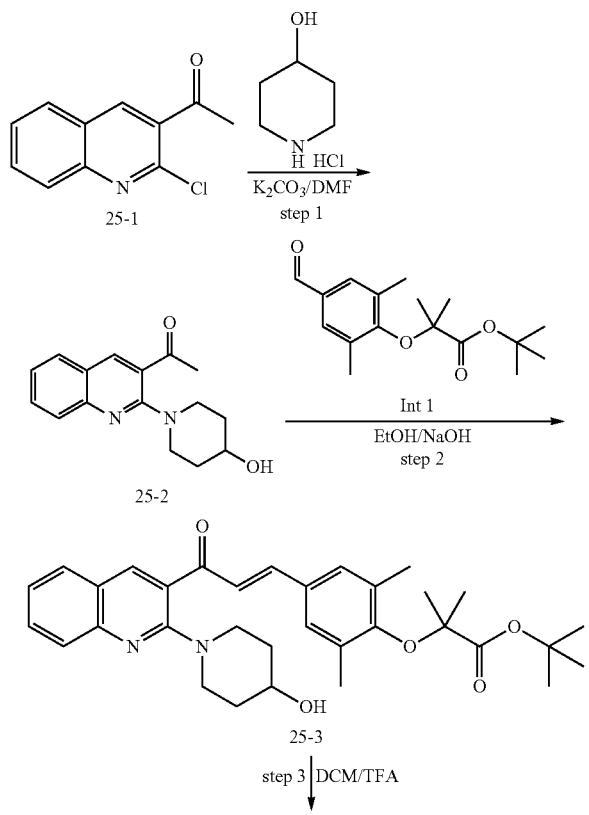

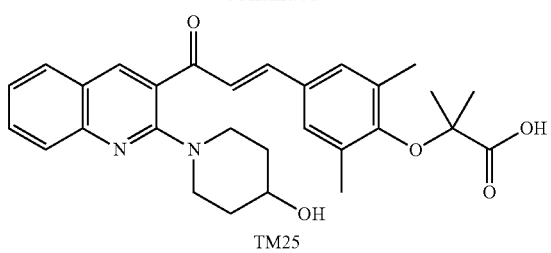

TM25

Compound TM25 was synthesized via a method similar to that described in step 1 to step 3 of Example 5 with a yield of 26%, except that 4-hydroxypiperidine hydrochloride is used in step 1 of Example 14 instead of sodium methoxide compound in step 1 of Example 5.

MS m/z (ESI): 489 [M+H]$^+$

1 HNMR (400 MHz, DMSO-d6) δ: 12.92 (s, 1H), 8.33 (s, 1H), 7.89 (d, J=16.0 Hz, 1H), 7.72-7.64 (m, 2H), 7.61 (d, J=16.0 Hz, 1H), 7.48 (s, 2H), 7.38-7.31 (m, 2H), 4.71 (d, J=2.0 Hz, 1H), 3.75-3.60 (m, 3H), 3.15-3.10 (m, 2H), 2.19 (s, 6H), 1.80-1.70 (m, 2H), 1.50-1.30 (m, 8H).

Example 15: Preparation of (E)-2-(4-(3-(2-hydroxyquinolin-3-yl)-3-oxo-1-prop en-1-yl)-2,6-dimethylphenoxy)-2-methylpropionic acid (TM12)

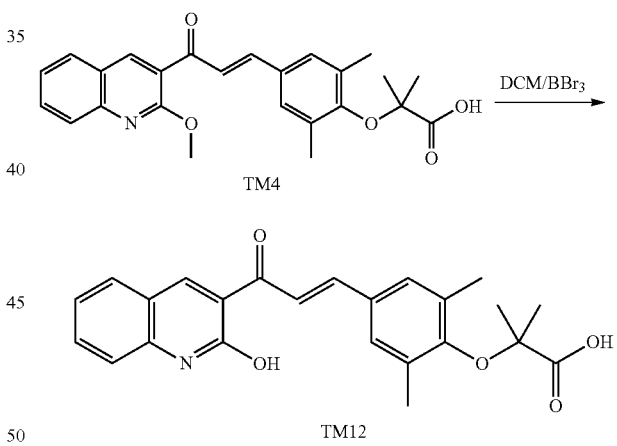

Compound TM4 (15 mg, 0.04 mmol) was dissolved in DCM (3 mL), and cooled in an ice-water bath for 10 min. To the mixture was added boron tribromide dissolved in dichloromethane (1 mL), and reacted for 30 min. After no progression of the reaction was monitored by LC-MS, the reaction solution was concentrated and purified by column chromatography to obtain the target product TM12 (5 mg) with a yield of 35%.

MS m/z (ESI): 406 [M+H]$^+$

1 HNMR (400 MHz, DMSO-d6) δ: 12.13 (s, 1H), 8.46 (s, 1H), 7.87 (d, J=4.0 Hz, 1H), 7.69 (d, J=16.0 Hz, 1H), 7.65-7.60 (m, 1H), 7.69 (d, J=16.0 Hz, 1H), 7.44-7.36 (m, 3H), 7.28-7.22 (m, 1H), 2.11 (s, 6H), 1.37 (s, 6H).

Example 16: Preparation of (E)-2-(4-(3-(2-(R)-(2,3-dihydroxypropylamino) quinolin-3-yl)-3-oxo-1-propen-1-yl)-2,6-dimethylphenoxy)-2-methylpropionic acid (TM11)

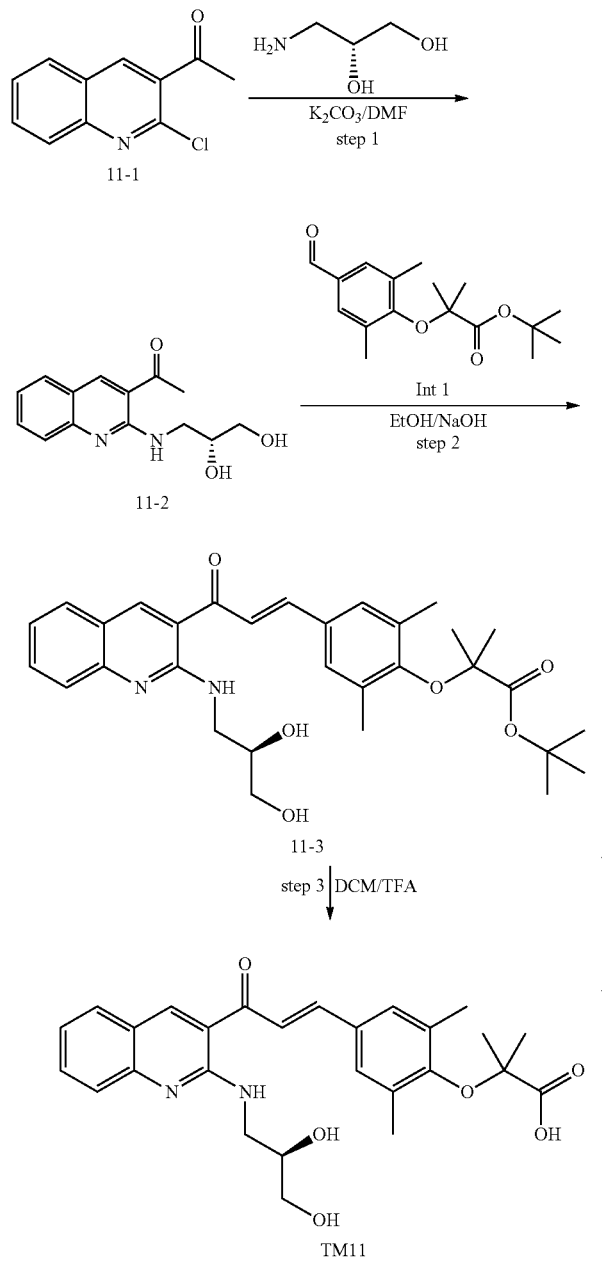

Compound TM11 was synthesized via a method similar to that described in step 1 to step 3 of Example 5 with a yield of 5%, except that (R)-3-amino-1,2-propanediol is used in step 1 of Example 16 instead of sodium methoxide compound in step 1 of Example 5.

MS m/z (ESI): 479 [M+H]+

1 HNMR (400 MHz, DMSO-d6) δ: 9.20 (s, 1H), 9.05-8.98 (m, 1H), 8.01 (d, J=16.0 Hz, 1H), 7.89 (d, J=4.0 Hz, 1H), 7.72-7.62 (m, 2H), 7.56 (s, 2H), 7.52 (d, J=4.0 Hz, 1H), 7.26 (t, J=7.2 Hz, 1H), 5.10 (d, J=2.0 Hz, 1H), 4.80 (t, J=4.0 Hz, 1H), 3.85-3.65 (m, 3H), 3.35-3.30 (m, 2H), 2.28 (s, 6H), 1.37 (s, 6H).

Example 17: Preparation of (E)-2-(4-(3-(2-methylthioquinolin-3-yl)-3-oxo-1-propen-1-yl)-2,6-dimethylphenoxy)-2-methylpropionic acid (TM13)

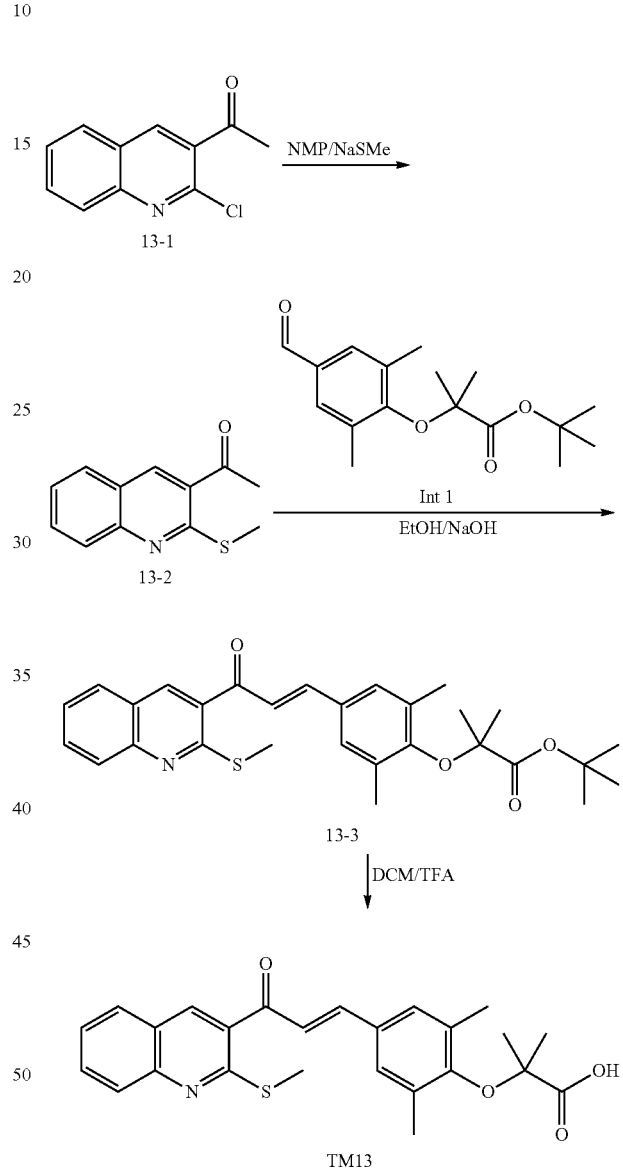

Compound TM13 was synthesized via a method similar to that described in step 1 to step 3 of Example 5 with a yield of 17%, except that, in step 1 of Example 17, sodium methoxide in step 1 of Example 5 is replaced with sodium methyl mercaptide, and methanol is replaced with NMP.

MS m/z (ESI): 436 [M+H]+

1 HNMR (400 MHz, DMSO-d6) δ: 12.97 (s, 1H), 8.97 (s, 1H), 8.09 (d, J=3.6 Hz, 1H), 7.95 (d, J=8.4 Hz, 1H), 7.90-7.82 (m, 1H), 7.68 (d, J=16.0 Hz, 1H), 7.64-7.52 (m, 4H), 2.58 (s, 3H), 2.22 (s, 6H), 1.39 (s, 6H).

Example 18: Preparation of (E)-2-(4-(3-(2-chloro-7-methoxy-quinolin-3-yl)-3-oxo-1-propen-1-yl)-2,6-dimethylphenoxy)-2-methylpropionic acid (TM29)

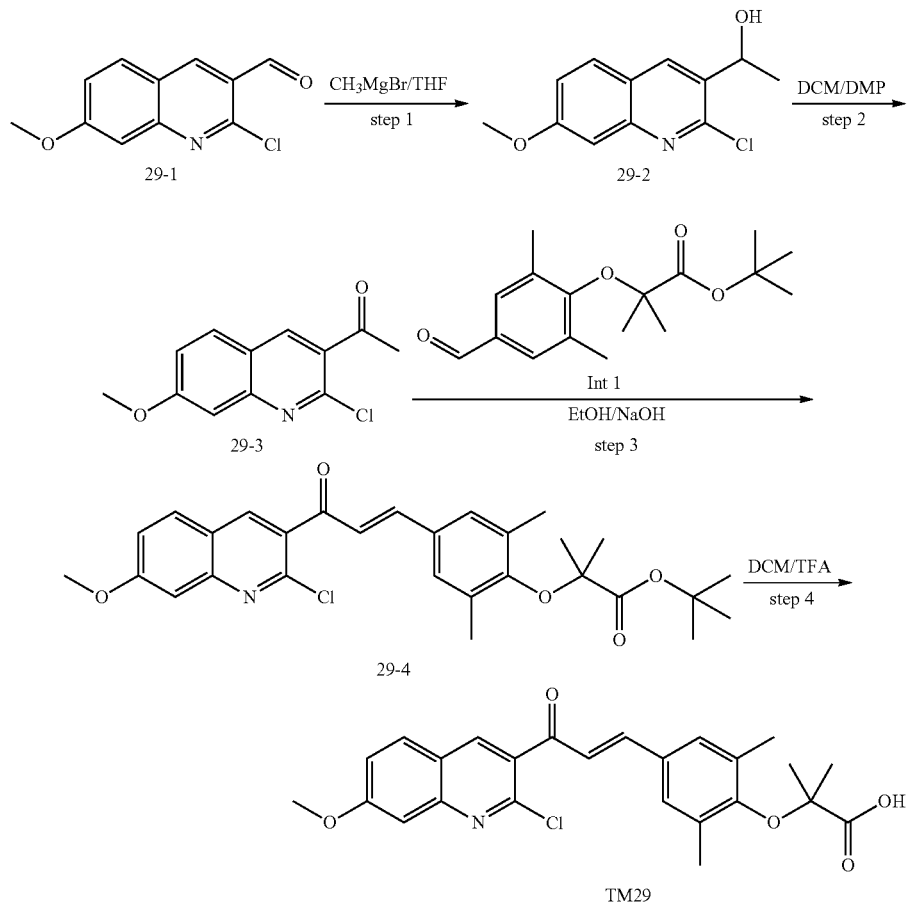

Compound TM29 was synthesized via a method similar to that described in step 1 to step 4 of Example 4 with a yield of 7%, except that 29-1 is used in step 1 of Example 18 instead of 3-1 in step 1 of Example 4.

MS m/z (ESI): 454 [M+H]$^+$
$^1$HNMR (400 MHz, DMSO-d6) δ: 8.64 (s, 1H), 8.07 (d, J=9.2 Hz, 1H), 7.50-7.41 (m, 4H), 7.40-7.36 (m, 1H), 7.28 (d, J=16.0 Hz, 1H), 3.97 (s, 3H), 2.22 (s, 6H), 1.33 (s, 6H).

Example 19: Preparation of (E)-2-(4-(3-(2,7-dimethoxy-quinolin-3-yl)-3-oxo-1-propen-1-yl)-2,6-dimethylphenoxy)-2-methylpropionic acid (TM28)

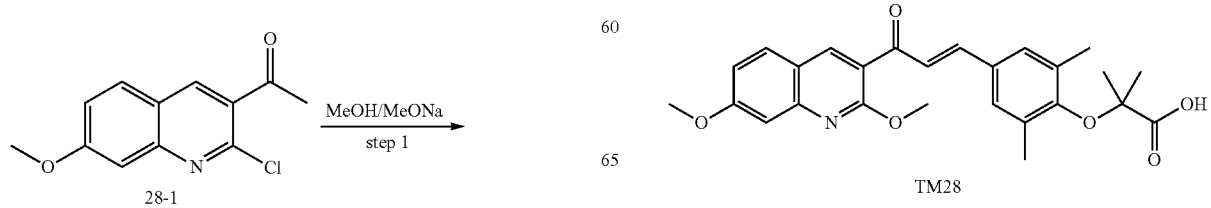

Compound TM28 was synthesized via a method similar to that described in step 1 to step 3 of Example 5 with a yield of 30%, except that 28-1 is used in step 1 of Example 19 instead of 4-1 in step 1 of Example 5.

MS m/z (ESI): 450 [M+H]⁺

1 HNMR (400 MHz, DMSO-d6) δ: 12.94 (s, 1H), 8.50 (s, 1H), 7.94 (d, J=8.0 Hz, 1H), 7.55-7.35 (m, 4H), 7.25-7.20 (m, 1H), 7.17-7.10 (m, 1H), 4.06 (s, 3H), 3.94 (s, 3H), 2.22 (s, 6H), 1.38 (s, 6H).

Example 20: Preparation of (E)-2-(4-(3-(2-chloro-6-methoxy-quinolin-3-yl)-3-oxo-1-prop en-1-yl)-2,6-dimethylphenoxy)-2-methylpropionic acid (TM27)

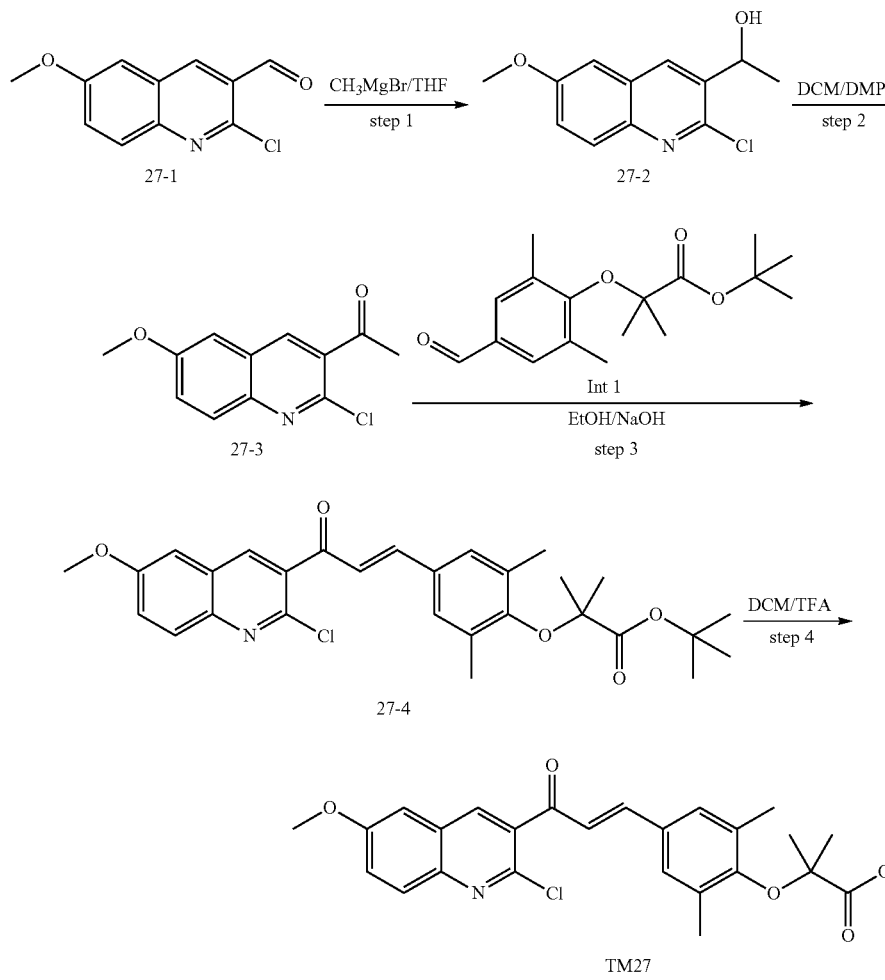

Compound TM27 was synthesized via a method similar to that described in step 1 to step 4 of Example 4 with a yield of 22%, except that 27-1 is used in step 1 of Example 20 instead of 3-1 in step 1 of Example 4.

MS m/z (ESI): 454 [M+H]⁺

1 HNMR (400 MHz, DMSO-d6) δ: 12.96 (s, 1H), 8.55 (s, 1H), 7.97 (d, J=8 Hz, 1H), 7.60-7.52 (m, 2H), 7.50 (s, 2H), 7.44 (d, J=16.0 Hz, 1H), 7.27 (d, J=16.0 Hz, 1H), 3.92 (s, 3H), 2.18 (s, 6H), 1.37 (s, 6H).

Example 21: Preparation of (E)-2-(4-(3-(2,6-dimethoxy-quinolin-3-yl)-3-oxo-1-propen-1-yl)-2,6-dimethyl phenoxy)-2-methylpropionic acid (TM26)

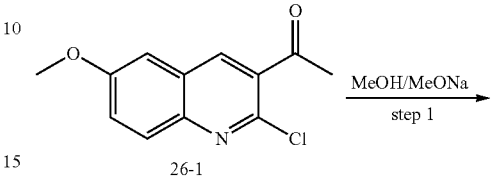

-continued

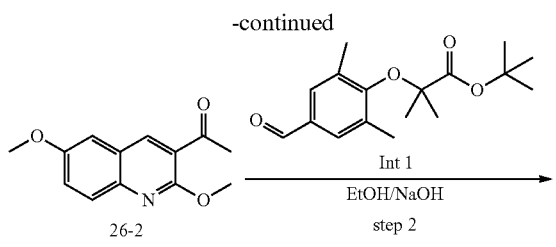

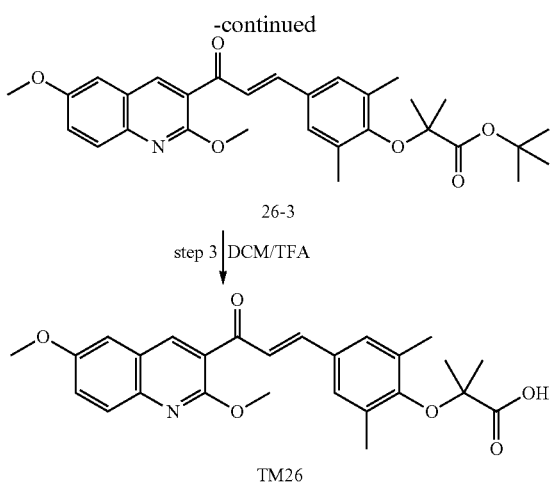

Compound TM26 was synthesized via a method similar to that described in step 1 to step 3 of Example 5 with a yield of 32%, except that 26-1 is used in step 1 of Example 21 instead of 4-1 in step 1 of Example 5.

MS m/z (ESI): 450 [M+H]+

$^1$HNMR (400 MHz, DMSO-d6) δ: 12.95 (s, 1H), 8.42 (s, 1H), 7.78 (d, J=8.0 Hz, 1H), 7.50-7.40 (m, 5H), 7.36 (d, J=16.0 Hz, 1H), 4.01 (s, 3H), 3.87 (s, 3H), 2.19 (s, 6H), 1.38 (s, 6H).

Example 22: Preparation of 2-(4-(3-(2-methoxyquinolin-3-yl)-3-oxopropyl)-2,6-dimethylphenoxy)-2-methylpropanoic acid (TM42)

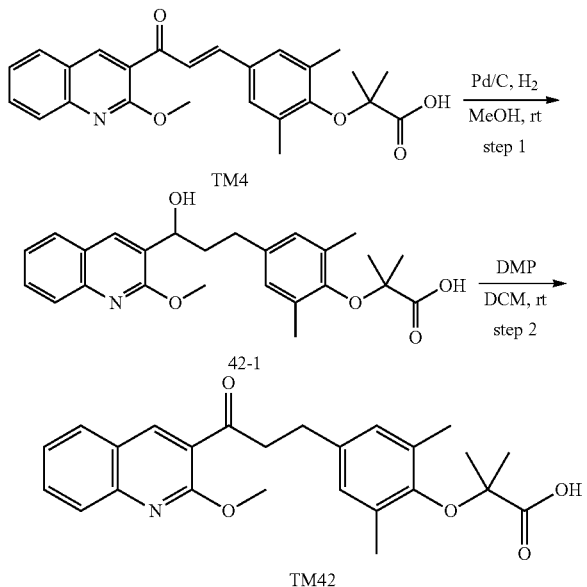

Step 1:

To a solution of TM4 (4.5 g, 10.73 mmol) obtained from Example 5 in MeOH (45 mL) was added 10% Pd/C (450 mg, 3.71 mmol) with stirring. The system was degassed under vacuum and purged with H$_2$ 3 times and reacted at room temperature for 16 h. The completion of the reaction was monitored by LC-MS. The system was subjected to diatomite filtration. The filtrate was concentrated and purified by silica gel column chromatography (DCM/MeOH=0-5%) and preparative HPLC (formic acid, acetonitrile/H$_2$O) to afford 2.0 g of compound 42-1 as a solid.

MS m/z (ESI): 424 [M+H]+

$^1$H NMR (400 MHz, DMSO-d6) δ 12.79 (s, 1H), 8.25 (s, 1H), 7.90 (d, J=8 Hz, 1H), 7.75 (d, J=8 Hz, 1H), 7.61 (t, J=8 Hz, 1H), 7.41 (t, J=8 Hz, 1H), 6.80 (s, 2H), 5.40 (br, 1H), 4.89-4.81 (m, 1H), 3.97 (s, 3H), 2.70-2.55 (m, 2H), 2.10 (s, 6H), 2.07-1.97 (m, 1H), 1.85-1.70 (m, 1H), 1.32 (s, 6H).

Step 2:

Compound 42-1 (1.7 g, 4.01 mmol) was added to DCM (34 mL), followed by an addition of DMP (3.41 g, 8.03 mmol) in batches. The resulting mixture was reacted for 3 h. Na$_2$SO$_3$ aqueous solution was added once the completion of reaction was detected by LC-MS. The mixture was extracted with DCM. The extract was concentrated and purified by silica gel column chromatography (DCM/MeOH=0-5%) and preparative HPLC (formic acid, acetonitrile/H$_2$O) to afford 480 mg of TM42 as a solid.

MS m/z (ESI): 422 [M+H]+

$^1$H NMR (400 MHz, DMSO-d6) δ 12.78 (s, 1H), 8.58 (s, 1H), 8.02 (d, J=8 Hz, 1H), 7.81 (d, J=8 Hz, 1H), 7.77 (t, J=8 Hz, 1H), 7.49 (t, J=8 Hz, 1H), 6.86 (s, 2H), 4.05 (s, 3H), 3.32 (t, J=8 Hz, 2H), 2.82 (t, J=8 Hz, 2H), 2.11 (s, 6H), 1.31 (s, 6H).

Pharmacological Test

Test example 1: Experiment of the compounds on activation of transient transfected PPAR α in HEK293 cells Reagent:

Plasmid: pcDNA3.1(+)-GAL4-hPPAR α, customized by Nanjing Kebai Biotechnology Co., Ltd.

Liposome: PGL4.35, customized by Nanjing Kebai Biotechnology Co., Ltd.

Cell: human embryonic kidney cells HEK293, purchased from ATCC.

Transfection reagent: Lipofectamine Reagent 3000 purchased from Invitrogen.

Assay kit: Bright Glo™ Luciferase Assay System purchased from Promega.

Testing Method:

HEK293 cells were incubated in DMEM medium containing 10% of fetal bovine serum at 37° C. in the presence of 5% of CO$_2$. 3×10$^5$/ml cells were plated in each well of the 6-well plate. When the cell convergence degree reached 50%-80%, 5 μg of liposome PGL4.35 and 5 μg of expression plasmid pcDNA3.1(+)-GAL4-hPPAR α were added to transfect the cells for 24 h and then the cells were collected. The transfected cells were plated in the 96-well plate and the compounds of the application in different concentrations were added, incubated for 24 h, and Bright Glo™ Luciferase Assay System reagent was added for luciferase assay. In cells transfected with plasmids and treated with compounds, luciferase activity was increased. The induction of luciferase activity indicated that the compound of the application is PPAR α agonist. EC$_{50}$ values of the compound of the application on transfected HEK293 cells were calculated by GraphPad software, and the results were shown in Table 1.

TABLE 1

Activation of transient transfected PPAR α in HEK293 cells

| Compound | EC$_{50}$ (nM) |
|---|---|
| Example 2 | 1211.46 |
| Example 3 | 1933.28 |
| Example 4 | 277.91 |

TABLE 1-continued

Activation of transient transfected PPAR α in HEK293 cells

| Compound | $EC_{50}$ (nM) |
|---|---|
| Example 5 | 28.32 |
| Example 6 | 52.81 |
| Example 7 | 751.92 |
| Example 8 | 691.69 |
| Example 9 | 307.29 |
| Example 10 | 76.95 |
| Example 11 | 584.93 |
| Example 17 | 122.57 |
| Example 18 | 8.62 |
| Example 19 | 1.33 |
| Example 20 | 459.85 |
| Example 21 | 5.40 |

As indicated in the data in Table 1, the compound of the application has strong agonist activity on PPAR α: $EC_{50}$ of the test compound is less than 2 μM.

Test Example 2: Experiment of the Compounds on Activation of Transient Transfected PPAR δ in HEK293 Cells Reagent:
Plasmid: pcDNA3.1(+)-GAL4-hPPAR δ, customized by Nanjing Kebai Biotechnology Co., Ltd.
Liposome: PGL4.35, customized by Nanjing Kebai Biotechnology Co., Ltd.
Cell: human embryonic kidney cells HEK293, purchased from ATCC.
Transfection reagent: Lipofectamine Reagent 3000 purchased from Invitrogen.
Assay kit: Bright Glo™ Luciferase Assay System purchased from Promega.
Testing Method:
HEK293 cells were incubated in DMEM medium containing 10% of fetal bovine serum at 37° C. in the presence of 5% of $CO_2$. $3\times10^5$/ml cells were plated in each well of the 6-well plate. When the cell convergence degree reached 50%-80%, 5 μg of liposome PGL4.35 and 5 μg of expression plasmid pcDNA3.1(+)-GAL4-hPPAR δ were added to transfect the cells for 24 h and then the cells were collected. Then, the transfected cells were plated in the 96-well plate and the compounds of the application in different concentrations were added, incubated for 24 h, and Bright Glo™ Luciferase Assay System reagent for luciferase assay was added. In cells transfected with plasmids and treated with compounds, luciferase activity was increased. The induction of luciferase activity indicated that the compound of the application is PPAR δ agonist. $EC_{50}$ value of the compound of the application on transfected HEK293 cells were calculated by GraphPad software, and the results were shown in Table 2.

TABLE 2

Activation of transient transfected PPAR δ in HEK293 cells

| Compound | $EC_{50}$ (nM) |
|---|---|
| Example 2 | 6130.95 |
| Example 4 | 3441.71 |
| Example 5 | 555.77 |
| Example 6 | 373.60 |
| Example 9 | 6699.54 |
| Example 10 | 2510.76 |
| Example 11 | 4426.63 |
| Example 18 | 809.57 |
| Example 19 | 795.87 |
| Example 21 | 674.55 |

As indicated in the data in Table 2, the compound of the application has strong agonist activity on PPAR δ: $EC_{50}$ of the test compound is less than 10 μM.

Test Example 3: Experiment of Compounds on Activation of PPAR α, δ and γ in Genetically Engineered CHO-K1 Cells Reagent:
Cell: PathHunter® CHO-K1 PPARα Protein Interaction Cell Line, PathHunter® CHO-K1 PPARδ Protein Interaction Cell Line and PathHunter® CHO-K1 PPARγ Protein Interaction Cell Line, provided by DiscoverX®.
Assay kit: PathHunter® Detection Kit, provided by DiscoverX®.
Testing Method:
1) Cell Handling: PathHunter NHR (nuclear hormone receptor, PPARα, δ, γ) cell lines were expanded from freezer stocks according to standard procedures. Cells were seeded in a total volume of 20 μL into white walled, 384-well microplates and incubated at 37° C., 5% $CO_2$ for the appropriate time prior to testing. Assay media contained charcoal-dextran filtered serum to reduce the level of hormones present.
2) Agonist Format: For agonist determination, cells were incubated with sample to induce response.
Intermediate dilution of sample stocks was performed to generate 5× sample in assay buffer. 5 μL of 5× test compounds in different concentrations were added to the 384-well Plate to reach a final concentration of 30 μM, 10 μM, 3 μM, 1 μM, 0.3 μM, 0.1 μM, 0.03 μM, 0.01 μM, 0.003 μM and 0.001 μM, respectively, and incubated at 37° C. For 6 hours. Final assay vehicle (DMSO) concentration was 1%.
3) Signal detection: Assay signal was generated through a single addition of 12.5 or 15 μL (50% v/v) of PathHunter Detection reagent cocktail, followed by one-hour-incubation at room temperature. Microplates were read following signal generation with a PerkinElmer Envision™ instrument for chemiluminescent signal detection.
4) Data analysis: Both compound activity and $EC_{50S}$ were analyzed using CBIS data analysis suite (ChemInnovation, CA). For agonist mode assays, percentage activity was calculated using the following formula: % Activity=100%× (mean RLU of test sample−mean RLU of vehicle control)/ (mean MAX control ligand−mean RLU of vehicle control).
Results:
$EC_{50}$ (μM) of TM4 is 0.023 on activation of PPARα; $EC_{50}$ (μM) of TM4 is 0.797 on activation of PPARδ; and $EC_{50}$ (μM) of TM4 is 0.174 on activation of PPARγ.
$EC_{50}$ (μM) of TM42 is 0.063 on activation of PPARα; $EC_{50}$ (μM) of TM42 is 0.496 on activation of PPARδ; and $EC_{50}$ (μM) of TM42 is 1.947 on activation of PPARγ.
From the above results, it is indicated that compounds of the invention (e.g., TM4, TM42) have significant agonistic activity on PPARα, and can also activate PPARδ and PPARγ to some extent. Thus, compounds of the invention have selective agonistic activity on PPARα.

Test Example 4: Cytotoxicity Test of Compound on HepG2 & Hek293 Cells

Reagent:
Cells: human hepatocyte HepG2, purchased from ATCC;
Human embryonic kidney cells HEK293: purchased from ATCC;

Assay reagent: CellTiter Glo® Luminescent Cell Viability Assay, purchased from Promega.

Testing Method:

HepG2 and HEK293 cells were incubated in DMEM/F12 medium containing 10% of fetal bovine serum respectively. A proper amount of cells were plated into a 96-well plate, the plate was placed in an incubator overnight, and the culture medium was removed, and replaced with a complete culture medium containing the compound of the application, and incubated for 3 days. On day 4, an assay reagent CellTiter Glo was added to each well, and the relative luminous unit (RLU) of each well was determined by chemiluminescence. $CC_{50}$ values of the compound of the application to HepG2 and HEK293 cells were calculated by GraphPad software, and the results were shown in Table 3.

TABLE 3

Cytotoxic effect of compound on HepG2 & HEK293 cells

| Compound | HepG2-$CC_{50}$ (μM) | HEK293-$CC_{50}$ (μM) |
| --- | --- | --- |
| Example 2 | ~7.27 | ~8.14 |
| Example 4 | 11.33 | 13.57 |
| Example 5 | 12.96 | 7.13 |
| Example 6 | >10 | >10 |
| Example 7 | >10 | >10 |
| Example 8 | >10 | >10 |

As indicated from the data in Table 3, $CC_{50}$ of toxicity of the compound of the invention to HepG2 cells and HEK293 cells was of μM grade. All test compounds were less cytotoxic to HepG2 cells and HEK293 cells.

Test Example 5: In Vitro Safety Test

The effect of the compound on hERG potassium ion channel was tested by Predictor™ hERG fluorescence polarization. The test results were shown in Table 4:

TABLE 4 hERG test results

| Compound | $IC_{50}$ (μM) |
| --- | --- |
| Example 2 | 8.24 |
| Example 3 | >10 |
| Example 4 | >10 |
| Example 5 | >10 |
| Example 6 | >10 |
| Example 8 | >10 |

TABLE 4-continued hERG test results

| Compound | $IC_{50}$ (μM) |
| --- | --- |
| Example 9 | >10 |
| Example 10 | >10 |
| Example 17 | >10 |
| Example 18 | >10 |
| Example 19 | >10 |
| Example 21 | >10 |

As indicated from the results in Table 4, $IC_{50}$ of the compound of the invention for hERG was greater than 8 μM. Therefore, the compound of the invention had no obvious inhibitory effect on hERG, nor potential safety hazard causing prolongation of cardiac QT interval.

Test Example 6: In Vivo Efficacy Study of Compound in the MCD Model of Non-Alcoholic Steatohepatitis In this example, comparative test between compound GFT505 from WO2018133705A1 and compounds of the invention was conducted, so as to show the advantages of compounds of the invention.

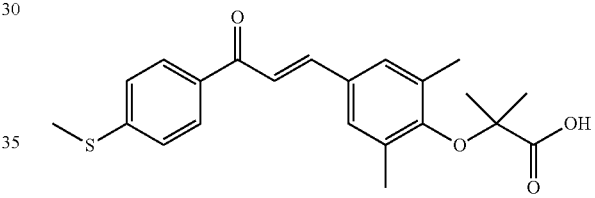

GFT505

Method:

C57 Mice at 8-10 weeks of age (purchased from Vital River Laboratories) were body-weight matched and randomly divided into groups of normal, model, control and test. Mice in normal group were fed with standard chow for 9 weeks. Mice in model group, control group and test group were fed with MCD diet (Methionine-Choline Deficient Diet, Research Diets) for 9 weeks to induce NASH Model. During weeks 5-9 of the 9-week course of MCD diet, the control group and the test group were treated with GFT505 and TM4 of the invention, respectively, and the normal group and model group were treated with 0.5% MC. The dosage regimen was specified in table 5.

TABLE 5 dosage regimen

| Groups | Numbers of animals | vehicle | drug | dose (mg/kg) | Volume (ml/kg) | Administration period and frequency | Administration route |
| --- | --- | --- | --- | --- | --- | --- | --- |
| normal | 5 | 0.5% MC | / | / | 10 | Once every day, for 35 days | intragastric administration |
| model | 12 | 0.5% MC | / | / | 10 | | |
| control | 12 | 0.5% MC | GFT505 | 1 | 10 | | |
| test | 12 | 0.5% MC | TM4 | 1 | 10 | | |

Animals were dissected after administration on day 35, livers were collected for H&E staining (hematoxylin-eosin staining) and sirius red staining. And then NAFLD activity score, including liver steatosis score, inflammation score and ballooning score, and liver fibrosis score were conducted. Results were shown in table 6.

TABLE 6 results of NAFLD activity score and liver fibrosis score

| Groups | NAFLD activity score (Mean ± SD) | Liver fibrosis score (Mean ± SD) |
|---|---|---|
| normal | 0.60 ± 0.54 | 0.20 ± 0.45 |
| model | 4.67 ± 1.16[a] | 1.83 ± 0.72[a] |
| control | 3.33 ± 0.87 | 1.22 ± 0.44 |
| test | 3.00 ± 0.93[b] | 0.88 ± 0.35[b] |

[a] $p < 0.05$, compared to normal group;
[b] $p < 0.05$, compared to model group Results:

It can be seen from the above table that, both NAFLD activity score and liver fibrosis score of model group are significantly higher than those of normal group ($p<0.05$), indicating NASH Model was successfully established. As described in Table 6, test group showed a significant reduction in both NAFLD activity score and liver fibrosis score compared with the model group ($p<0.05$), suggesting that compounds of the invention (e.g. TM4) exert an positive effect on NASH. Even though GFT505 showed a trend in the reduction of the NAS and fibrosis score compared with model group, the difference between the scores of GFT505 and model group is not statistically significant ($p>0.05$), indicating control compound GFT505 can not decrease NAFLD activity score and liver fibrosis score.

From the above, compared to control compound GFT505, compounds of the invention (e.g. TM4) have apparent advantages in improving NASH.

In addition to those described herein, various modifications of the invention will be apparent to those skilled in the art from the foregoing description. Such modifications are also intended to fall within the scope of the appended claims. All references cited in this application (including all patents, patent applications, journal articles, books and any other publications) are incorporated herein by reference in their entirety.

The invention claimed is:

1. A compound or a pharmaceutically acceptable salt, ester, stereoisomer, tautomer, polymorph, solvate, N-oxide, isotope-labeled compound, metabolite or prodrug thereof, wherein the compound has the structure of Formula (I)-1, Formula (I)-2 or Formula (I)-3:

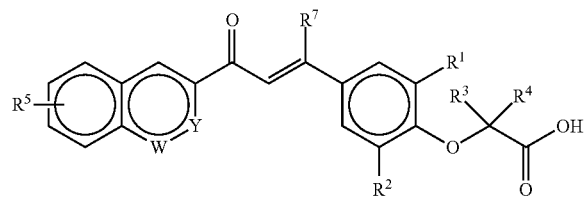

Formula (I)-1

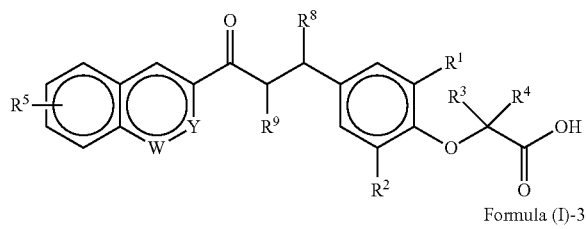

Formula (I)-2

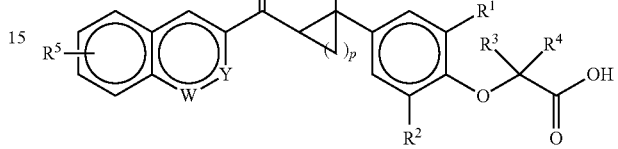

Formula (I)-3 wherein:
$R^1$, $R^2$, $R^3$ and $R^4$ in each formula are each independently selected from the group consisting of H, halogen, —OH, —SH, cyano, $C_{1-6}$ alkyl, $C_{3-6}$ cycloalkyl, halogenated $C_{1-6}$ alkyl, $C_{2-5}$ alkenyl, —O—[($C_{1-6}$ alkylene)-O]$_n$—($C_{1-6}$ alkyl), —S—($C_{1-6}$ alkyl), —NH$_2$, —NH—($C_{1-6}$ alkyl), —N($C_{1-6}$ alkyl)$_2$ and 3-10 membered heterocyclyl; or, $R^3$ and $R^4$ are connected to form $C_{3-6}$ cycloalkyl or 3-10 membered heterocyclyl;

Y in each formula is independently selected from a bond, N and C-$R^6$;

W in each formula is independently selected from N, and S;

$R^5$ in each formula is independently selected from the group consisting of H, halogen, —OH, —SH, cyano, nitro, $C_{1-6}$ alkyl, $C_{3-6}$ cycloalkyl, $C_{2-5}$ alkenyl, —O—[($C_{1-6}$ alkylene)-O]$_n$—($C_{1-6}$ alkyl), —O—($C_{3-6}$ cycloalkyl), —O-(3-6 membered heterocyclyl), —S(O)$_m$—($C_{3-6}$ cycloalkyl), —S(O)$_m$-(3-10 membered heterocyclyl), —NH$_2$, —NH—($C_{1-6}$ alkyl), —N($C_{1-6}$ alkyl)$_2$, 3-10 membered heterocyclyl, $C_{6-14}$ aryl and 5-14 membered heteroaryl; optionally, the $C_{1-6}$ alkyl, cycloalkyl, heterocyclyl, $C_{6-14}$ aryl, and 5-14 membered heteroaryl are each independently substituted by one or more substituents selected from the group consisting of halogen, —OH, —OC$_{1-6}$ alkyl, halogenated $C_{1-6}$ alkyl, —O-halogenated $C_{1-6}$ alkyl, —SH, —SC$_{1-6}$ alkyl, —NH$_2$, —NH—($C_{1-6}$ alkyl), and —N ($C_{1-6}$ alkyl)$_2$;

$R^6$ in each formula is independently selected from the group consisting of H, halogen, —OH, —SH, cyano, nitro, $C_{1-6}$ alkyl, $C_{3-6}$ cycloalkyl, $C_{2-5}$ alkenyl, —S(O)$_m$—($C_{1-6}$ alkyl), —O—[($C_{1-6}$ alkylene)-O]$_n$— ($C_{1-6}$ alkyl), —O—($C_{3-6}$ cycloalkyl), —O-(3-6 membered heterocyclyl), —S(O)$_m$—($C_{3-6}$ cycloalkyl), —S(O)$_m$-(3-10 membered heterocyclyl), —NH$_2$, —NH—($C_{1-6}$ alkyl), —N($C_{1-6}$ alkyl)$_2$, 3-10 membered heterocyclyl, $C_{6-14}$ aryl and 5-14 membered heteroaryl; optionally, the $C_{1-6}$ alkyl, cycloalkyl, heterocyclyl, $C_{6-14}$ aryl, and 5-14 membered heteroaryl are each independently substituted by one or more substituents selected from the group consisting of halogen, —OH, —OC$_{1-6}$ alkyl, halogenated $C_{1-6}$ alkyl, —O-halogenated $C_{1-6}$ alkyl, —SH, —SC$_{1-6}$ alkyl, —NH$_2$, —NH—($C_{1-6}$ alkyl), and —N($C_{1-6}$ alkyl)$_2$;

m in each formula is any integer from 0 to 2, and n in each formula is any integer from 0 to 10;

$R^7$ in Formula (I)-1 or (I)-3 is independently selected from the group consisting of H, halogen, $C_{1-6}$ alkyl, halogenated $C_{1-6}$ alkyl, $C_{3-6}$ cycloalkyl, —O—($C_{1-6}$ alkyl), 3-10 membered heterocyclyl, $C_{6-14}$ aryl and 5-14 membered heteroaryl;

$R^8$ and $R^9$ in Formula (I)-2 are each independently selected from the group consisting of H, halogen, $C_{1-6}$ alkyl, halogenated $C_{1-6}$ alkyl, $C_{3-6}$ cycloalkyl, —O—($C_{1-6}$ alkyl), 3-10 membered heterocyclyl, $C_{6-14}$ aryl and 5-14 membered heteroaryl;

P in Formula (I)-3 is 1 or 2.

2. The compound or the pharmaceutically acceptable salt, ester, stereoisomer, tautomer, polymorph, solvate, N-oxide, isotope-labeled compound, metabolite or prodrug thereof according to claim 1, wherein, $R^1$, $R^2$, $R^3$ and $R^4$ are each independently selected from the group consisting of H, halogen, $C_{1-6}$ alkyl, halogenated $C_{1-6}$ alkyl, and —O—[($C_{1-6}$ alkylene)-O]$_n$—($C_{1-6}$ alkyl), wherein n is any integer from 0 to 10.

3. The compound or the pharmaceutically acceptable salt, ester, stereoisomer, tautomer, polymorph, solvate, N-oxide, isotope-labeled compound, metabolite or prodrug thereof according to claim 1, wherein Y is selected from a bond and C-$R^6$;

W is selected from N and S.

4. The compound or the pharmaceutically acceptable salt, ester, stereoisomer, tautomer, polymorph, solvate, N-oxide, isotope-labeled compound, metabolite or prodrug thereof according to claim 1, wherein $R^5$ is selected from the group consisting of H, halogen, —OH, $C_{1-6}$ alkyl, $C_{3-6}$ cycloalkyl, —O—[($C_{1-6}$ alkylene)-O]$_n$—($C_{1-6}$ alkyl), —O—($C_{3-6}$ cycloalkyl), —O-(3-6 membered heterocyclyl), —NH$_2$, —NH—($C_{1-6}$ alkyl), —N($C_{1-6}$ alkyl)$_2$ and 3-6 membered heterocyclyl, wherein the $C_{1-6}$ alkyl, $C_{3-6}$ cycloalkyl and 3-6 membered heterocyclyl are optionally substituted by one or more substituents selected from the group consisting of halogen, —OH, —O$C_{1-3}$ alkyl, —SH, —S$C_{1-3}$ alkyl, —NH$_2$, —NH—($C_{1-3}$ alkyl) and —N($C_{1-3}$ alkyl)$_2$; m is 0, 1 or 2, and n is 0, 1, 2, 3, 4, or 5;

$R^6$ is selected from the group consisting of H, halogen, —OH, $C_{1-6}$ alkyl, $C_{3-6}$ cycloalkyl, —S(O)$_m$—($C_{1-6}$ alkyl), —O—[($C_{1-6}$ alkylene)-O]$_n$—($C_{1-6}$ alkyl), —O—($C_{3-6}$ cycloalkyl), —O-(3-6 membered heterocyclyl), —NH$_2$, —NH—($C_{1-6}$ alkyl), —N($C_{1-6}$ alkyl)$_2$ and 3-6 membered heterocyclyl, wherein the $C_{1-6}$ alkyl, $C_{3-6}$ cycloalkyl and 3-6 membered heterocyclyl are optionally substituted by one or more substituents selected from the group consisting of halogen, —OH, —O$C_{1-3}$ alkyl, —SH, —S$C_{1-3}$ alkyl, —NH$_2$, —NH—($C_{1-3}$ alkyl) and —N($C_{1-3}$ alkyl)$_2$; m is 0, 1 or 2, and n is 0, 1, 2, 3, 4, or 5.

5. The compound or the pharmaceutically acceptable salt, ester, stereoisomer, tautomer, polymorph, solvate, N-oxide, isotope-labeled compound, metabolite or prodrug thereof according to claim 1, wherein $R^1$, $R^2$, $R^3$ and $R^4$ are methyl.

6. The compound or the pharmaceutically acceptable salt, ester, stereoisomer, tautomer, polymorph, solvate, N-oxide, isotope-labeled compound, metabolite or prodrug thereof according to claim 1, wherein $R^5$ is selected from H and —O—[($C_{1-2}$ alkylene)—O]$_n$—($C_{1-3}$ alkyl), and n is 0, 1 or 2.

7. The compound or the pharmaceutically acceptable salt, ester, stereoisomer, tautomer, polymorph, solvate, N-oxide, isotope-labeled compound, metabolite or prodrug thereof according to claim 1, wherein $R^6$ is selected from the group consisting of H, F, Cl, —OH, $C_{1-3}$ alkyl, —SCH$_3$, —O—[($C_{1-2}$ alkylene)-O—]$_n$—($C_{1-3}$ alkyl), —N($C_{1-3}$ alkyl)$_2$ and 5-6 membered heterocycloalkyl, wherein the $C_{1-3}$ alkyl and 5-6 membered heterocycloalkyl are optionally substituted with 1-3 substituents selected from F, Cl, —OH and —OCH$_3$; n is 0, 1 or 2.

8. The compound or the pharmaceutically acceptable salt, ester, stereoisomer, tautomer, polymorph, solvate, N-oxide, isotope-labeled compound, metabolite or prodrug thereof according to claim 1, wherein $R^7$ in Formula (I)-1 or (I)-3 is independently selected from H, halogen and $C_{1-6}$ alkyl.

9. The compound or the pharmaceutically acceptable salt, ester, stereoisomer, tautomer, polymorph, solvate, N-oxide, isotope-labeled compound, metabolite or prodrug thereof according to claim 1, wherein $R^7$ in Formula (I)-1 or (I)-3 is independently H or methyl.

10. The compound or the pharmaceutically acceptable salt, ester, stereoisomer, tautomer, polymorph, solvate, N-oxide, isotope-labeled compound, metabolite or prodrug thereof according to claim 1, wherein $R^8$ and $R^9$ in Formula (I)-2 are each independently selected from H, halogen and $C_{1-6}$ alkyl.

11. The compound or the pharmaceutically acceptable salt, ester, stereoisomer, tautomer, polymorph, solvate, N-oxide, isotope-labeled compound, metabolite or prodrug thereof according to claim 1, wherein $R^8$ and $R^9$ in Formula (I)-2 are H.

12. The compound or the pharmaceutically acceptable salt, ester, stereoisomer, tautomer, polymorph, solvate, N-oxide, isotope-labeled compound, metabolite or prodrug thereof according to claim 1, wherein the compound is selected from:

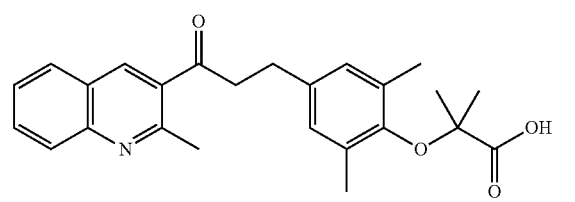

TM39

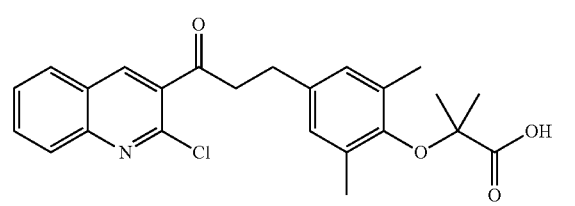

TM40

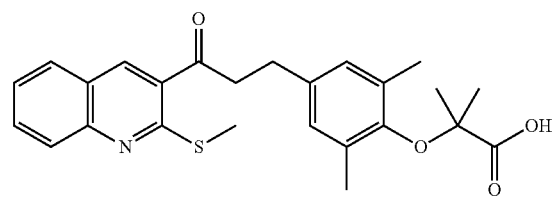

TM41

-continued
TM42
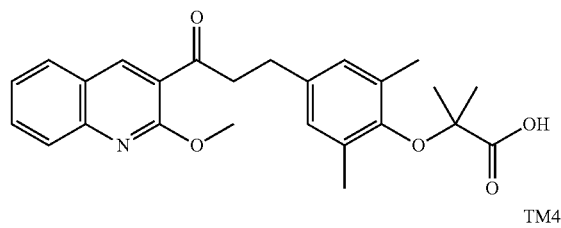
TM43
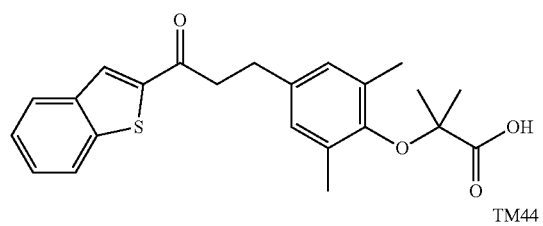
TM44
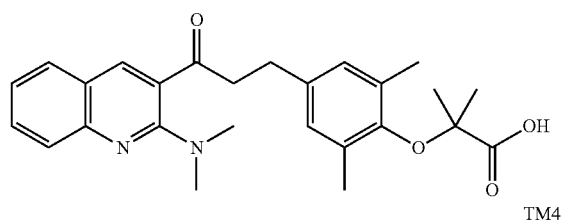
TM45
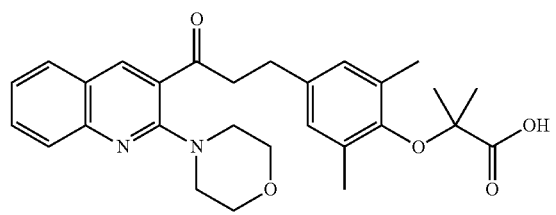
TM46
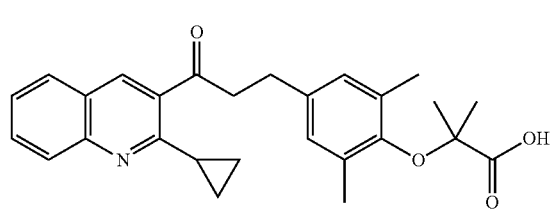
TM47
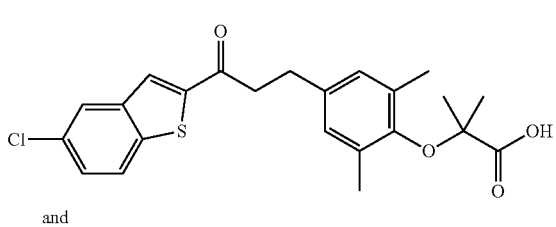
and
TM48
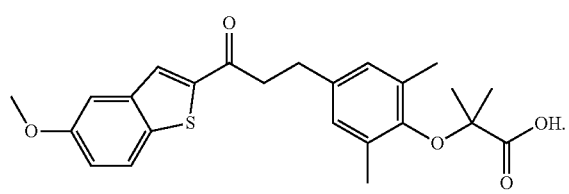
13. The compound or the pharmaceutically acceptable salt, ester, stereoisomer, tautomer, polymorph, solvate, N-oxide, isotope-labeled compound, metabolite or prodrug thereof according to claim 1, wherein the compound is selected from:
TM1
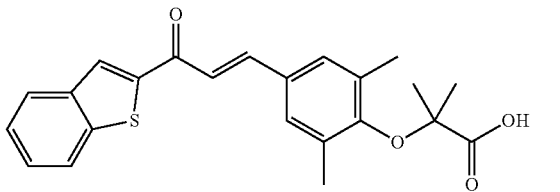
TM2
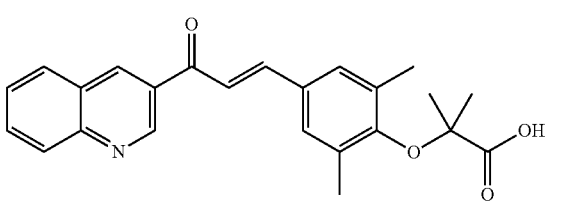
TM3
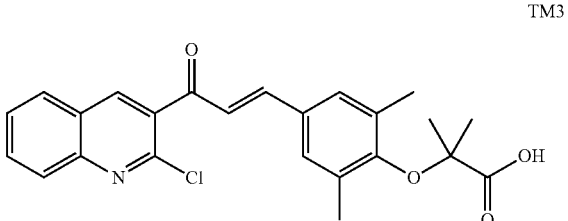
TM4
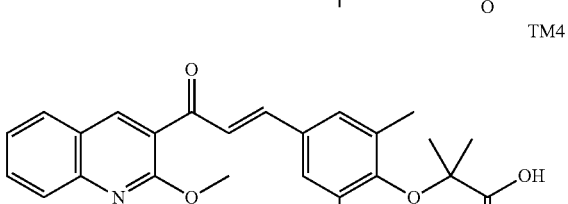
TM5
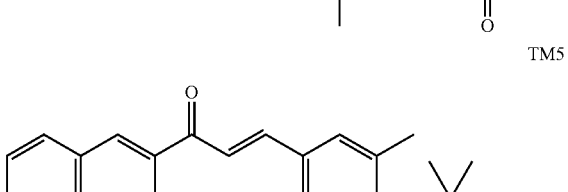
TM6
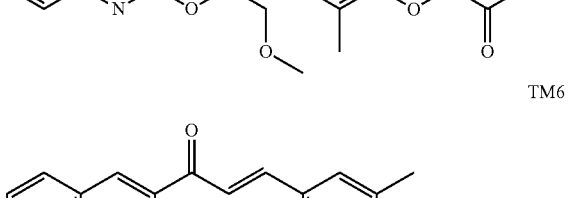
TM7
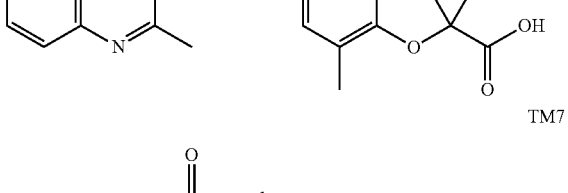

TM8
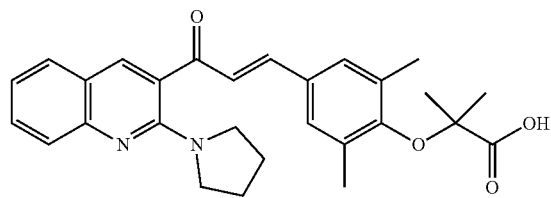
TM14
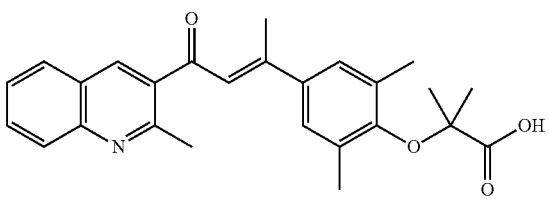
TM9
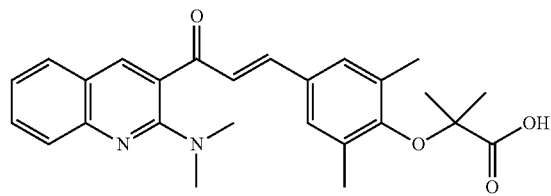
TM15
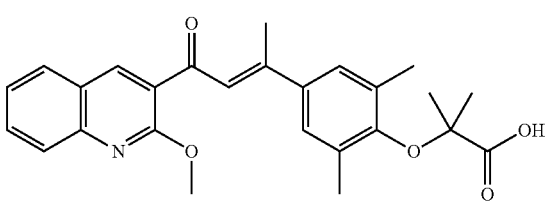
TM10
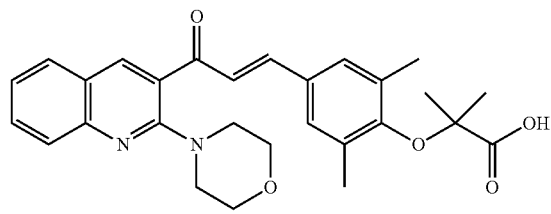
TM16
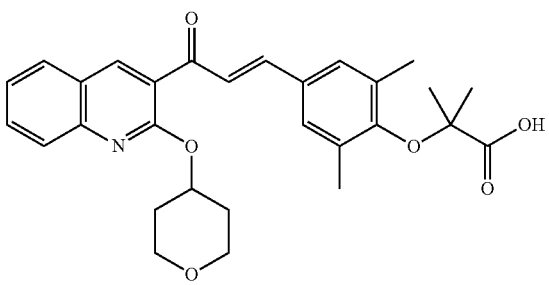
TM11
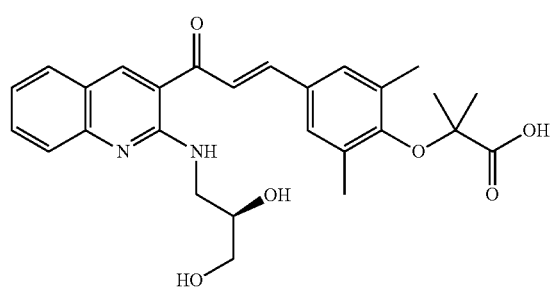
TM17
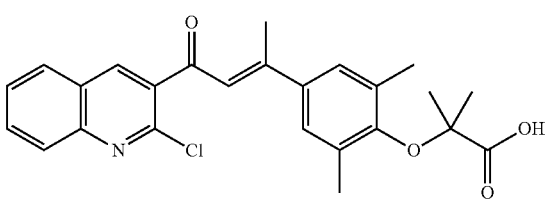
TM12
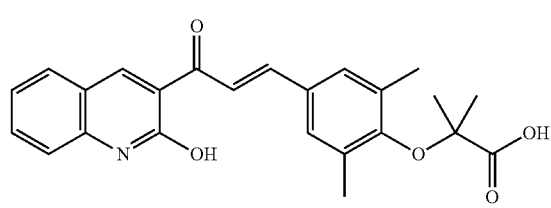
TM18
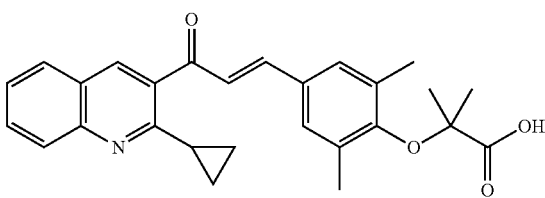
TM13
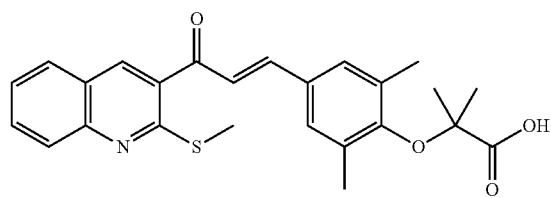
TM19

TM20
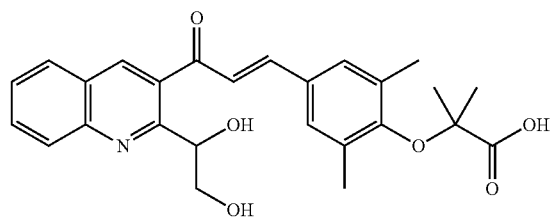
TM21
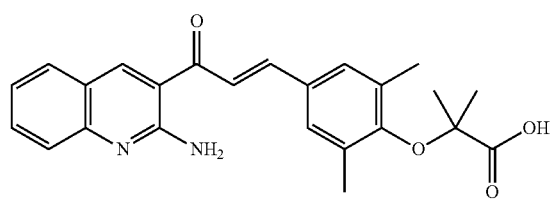
TM22
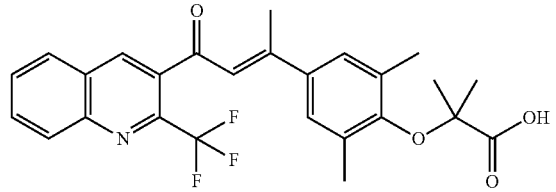
TM23
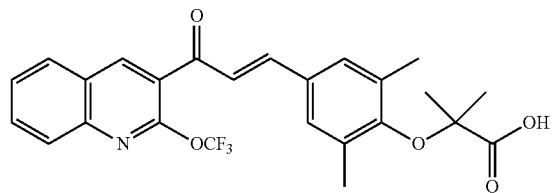
TM24
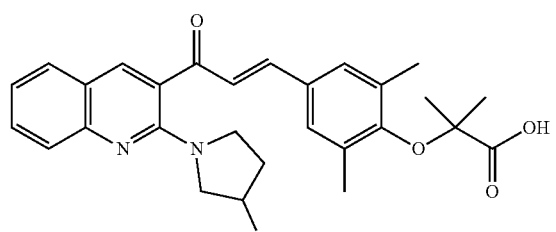
TM25
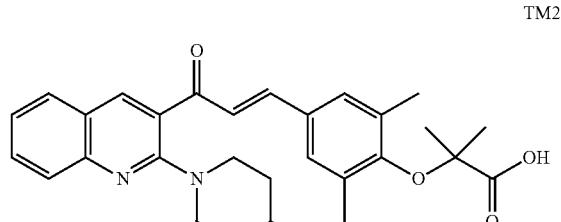
TM26
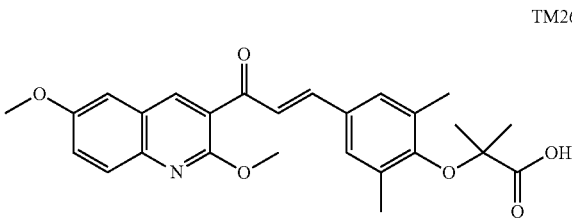
TM27
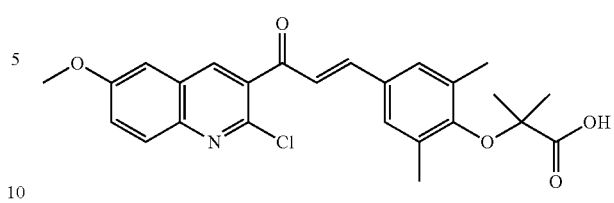
TM28
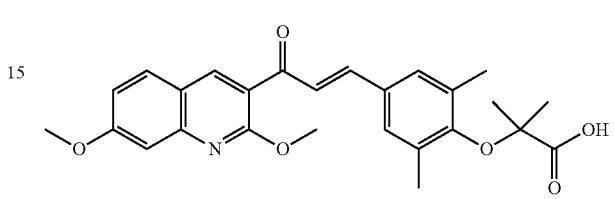
TM29
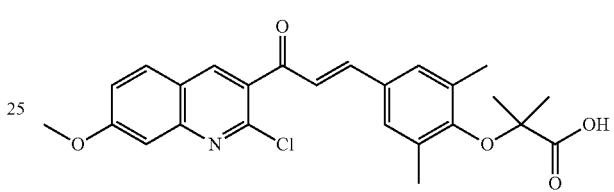
TM30
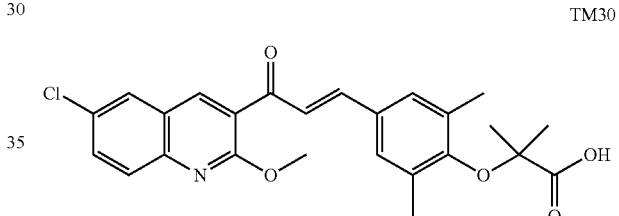
TM31
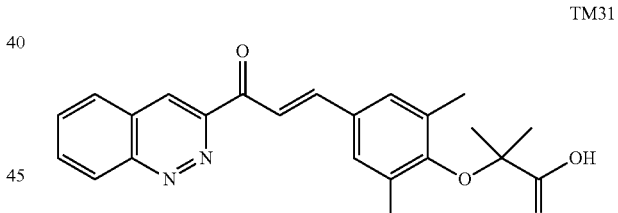
TM32
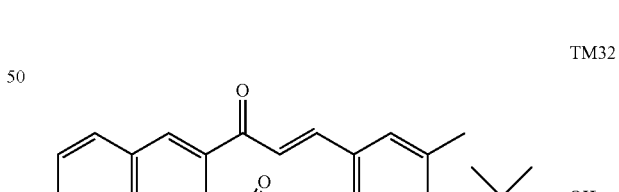
TM33
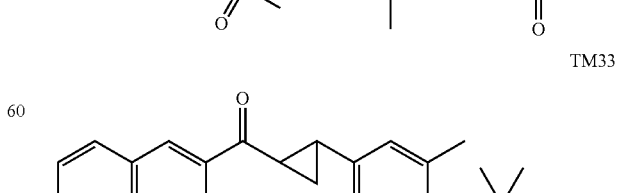

TM34

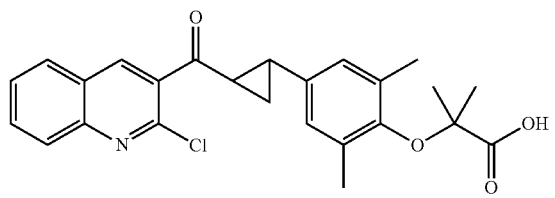

TM51

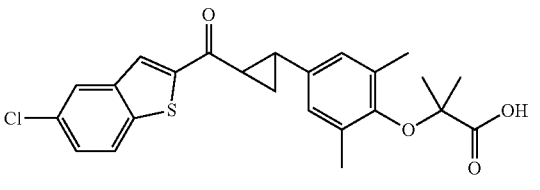

and

TM35

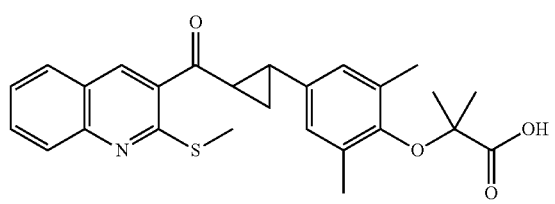

TM52

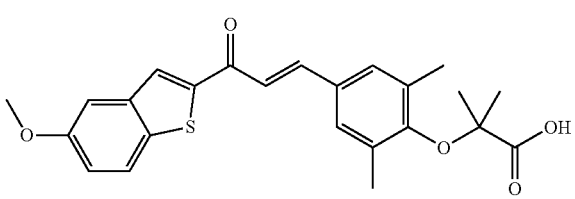

TM36

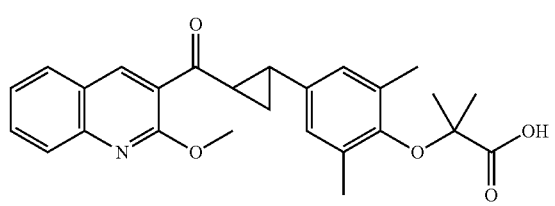

14. A pharmaceutical composition comprising a prophylactically or therapeutically effective amount of the compound according to claim 1 or the pharmaceutically acceptable salt, ester, stereoisomer, tautomer, polymorph, solvate, N-oxide, isotope-labeled compound, metabolite, prodrug or mixture thereof, and one or more pharmaceutically acceptable carriers.

15. A kit product, comprising the compound according to claim 1, or the pharmaceutically acceptable salt, ester, stereoisomer, tautomer, polymorph, solvate, N-oxide, isotope-labeled compound, metabolite, prodrug, or mixture thereof, and an optional package insert.

16. A kit product, comprising the pharmaceutical composition according to claim 14, and an optional package insert.

TM37

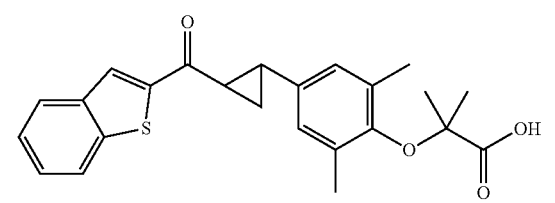

17. A pharmaceutical composition, comprising a prophylactically or therapeutically effective amount of the compound according to claim 12 or the pharmaceutically acceptable salt, ester, stereoisomer, tautomer, polymorph, solvate, N-oxide, isotope-labeled compound, metabolite, prodrug or mixture thereof, and one or more pharmaceutically acceptable carriers.

TM38

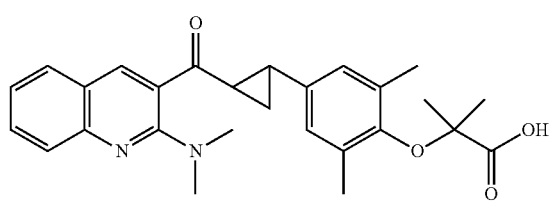

18. A method for treating a PPAR-related disease or condition, comprising administering to a subject having a disease associated with PPAR an effective amount of the compound according to claim 1 or the pharmaceutically acceptable salt, ester, stereoisomer, tautomer, polymorph, solvate, N-oxide, isotope-labeled compound, metabolite, prodrug or mixture thereof, or a pharmaceutical composition comprising the same and one or more pharmaceutically acceptable carriers.

TM49

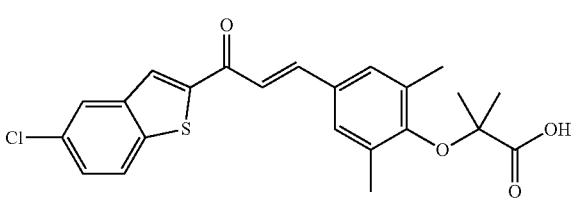

19. A method for activating PPAR in a cell, comprising the step of contacting the cell with an effective amount of the compound according to claim 1 or the pharmaceutically acceptable salt, ester, stereoisomer, tautomer, polymorph, solvate, N-oxide, isotope-labeled compound, metabolite, prodrug or mixture thereof, or a pharmaceutical composition comprising the same and one or more pharmaceutically acceptable carriers.

TM50

20. A method for preparing the compound according to claim 1, comprising the following steps:

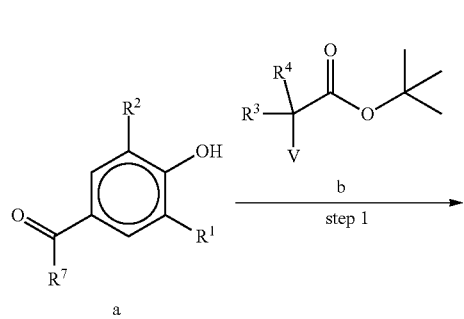

a

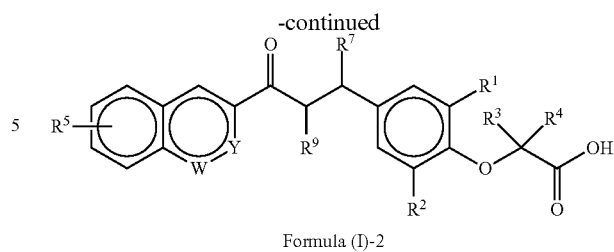

Formula (I)-2 or the method comprises the steps of:

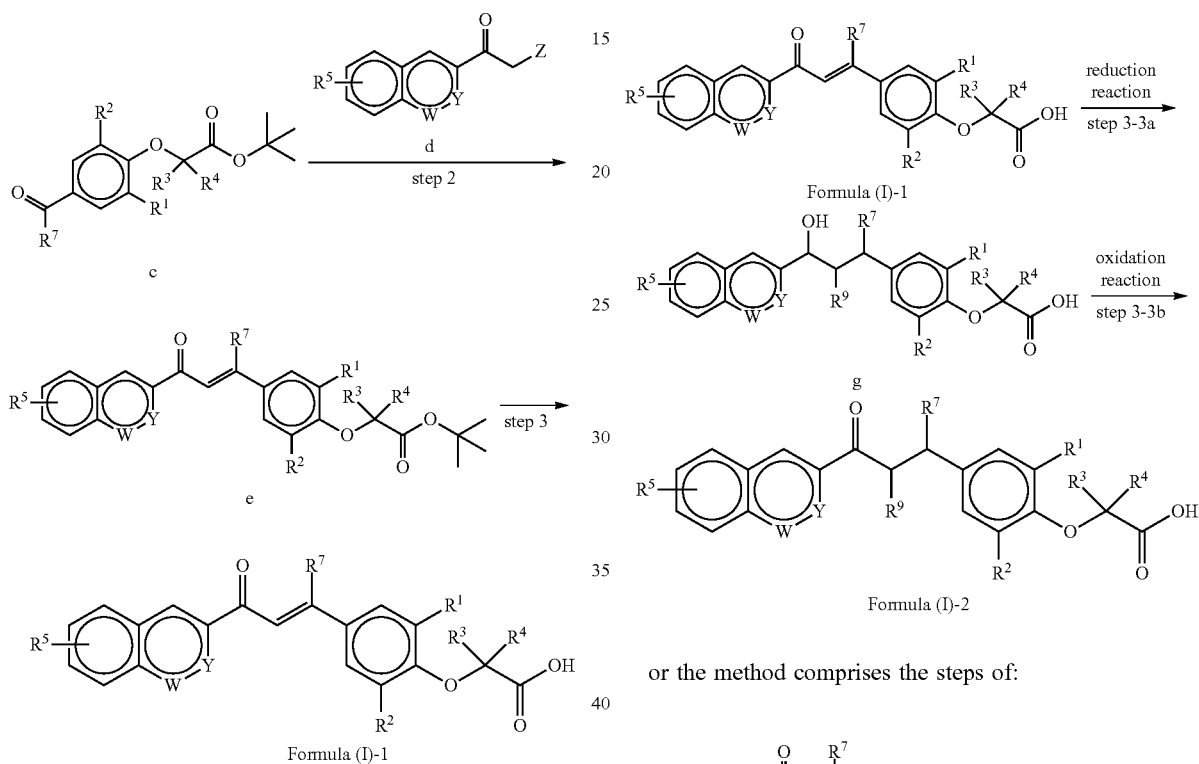

wherein, V represents halogen or $C_{1-3}$ alkyl sulfonic ester group optionally substituted by halogen; Z is selected from H, Cl, Br, I and —P(O)(OEt)$_2$; or the method comprises the steps of:

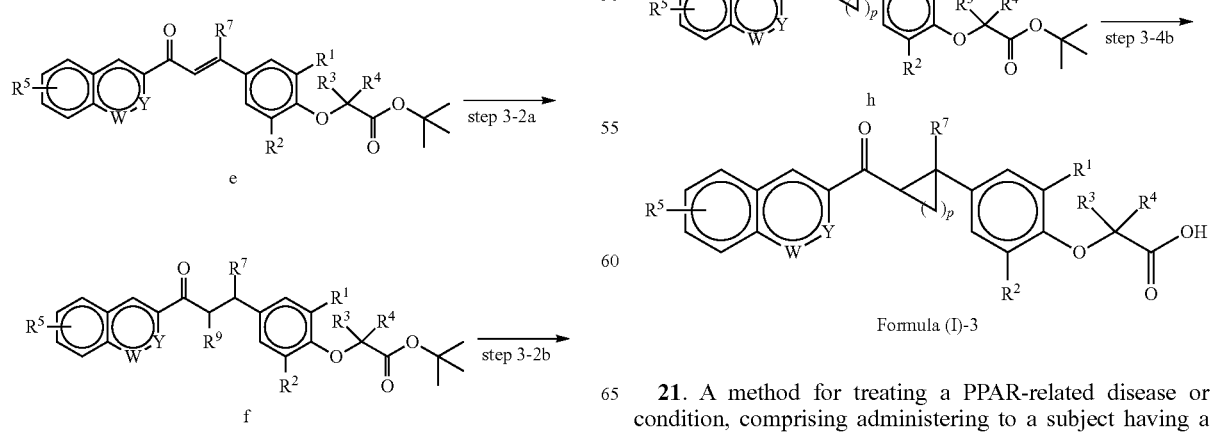

21. A method for treating a PPAR-related disease or condition, comprising administering to a subject having a disease associated with PPAR an effective amount of the compound according to claim 12 or the pharmaceutically acceptable salt, ester, stereoisomer, tautomer, polymorph, solvate, N-oxide, isotope-labeled compound, metabolite, prodrug or mixture thereof, or a pharmaceutical composition comprising the same and one or more pharmaceutically acceptable carriers.

22. The method according to claim 18, wherein the PPAR is PPAR α and/or PPAR δ.

23. The method according to claim 18, wherein the disease or condition is a liver disease.

24. The method according to claim 18, wherein the disease or condition is selected from liver fibrosis or fatty liver disease.

25. The method according to claim 18, wherein the disease or condition is NAFLD.

26. The method according to claim 18, wherein the disease or condition is SFL or NASH.

27. The method according to claim 19, wherein the PPAR is PPAR α and/or PPAR δ.

28. The method according to claim 21, wherein the PPAR is PPAR α and/or PPAR δ.

29. The method according to claim 21, wherein the disease or condition is a liver disease.

30. The method according to claim 21, wherein the disease or condition is selected from liver fibrosis or fatty liver disease.

31. The method according to claim 21, wherein the disease or condition is NAFLD.

32. The method according to claim 21, wherein the disease or condition is SFL or NASH.

* * * * *